United States Patent
Davis et al.

(10) Patent No.: US 10,988,537 B2
(45) Date of Patent: *Apr. 27, 2021

(54) ANTIBODIES COMPRISING CHIMERIC CONSTANT DOMAINS

(71) Applicant: Regeneron Pharmaceuticals, Inc., Tarrytown, NY (US)

(72) Inventors: Samuel Davis, New York, NY (US); Eric Smith, New York, NY (US); Supriya Patel, Mamaroneck, NY (US)

(73) Assignee: Regeneren Pharmaceuticals, Inc., Tarrytown, NY (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/128,907

(22) Filed: Sep. 12, 2018

(65) Prior Publication Data

US 2018/0371090 A1    Dec. 27, 2018

Related U.S. Application Data

(60) Continuation of application No. 15/147,791, filed on May 5, 2016, now Pat. No. 10,106,610, which is a division of application No. 14/170,166, filed on Jan. 31, 2014, now Pat. No. 9,359,437.

(60) Provisional application No. 61/759,578, filed on Feb. 1, 2013.

(51) Int. Cl.
C07K 16/46 (2006.01)
C07K 16/28 (2006.01)
C12N 15/85 (2006.01)

(52) U.S. Cl.
CPC ...... *C07K 16/2809* (2013.01); *C07K 16/2887* (2013.01); *C07K 16/2896* (2013.01); *C07K 16/46* (2013.01); *C12N 15/85* (2013.01); *C07K 2317/21* (2013.01); *C07K 2317/24* (2013.01); *C07K 2317/31* (2013.01); *C07K 2317/52* (2013.01); *C07K 2317/53* (2013.01); *C07K 2317/71* (2013.01); *C07K 2317/732* (2013.01); *C07K 2317/734* (2013.01); *C07K 2317/92* (2013.01); *C07K 2317/94* (2013.01)

(58) Field of Classification Search
CPC ............................ C07K 16/2809; C07K 16/46
USPC ...................................................... 530/387.3
See application file for complete search history.

(56) References Cited

U.S. PATENT DOCUMENTS

| 5,624,821 | A | 4/1997 | Winter et al. |
|---|---|---|---|
| 5,648,260 | A | 7/1997 | Winter et al. |
| 6,180,377 | B1 | 1/2001 | Morgan et al. |
| 7,396,917 | B2 | 7/2008 | Bowdish et al. |
| 7,563,441 | B2 | 7/2009 | Graus et al. |
| 7,597,889 | B1 | 10/2009 | Armour et al. |
| 7,608,260 | B2 | 10/2009 | Schenerman et al. |
| 7,700,097 | B2 | 4/2010 | Braslawsky et al. |
| 7,700,099 | B2 | 4/2010 | Strohl |
| 7,728,114 | B2 | 6/2010 | Mach et al. |
| 7,820,166 | B2 | 10/2010 | Lanzavecchia et al. |
| 7,824,684 | B2 | 11/2010 | Graus et al. |
| 7,867,491 | B2 | 1/2011 | Yang et al. |
| 7,960,512 | B2 | 6/2011 | Stavenhagen et al. |
| 8,075,884 | B2 | 12/2011 | Bowdish et al. |
| 8,084,026 | B2 | 12/2011 | Glaser et al. |
| 8,153,583 | B2 | 4/2012 | Carton et al. |
| 8,236,314 | B2 | 8/2012 | Kai et al. |
| 8,268,972 | B2 | 9/2012 | Whitfield et al. |
| 8,383,109 | B2 | 2/2013 | Lazar et al. |
| 8,409,568 | B2 | 4/2013 | Gao et al. |
| 8,961,967 | B2 | 2/2015 | Strohl et al. |
| 9,359,437 | B2 | 6/2016 | Davis et al. |
| 10,106,610 | B2 | 10/2018 | Davis et al. |
| 10,179,819 | B2 | 1/2019 | Kirshner et al. |
| 10,738,130 | B2 | 8/2020 | Haber et al. |
| 10,772,972 | B2 | 9/2020 | Rudge et al. |
| 2005/0037000 | A1 | 2/2005 | Stavenhagen et al. |
| 2005/0226876 | A1 | 10/2005 | Graus et al. |
| 2005/0244403 | A1 | 11/2005 | Lazar et al. |
| 2007/0009523 | A1 | 1/2007 | Presta |
| 2007/0041972 | A1 | 2/2007 | Rother et al. |
| 2009/0117133 | A1 | 5/2009 | Arnason et al. |
| 2009/0162901 | A1 | 6/2009 | Chen et al. |
| 2009/0252729 | A1 | 10/2009 | Farrington et al. |
| 2010/0105874 | A1 | 4/2010 | Schuurman et al. |
| 2010/0166749 | A1 | 7/2010 | Presta |
| 2010/0267934 | A1 | 10/2010 | Winkel et al. |

(Continued)

FOREIGN PATENT DOCUMENTS

| EP | 0327378 B1 | 12/1996 |
|---|---|---|
| EP | 2918604 A1 | 9/2015 |

(Continued)

OTHER PUBLICATIONS

Richards et al (Mol Cancer Ther, 2008, 7(8): 2517-2527).*

(Continued)

*Primary Examiner* — Sean E Aeder

(74) *Attorney, Agent, or Firm* — Schwabe, Williamson & Wyatt PC; Todd Samelman

(57) ABSTRACT

Antibodies, antigen-binding proteins and Fc-fusion proteins that comprise recombinant polypeptides containing a chimeric heavy chain constant region sequence are provided that bind to certain Fc receptors however have reduced effector functions. Methods of making constructs for expression of such chimeric Fc-containing antibodies, antigen-binding proteins and Fc-fusion proteins in cell systems, and methods of producing and isolating the chimeric Fc-containing proteins are provided.

20 Claims, 13 Drawing Sheets
Specification includes a Sequence Listing.

(56) References Cited

U.S. PATENT DOCUMENTS

| | | |
|---|---|---|
| 2010/0298542 A1 | 11/2010 | Igawa et al. |
| 2010/0325744 A1 | 12/2010 | Schuurman et al. |
| 2010/0331527 A1 | 12/2010 | Davis et al. |
| 2011/0077383 A1 | 3/2011 | Dall'Acqua et al. |
| 2011/0212087 A1 | 9/2011 | Strohl et al. |
| 2011/0245473 A1 | 10/2011 | Igawa et al. |
| 2011/0263830 A1 | 10/2011 | Goetsch et al. |
| 2011/0293607 A1 | 12/2011 | Labrijn et al. |
| 2012/0065379 A1 | 3/2012 | Igawa et al. |
| 2012/0071634 A1 | 3/2012 | Igawa et al. |
| 2012/0100140 A1 | 4/2012 | Reyes et al. |
| 2012/0189643 A1 | 7/2012 | Carton et al. |
| 2012/0225058 A1 | 9/2012 | Lazar et al. |
| 2012/0237515 A1 | 9/2012 | Bell et al. |
| 2012/0238729 A1 | 9/2012 | Kuramochi et al. |
| 2012/0251531 A1 | 10/2012 | Baehner et al. |
| 2012/0276096 A1 | 11/2012 | Yang et al. |
| 2012/0276097 A1 | 11/2012 | Yang et al. |
| 2013/0011386 A1 | 1/2013 | Brerski et al. |
| 2013/0101581 A1 | 4/2013 | Kuramochi et al. |
| 2013/0108623 A1 | 5/2013 | D'Angelo et al. |
| 2013/0129723 A1 | 5/2013 | Blankenship et al. |
| 2013/0251707 A1 | 9/2013 | Kontermann et al. |
| 2014/0088295 A1 | 3/2014 | Smith et al. |
| 2014/0112914 A1 | 4/2014 | Nezu et al. |
| 2014/0120581 A1 | 5/2014 | Niwa et al. |
| 2015/0166661 A1 | 6/2015 | Chen et al. |
| 2015/0203579 A1 | 7/2015 | Papadopoulos et al. |
| 2016/0168247 A1 | 6/2016 | Van Den Brink et al. |
| 2016/0347839 A1 | 12/2016 | Davis et al. |
| 2017/0008951 A1 | 1/2017 | Block et al. |
| 2017/0051074 A1 | 2/2017 | Kirshner et al. |
| 2018/0104357 A1 | 4/2018 | Rudge et al. |
| 2018/0112001 A1 | 4/2018 | Haber et al. |
| 2018/0118848 A1 | 5/2018 | Haber et al. |
| 2018/0303953 A1 | 10/2018 | Van Berkel et al. |
| 2019/0127480 A1 | 5/2019 | Kirshner et al. |
| 2019/0389966 A1 | 12/2019 | Crawford |
| 2020/0317810 A1 | 10/2020 | Haber et al. |

FOREIGN PATENT DOCUMENTS

| | | |
|---|---|---|
| WO | 97/028267 A1 | 8/1997 |
| WO | 99/043713 A1 | 9/1999 |
| WO | 99/058572 A1 | 11/1999 |
| WO | 00/042072 A2 | 7/2000 |
| WO | 03/026490 A2 | 4/2003 |
| WO | 2008/147143 A2 | 12/2008 |
| WO | 10/054212 A1 | 5/2010 |
| WO | 10/063785 A2 | 6/2010 |
| WO | 10/085682 A2 | 7/2010 |
| WO | 11/137362 A1 | 11/2011 |
| WO | 12/022982 A2 | 2/2012 |
| WO | 12/035141 A1 | 3/2012 |
| WO | 12/087746 A1 | 6/2012 |
| WO | 2012/073985 A1 | 6/2012 |
| WO | 13/012733 A1 | 1/2013 |
| WO | 13/026839 A1 | 2/2013 |
| WO | 13/112986 A1 | 8/2013 |
| WO | 13/184761 A1 | 12/2013 |
| WO | 14/012085 A1 | 1/2014 |
| WO | 14/022540 A1 | 2/2014 |
| WO | 14/047231 A1 | 3/2014 |
| WO | 14/051433 A1 | 4/2014 |
| WO | 14/056783 A1 | 4/2014 |
| WO | 14/121087 A1 | 8/2014 |
| WO | 2015/006749 A2 | 1/2015 |
| WO | 15/091738 A1 | 6/2015 |
| WO | 15/143079 A1 | 9/2015 |
| WO | 16/161010 A2 | 10/2016 |
| WO | 17/053856 A1 | 3/2017 |

OTHER PUBLICATIONS

Chan et al (Nature Reviews, 2010, 10: 301-316).*
"IgG-Fc Engineering for Therapeutic Use," InvivoGen Insight, 1 page, (2006). [Author Unknown] [Retrieved from the Internet Apr. 4, 2014: <URL: http://www.invivogen.comiclocs/Insight200605 pdf >].
"IgG-Fe engineering for therapeutic use," Invivogen, 2 pages, (2007). [Author Unknown] [Retrieved from the Internet Jan. 12, 2011: <URL: http://www.invivogen.com/ressource.php?ID=22>].
Aalberse et al., "IgG4 breaking the rules," Immunology, 105(1):9-19, (2002).
Advani et al., "New immune strategies for the treatment of acute lymphoblastic leukemia: antibodies and chimeric antigen receptors," Hematology, vol. 2013 (No. 1): (Dec. 1, 2013).
Alegre et al., "Effect of a Single Amino Acid Mutation on the Activating and Immunosuppressive Properties of a Humanized OKT3 Monoclonal Antibody", J Immunol, 148(11):3461-3468, ISSN: 0022-1767, (1992).
Almagro et al., "Humanization of antibodies," Front Biosci, vol. 13, pp. 1619-163, (2008).
An et al., "IgG2m4, an engineered antibody isotype with reduced Fc function," Landes Bioscience, 1(6):572-579, (2009).
Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrailsregister. eu/ctr-search/trial/2015-001697-17/ES>].
Anonymous, "Study of REGN2810 and REGN1979 in Patients with Lymphoma or Acute Lymphoblastic Leukemia." [Retrieved from the Internet Mar. 15, 2017: <URL: https://www.api.liveclinicaltrials. com/trialpage?dcn=10963&city=Baltimore&country=UnitedStates &start=20&state=Maryland&conditions=lymphoma&id= 207048402254>].
Armour et al., "Differential binding to human FcγRIIa and FcγRIIb receptors by human IgG wildtype and mutant antibodies," Molecular Immunology, 40:585-593, (2003).
Armour et al., "Recombinant human IgG molecules lacking Fcγ receptor I binding and monocyte triggering activities", J. Immunol., 29:2613-2624, (1999).
Baeuerle et al., "Bispecific T-cell engaging antibodies for cancer therapy," Cancer Res, 69(12):4941-4944, doi: 10.1158/0008-5472. CAN-09-0547, (2009).
Becker et al., "Evaluation of a combinatorial cell engineering approach to overcome apoptotic effects in XBP-1(s) expressing cells," Journal of Biotechnology, vol. 164:198-206, (2010).
Bloom et al., "Intrachain disulfide bond in the core hinge region of human IgG4," Protein Science, 6:407-415, (1997).
Brekke et al., "The structural requirements for complement activation by IgG: does it hinge on the hinge?" Today, 16(2):85-90, (1995).
Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplantation, 43:383-397, (2009).
Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," Journal of Translation Medicine, vol. 11:160, (2013); 9 pages. [Retrieved from the Internet at: <http://www.translational-medicine.com/content/11/1/1160>].
Canfield et al., "The Binding Affinity of Human IgG for Its High Affinity Fc Receptor is Determined by Multiple Amino Acids in the $C_H2$ Domain and is Modulated by the Hinge Region," J. Exp. Med., 173(6):1483-1491, (1991).
Cao et al., "Multiformat T-Cell-Engaging Bispecific Antibodies Targeting Human Breast Cancers," Angew Chem Int Ed Engl, 54(24):7022-7027, doi: 10.1002/anie.201500799, (2015).
Chappel et al., "Identification of a Secondary FcγRI Binding Site within a Genetically Engineered Human IgG," Journal of Biological Chemistry, 268(33): 25124-25131, (1993).

(56) References Cited

OTHER PUBLICATIONS

Chappel et al., "Identification of the FC-Gamma Receptor Class I Binding Site in Human Igg Through the Use of Recombinant Igg1-Igg2 Hybrid and Point-Mutated Antibodies," Proc. Natl. Acad. Sci. USA, 88(20):9036-9040, (1991).
Clark, "IgG Effector Mechanisms," Chem Immunol. Basel, Karger, 65:88-110, (1997).
Dall'Acqua et al., "Modulation of the Effector Functions of a Human IgG1 through Engineering of Its Hinge Region," Journal of Immunology, 177:1129-1138, (2006).
Damschroder et al., "Analysis of human and primate CD2 molecules by protein sequence and epitope mapping with anti-human CD2 antibodies," Molecular Immunology, vol. 41:985-1000, (2004).
Dangl et al., "Segmental flexibility and complement fixation of genetically engineered chimeric human, rabbit and mouse antibodies," The EMBO Journal, 7(7):1989-1994, (1988).
Duncan et al., "Localization of the binding site for the human high-affinity Fc receptor on IgG", Nature, 332:563-564, (1988).
Fossati et al., "Immunological changes in the ascites of cancer patients after intraperitoneal administration of the bispecific antibody catumaxomab (anti-EpCAManti-CD3)," Gynecol Oncol, 138(2):343-351, doi: 10.1016/J.YGYNO.2015.06.003, (2015).
Gergely et al., "The two binding-site models of human IgG binding Fcγ receptors", The FASEB Journal, 4:3275-3283, (1990).
Greenwood et al., "Structural Motifs Involved in Human IGG Antibody Effector Functions," Eur. J. Immunology, 23(5):1098-1104, (1993).
Grubb, "Human immunoglobulin allotypes and Mendelian polymorphisma of the human immunoglobulin genes," Oss CJ, Regenmortel MHV (eds): Immunochemistry, New York, Dekker; pp. 47-68 (1994).
Harlow et al., Antibodies, A Laboratory Manual, Cold Spring Harbor Laboratory; (1998) pp. 37-47.
Haso et al., "Anti-CD22-chimeric antigen receptors targeting B-cell precursor acute lymphoglastic leukemia," Blood, vol. 121 (No. 7):1165-1174, Feb. 14, 2013.
Hezareh et al., "Effector function activities of a panel of mutants of a broadly neutralizing antibody against human immunodeficiency virus type 1," J Virol, 75(24):12161-12168, doi: 10.1128/JVI.75.24.12161-12168.2001, (2001).
Jacobsen et al., "Molecular and Functional Characterization of Cynomolgus Monkey IgG Subclasses," Journal Immunology, 186:341-349, (2011).
Jefferis et al., "Interaction sites on human IgG-Fc for FcγR: current models", Immunology Letters, 82:57-65, (2002).
Jefferis et al., "Recognition sites on human IgG for Fcγ receptors: the role of glycosylation," Immunology Letters, 44:111-117, (1995).
Jung et al., "Target Cell-Induced T Cell Activation with Bi- and Trispecific Antibody Fragments", Eur J Immunol, vol. 21, pp. 2431-2435, doi: 10.1002/EJI.1830211020, (1991).
Kohnke et al., "Increase of PD-L1 expressing B-precursor All cells in a patient resistant to the CD19/CD3-bispecific T cell engager antibody blinatumomab," Journal of Hematology & Oncology, vol. 8 (No. 111): 5 pages, (2015).
Kumar et al., "Expression of CD20 in B Cell Precursor Acute Lymphoblastic Leukemia," Indian J Hematol Blood Transfus, vol. 30 (No. 1):16-18, (2014).
Labrijn et al., "When binding is enough: nonactivating antibody formats", Current Opinion in Immunology, 20:479-485, (2008).
Lau et al., "Chimeric Anti-CD14 IGG2/4 Hybrid Antibodies for Therapeutic Intervention in Pig and Human Models of Inflammation," J Immunol, 191:4769-4777, doi: 10.4049/jimmunol.1301653, (2013).
Li et al., "A Novel Bispecific Antibody, S-Fab, Induces Potent Cancer Cell Killing," J Immunother, 38(9):350-356, doi: 10.1097/CJI.0000000000000099, (2015).
Lum et al., "CD2O-Targeted T Cells after Stem Cell Transplantation for High Risk and Refractory Non-Hodgkin's Lymphoma," Pbiol Blood Marrow Transplant, 19(6):925-933, (2013).
Lum et al., "Multiple infusions of CD20-targeted T cells and low-dose IL-2 after SCT for high-risk non-Hodgkin's lymphoma: A pilot study," Bone Marrow Transplantation, 49:73-79, (2004). [Published online Sep. 23, 2013].
Lund et al., "Human FcγRI and FcγRII Interact with Distinct but Overlapping Sites on Human IgG", Journal of Immunology, 147(8):2657-2662, (1991).
Michaelsen et al., "Antibody Dependent Cell-Mediated Cytotoxicity Induced by Chimeric Mouse-Human IgG Subclasses and IgG3 Antibodies with Altered Hinge Region," Molecular Immunology, 29(3):319-326, (1992).
Morgan et al., "The N-terminal end of the CH2 domain of chimeric human IgG1 anti-HLA-DR is necessary for Gig, FcγRI and FcγRII binding," Immunology, 86:319-324, (1995).
Mueller et al., "Humanized Porcine VCAM-Specific Monoclonal Antibodies with Chimeric IgG2/G4 Constant Regions Block Human Leukocyte Binding to Porcine Endothelial Cells," Molecular Immunology, 34(6): 441-452, (1997).
Natsume et al., "Engineered Antibodies of IgG1IIgG3 Mixed Isotype with Enhanced Cytotoxic Activities," Cancer Research, 68:(10):3863-3872, (2008).
NCBI MedGen 44126 definition for "Pre-B Acute Lumphoblastic Leukemia"; retrieved from the Internet on Dec. 11, 2018, pp. 1-4, available at <https://www.ncbi.nlm.nih.gov/medgen/44126/> (2018).
Oganesyan et al., "Structural characterization of a human Fc fragment engineered for lack of effector functions," Acta Crystallographica Section D Biological Crystallography, D64:700-704, (2008).
Ontology Lookup Service, EFO 0000220, "Acute lumphoblastic leukemia", retrieved from the Internet on Dec. 11, 2018, pp. 1-6, available at <https://www.ebi.ac.uk/ols/ontologies/efo/terms?short_form=EFO_0000220> (2018).
Patel et al., "IGG subclass variation of a monoclonal antibody binding to human Fc-gamma receptors", American Journal of Biochemistry and Biotechnology, 9(3):206-218, (2013).
Peters et al., "Engineering an Improved IgG4 Molecule with Reduced Disulfide Bond Heterogeneity and Increased Fab Domain Thermal Stability," Journal of Biological Chemistry, 287(29): 24525-24533, (2012).
Reddy et al., "Elimination of Fc Receptor-Dependent Effector Functions of a Modified IgG4 Monoclonal Antibody to Human CD4," Journal of Immunology, 164:1925-1933, (2000).
Rother et al., : "Discovery and development of the complement inhibitor eculizumab for the treatment of paroxysmal nocturnal hemoglobinuna," Nature Biotechnology, 25(11):1256-1264, (2007).
Roux et al., "Comparisons of the ability of human IgG3 hinge mutants, IgM, IgE and IgA2, to form small immune complexes: Arole for flexibility and geometry," The Journal of Immunology, 161:4083-4090, (1998).
Roux et al., "Flexibility of Human IgG Subclasses," Journal of Immunology, 159:3372-3382, (1997).
Salfeld, "Isotype selection in antibody engineering," Nature Biotechnology, 25(12):1369-1372, (2007).
Sarmay et al., "Mapping and Comparison of the Interaction Sites on the Fc Region of IgG Responsible for Triggering Antibody Dependent Cellular Cytotoxicity (ADCC) through Different Types of Human Fcγ Receptor," Molecular Immunology, 29(5):633-639, (1992).
Sathish et al., "Challenges and approaches for the development of safer immunomodulatory biologics," Nature Reviews Drug Discovery, 12:306-324, (2013).
Schaefer et al., "Immunoglobulin domain crossover as a generic approach for the production of bispecific IgG antibodies," PNAS, 108(27):11187-11192, doi: 10.1073/pnas.1019002108, (2011).
Schuster et al., "Immunotherapy with the trifunctional anti-CD20 x anti-CD3 antibody FBTA05 Lymphomun) in paediatric high-risk patients with recurrent CD20-positive B cell malignancies," British Journal of Haematolgy, vol. 169 (No. 1): (Apr. 11, 2015); pp. 90-102.
Sensel et al., "Amino Acid Differences in the N-Terminus of CH2 Influence the Relative Abilities of IgG2 and IgG3 to Activate Complement", Molecular Immunology, 34(14):1019-1029, (1997).

(56) References Cited

OTHER PUBLICATIONS

Shields et al., High resolution mapping of the binding site on human IgG1 for FcgammaRI, FcganmaRII, FcgammaRIII, and FcRn and design of IgG1 variants with improved binding to the FcgammaR, J Biol Chem, 276(9):6591-6604, doi: 10.1074/JBC.M009483200, (2001).

Siberil et al., "Molecular aspects of human FcyR interactions with IgG: Functional and therapeutic consequences," Immunology Letters, 106:111-118, (2006).

Smith et al., "A novel, native-format bispecific antibody triggering T-cell killing of B-cell is robustly active in mouse tumor models and cynomolgus monkeys," Scientific Reports, vol. 5(No. 11):(Dec. 11, 2015); p. 17943.

Stanglmaier et al., "Bi20 (FBTA05), a novel trifunctional bispecific antibody (anti-CD20 x anti-CD3), mediates efficient killing of B-cell lymphoma cells even with very low CD20 expression levels", Int. J. Cancer, 123(5):1181-1189, (2008).

Stevenson, "Chemical Engineering at the Antibody Hinge," Chem Immunol. Basel, Karger, 65:57-72, (1997).

Strop et al., "Generating Bispecific Human IgG1 and IgG2 Antibodies from Any Antibody Pair", J. Mol. Biol., 420(3):204-219, (2012).

Stubenrauch et al., "Impact of Molecular Processing in the Hinge Region of Therapeutic IgG4 Antibodies on Disposition Profiles in Cynomolgus Monkeys," Drug Metabolism and Disposition, vol. 38(No. 1):84-91, (2010).

Sun et al., "Anti-CD20/CD3 T cell—dependent bispecific antibody for the treatment of B cell malignancies," Science Translational Medicine, 7(287):287ra70, 10 pages, (2015).

Tan et al., "Influence of the hinge region on complement activation, C1q binding, and segmental flexibility in chimeric human immunoglobulins,", Proc. Natl. Acad. Sci. USA, 87:162-166, (1990).

Thomas et al., "Chemoimmunotherapy with a Modified Hyper-CVAD and Rituximab Regimen Improves Outcome in De Novo Philadelphia Crhomosome-Negative Precursor B-Lineage Acute Lumphoblastic Leukemia," Journal of Clinical Oncology, vol. 28 (No. 24):3880-3889; Aug. 20, 2010.

Topp et al., "Safety and activity of blinatumomab for adult patients with relapsed or refractory B-precursor acute lymphoblastic leukaemia: a multicentre, single-arm, phase 2 study," Publication, vol. 16:57-66, (Jan. 2015).

Tsai et al., "Regulation of CD20 in Rituximab-Resistant Cell Lines and B-cell Non-Hodgkin Lymphoma," Clinical Cancer Research, vol. 18(No. 4):1039-1050, (2012).

U.S. Appl. No. 14/170,166, Non-Final Office Action dated Dec. 21, 2015.

U.S. Appl. No. 14/170,166, Notice of Allowance dated Apr. 11, 2016.

U.S. Appl. No. 14/170,166, Requirement for Restriction/Election dated Jul. 27, 2015.

U.S. Appl. No. 15/147,791, Non-Final Office Action dated Sep. 27, 2017.

U.S. Appl. No. 15/147,791, Notice of Allowance dated Mar. 1, 2018.

U.S. Appl. No. 15/147,791, Notice of Allowance dated Jun. 12, 2018.

Vafa, et al., "An engineered Fc variant of an IgG eliminates all immune effector functions via structural perturbations", 65:114-126, (2014). (Published online Jul. 17, 2013).

Vidarsson et al., "IgG Subclasses and Allotypes: From Structure to Effector Functions," Frontiers in Immunology, vol. 5, Article 520,18 pages, doi: 10.3389/fimmu.2014.00520, (2014).

Ward et al., "The effector functions of immunoglobulins: implications for therapy," Therapeutic Immunology, 2:77-94, (1995).

WIPO Application No. PCT/US2014/014175, PCT International Preliminary Report on Patentability dated Aug. 13, 2015.

WIPO Application No. PCT/US2014/014175, PCT International Search Report and Written Opinion of the International Searching Authority dated Jul. 9, 2014.

WIPO Application No. PCT/US2016/025051, PCT International Search Report and Written Opinion of the International Searching Authority dated Oct. 12, 2016.

WIPO Application No. PCT/US2016/053525, PCT International Search Report and Written Opinion of the International Searching Authority dated Mar. 8, 2017.

Wolach et al., "Blinatumomab for the Treatment of Philadelphia Chromosome-Negative, Precursor B-cell Acute Lymphoblastic Leukemia," Clinical Cancer Research, vol. 21 (No. 19):4262-4269, (2015).

Wu et al., "Fab-based bispecific antibody formats with robust biophysical properties and biological activity," MABS, pp. 470-482, ISSN: 1942-0870, (2015).

Wypych et al., "Human IgG2 Antibodies Display Disulfide-mediated Structural Isoforms," Journal of Biological Chemistry, 283(23):16194-16205, (2008).

Xu et al., "Residue at Position 331 in the Igg1 and Igg4 Ch2 Domains Contributes to Their Differential Ability to Blind and Activate Complement," Journal of Biological Chemistry, 269(5):3469-3474, (1994).

U.S. Appl. No. 14/661,334, filed Mar. 18, 2015, US 2015-0266966, Pending.

U.S. Appl. No. 15/527,002, filed Nov. 17, 2015, US 2018-0194841, Pending.

U.S. Appl. No. 15/386,443, filed Dec. 21, 2016, US 2017-0174781, Pending.

U.S. Appl. No. 15/562,881, filed Mar. 30, 2016, US 2018-0282411, Pending.

U.S. Appl. No. 15/934,447, filed Mar. 23, 2018, US 2018-0215823, Pending.

U.S. Appl. No. 61/759,578, filed Feb. 1, 2013, Expired.

U.S. Appl. No. 14/170,166, filed Jan. 31, 2014, U.S. Pat. No. 9,359,437, Issued.

U.S. Appl. No. 15/147,791, filed May 5, 2016, U.S. Pat. No. 10,106,610, Issued.

PCT/US2014/014175, filed Jan. 31, 2014, WO 2014/022540, Expired.

U.S. Appl. No. 61/955,663, filed Mar. 19, 2014, Expired.

U.S. Appl. No. 61/981,641, filed Apr. 18, 2014, Expired.

U.S. Appl. No. 62/007,385, filed Jun. 3, 2014, Expired.

U.S. Appl. No. 62/033,460, filed Aug. 5, 2014, Expired.

U.S. Appl. No. 14/661,334, filed Mar. 18, 2015, U.S. Pat. No. 10,550,193, Issued.

PCT/US2015/021322, filed Mar. 18, 2015, WO 2015/143079, Expired.

U.S. Appl. No. 16/716,980, filed Dec. 17, 2019, US-2020-0115464, Pending.

U.S. Appl. No. 62/080,716, filed Nov. 17, 2014, Expired.

U.S. Appl. No. 62/160,788, filed May 13, 2015, Expired.

PCT/US2015/061139, filed Nov. 17, 2015, WO 2016/081490, Expired.

U.S. Appl. No. 15/527,002, filed Nov. 17, 2015, U.S. Pat. No. 10,662,244, Issued.

U.S. Appl. No. 62/306,031, filed Mar. 9, 2016, Expired.

U.S. Appl. No. 15/386,443, Dec. 21, 2016, US 2017-0174781, Abandoned.

PCT/US2016/068003, filed Dec. 21, 2016, WO 2017/112762, Expired.

U.S. Appl. No. 16/443,313, filed Jun. 17, 2019, Abandoned.

U.S. Appl. No. 62/140,350, filed Mar. 30, 2015, Expired.

PCT/US2016/025051, filed Mar. 30, 2016, WO 2016/161010, Expired.

U.S. Appl. No. 15/562,881, filed Mar. 30, 2016, U.S. Pat. No. 10,556,952, Issued.

U.S. Appl. No. 16/720,623, filed Dec. 19, 2019, US-2020-0109203, Pending.

U.S. Appl. No. 62/222,605, filed Sep. 23, 2015, Expired.

PCT/US2016/053525, filed Sep. 23, 2016, WO 2017/053856, Expired.

U.S. Appl. No. 15/780,504, filed Sep. 23, 2016, US 2018-0355038, Pending.

U.S. Appl. No. 61/704,029, filed Sep. 21, 2012, Expired.

U.S. Appl. No. 61/753,461, filed Jan. 17, 2013, Expired.

U.S. Appl. No. 61/763,110, filed Feb. 11, 2013, Expired.

U.S. Appl. No. 61/827,098, filed May 24, 2013, Expired.

U.S. Appl. No. 14/031,075, filed Sep. 19, 2013, U.S. Pat. No. 9,657,102, Issued.

U.S. Appl. No. 15/489,666, filed Apr. 17, 2017, US 2017-0320948, Pending.

(56) References Cited

OTHER PUBLICATIONS

PCT/US2013/060511, filed Sep. 19, 2013, WO 2014/047231, Expired.

U.S. Appl. No. 15/934,447, filed Mar. 23, 2018, US 2018-02158203, Pending.

Bae et al., "Identification of the amino acid residues involved in human IgG transport into egg yolk of Japanese quail," Molucular Immunology, vol. 47:1404-1410, (2010).

Bargou et al., "Tumor egression in Cancer Patients by Very Low Doses of a T Cell-Engaging Antibody," Science Magazine, vol. 321: 974-977, (2008).

Bortoletto et al., "Optimizing anti-CD3 affinity for effective T cell targeting against tumor cells," Eur. J. Immunol, vol. 32:3102-3107 (2002).

Kapur et al., "IgG-effector functions: The Good, The Bad and The Ugly," El Sevier, vol. 160:139-144, (2014).

Ruf et al., "Induction of a long-lasting antitumor immunity by a trifunctional bispecific antibody," Blood Journal, vol. 98, No. 9: 2526-2534, (2001).

Sun, "Structural Recognition of Immunoglobulins by Fc ɤ Receptors," Elsevier Science & Technology, Ch. 7:131-144, (2013).

U.S. Appl. No. 15/562,881, Notice of Allowance dated Jun. 12, 2019.

U.S. Appl. No. 15/562,881, Notice of Allowance dated Sep. 25, 2019.

U.S. Appl. No. 15/780,504, Requirement for Restriction/Election dated Apr. 7, 2020.

U.S. Appl. No. 15/780,504, Non-Final Office Action dated Oct. 20, 2020.

Weinglass et al., "Engineering Conformational Flexibility in the Lactose Permease of *Escherichia coli*: Use of Glycine-Scanning Mutagenesis to Rescue Mutant Glu325—Asp," Biochemistry, vol. 40:769-776, (2001).

\* cited by examiner

FIG. 1

Construction of chimeric hinge

| | | Upper Hinge | | | | | | | | | | | | Lower Hinge | | | | | | | |
|---|---|---|---|---|---|---|---|---|---|---|---|---|---|---|---|---|---|---|---|---|---|
| IgG1 EU numbering | 216 | 217 | 218 | 219 | 220 | 221 | 222 | 223 | 224 | 225 | 226 | 227 | | | | | | | | | |
| IgG1 Kabat numbering | 216 | 217 | 228 | 232ª 229ᵇ | 233ª 230ᵇ | 234ª 232ᵇ | 235ª | 236 | 237 | 238 | 239 | 240 | | | | | | | | | |
| IgG1 | E | P | K | S | C | D | K | T | H | T | C | P | | | | | | | | | |
| | | | | | | | | | | | | | IgG2 | P | C | P | A | P | P | V | A |
| | | | | | | | | | | | | | IgG2 EU numbering | 228 | 229 | 230 | 231 | 232 | 233 | 234 | 235 |
| | | | | | | | | | | | | | IgG2 Kabat numbering | 241 | 242 | 243 | 244 | 245 | 246 | 247 | 248 |
| IgG4 EU numbering | 216 | 217 | 218 | 219 | 220 | 221 | 222 | 223 | 224 | 225 | 226 | 227 | | | | | | | | | |
| IgG4 Kabat numbering | 226 | 227 | 228 | 229 | 230 | - 219ª 220ᵇ | - 220ª 230 | - | - | - | - | - | | | | | | | | | |
| IgG4 | E | S | K | Y | G | - | - | - | P | P | C | P | | | | | | | | | |

ª: means no corresponding number reported
ᵇ: means no corresponding amino acid
ᶜ: numbering according to the last updated IMGT Scientific Chart (IMGT®, the International ImMunoGeneTics information system®, http://www.imgt.org/IMGTScientificChart/Numbering/Hu_IGHGnber.html, created: 17 May 2001, last updated:10 Jan 2013)
ᵈ: numbering according to EU index as reported in Kabat, E.A. et al. Sequences of Proteins of Immunological Interest. 5th ed. US Department of Health and Human Services, NIH publication No. 91-3242 (1991)

FIG. 2

```
         10          20          30          40          50          60
ASTKGPSVFP  LAPSSKSTSG  GTAALGCLVK  DYFPEPVTVS  WNSGALTSGV  HTFPAVLQSS
                                  ← CH1  Hinge →        CH2 →
         70          80          90         100         110         120
GLYSLSSVVT  VPSSSLGTQT  YICNVNHKPS  NTKVDKKVEP  KSCDKTHTCP  PCPAPELLGG 130         140         150         160         170         180
PSVFLFPPKP  KDTLMISRTP  EVTCVVVDVS  HEDPEVKFNW  YVDGVEVHNA  KTKPREEQYN
                                              CH3 →
        190         200         210         220         230         240
STYRVVSVLT  VLHQDWLNGK  EYKCKVSNKA  LPAPIEKTIS  KAKGQPREPQ  VYTLPPSRDE 250         260         270         280         290         300
LTKNQVSLTC  LVKGFYPSDI  AVEWESNGQP  ENNYKTTPPV  LDSDGSFFLY  SKLTVDKSRW 310         320         330
QQGNVFSCSV  MHEALHNHYT  QKSLSLSPGK
```

Human IGHG1 heavy chain constant region
UniProtKB/Swiss-Prot Accn. No. P01857
(SEQ ID NO:13)

FIG. 3

```
          10         20         30         40         50         60
  ASTKGPSVFP LAPCSRSTSE STAALGCLVK DYFPEPVTVS WNSGALTSGV HTFPAVLQSS
                                  ←CH1 Hinge→         CH2→
          70         80         90        100        110        120
  GLYSLSSVVT VPSSNFGTQT YTCNVDHKPS NTKVDKTVER KCCVECPPCP APPVAGPSVF 130        140        150        160        170        180
  LFPPKPKDTL MISRTPEVTC VVVDVSHEDP EVQFNWYVDG VEVHNAKTKP REEQFNSTFR
                                       CH3→
         190        200        210        220        230        240
  VVSVLTVVHQ DWLNGKEYKC KVSNKGLPAP IEKTISKTKG QPREPQVYTL PPSREEMTKN 250        260        270        280        290        300
  QVSLTCLVKG FYPSDISVEW ESNGQPENNY KTTPPMLDSD GSFFLYSKLT VDKSRWQQGN 310        320
  VFSCSVMHEA LHNHYTQKSL SLSPGK
```

Human IGHG2 heavy chain constant region
UniProtKB/Swiss-Prot Accn. No. P01859
(SEQ ID NO:14)

FIG. 4

```
         10          20         30         40         50         60
ASTKGPSVFP LAPCSRSTSE STAALGCLVK DYFPEPVTVS WNSGALTSGV HTFPAVLQSS
                                  ←―CH1  Hinge―→       CH2―→
         70          80         90        100        110        120
GLYSLSSVVT VPSSSLGTKT YTCNVDHKPS NTKVDKRVES KYGPPCPSCP APEFLGGPSV 130         140        150        160        170        180
FLFPPKPKDT LMISRTPEVT CVVVDVSQED PEVQFNWYVD GVEVHNAKTK PREEQFNSTY
                                                        CH3―→
        190         200        210        220        230        240
RVVSVLTVLH QDWLNGKEYK CKVSNKGLPS SIEKTISKAK GQPREPQVYT LPPSQEEMTK 250         260        270        280        290        300
NQVSLTCLVK GFYPSDIAVE WESNGQPENN YKTTPPVLDS DGSFFLYSRL TVDKSRWQEG 310         320
NVFSCSVMHE ALHNHYTQKS LSLSLGK
```

Human IGHG4 heavy chain constant region
UniProtKB/Swiss-Prot Accn. No. P01861
(SEQ ID NO:15)

FIG. 5

```
SEQUENCE LISTING

<160> NUMBER OF SEQ ID NOS: 44

<210> SEQ ID NO 1
<211> LENGTH: 232
<212> TYPE: PRT
<213> ORGANISM: Artificial Sequence
<220> FEATURE:
<223> OTHER INFORMATION: Synthetic

<400> SEQUENCE: 1

Asp Lys Arg Val Glu Ser Lys Tyr Gly Pro Pro Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

```
Val Asp Val Ser Gln Glu Asp Pro Glu Val Gln Phe Asn Trp Tyr Val
     50                  55                  60
Asp Gly Val Glu Val His Asn Ala Lys Thr Lys Pro Arg Glu Glu Gln
 65                  70                  75                  80
Phe Asn Ser Thr Tyr Arg Val Val Ser Val Leu Thr Val Leu His Gln
                 85                  90                  95
Asp Trp Leu Asn Gly Lys Glu Tyr Lys Cys Lys Val Ser Asn Lys Gly
                100                 105                 110
Leu Pro Ser Ser Ile Glu Lys Thr Ile Ser Lys Ala Lys Gly Gln Pro
                115                 120                 125
Arg Glu Pro Gln Val Tyr Thr Leu Pro Pro Ser Gln Glu Glu Met Thr
130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
                180                 185                 190
Ser Arg Leu Thr Val Asp Lys Ser Arg Trp Gln Glu Gly Asn Val Phe
                195                 200                 205
Ser Cys Ser Val Met His Glu Ala Leu His Asn His Tyr Thr Gln Lys
210                 215                 220
Ser Leu Ser Leu Ser Leu Gly Lys
225                 230
```

<210> SEQ ID NO 2
<211> LENGTH: 235
<212> TYPE: PRT
<213> ORGANISM: Artificial sequence
<220> FEATURE:
<223> OTHER INFORMATION: Synthetic

<400> SEQUENCE: 2

```
Asp Lys Lys Val Glu Pro Lys Ser Cys Asp Lys Thr His Thr Cys Pro
  1               5                  10                  15
Pro Cys Pro Ala Pro Pro Val Ala Gly Pro Ser Val Phe Leu Phe Pro
                 20                  25                  30
Pro Lys Pro Lys Asp Thr Leu Met Ile Ser Arg Thr Pro Glu Val Thr
                 35                  40                  45
Cys Val Val Val Asp Val Ser Gln Glu Asp Pro Glu Val Gln Phe Asn
 50                  55                  60
Trp Tyr Val Asp Gly Val Glu Val His Asn Ala Lys Thr Lys Pro Arg
 65                  70                  75                  80
Glu Glu Gln Phe Asn Ser Thr Tyr Arg Val Val Ser Val Leu Thr Val
                 85                  90                  95
Leu His Gln Asp Trp Leu Asn Gly Lys Glu Tyr Lys Cys Lys Val Ser
                100                 105                 110
Asn Lys Gly Leu Pro Ser Ser Ile Glu Lys Thr Ile Ser Lys Ala Lys
                115                 120                 125
Gly Gln Pro Arg Glu Pro Gln Val Tyr Thr Leu Pro Pro Ser Arg Asp
130                 135                 140
Glu Leu Thr Lys Asn Gln Val Ser Leu Thr Cys Leu Val Lys Gly Phe
145                 150                 155                 160
Tyr Pro Ser Asp Ile Ala Val Glu Trp Glu Ser Asn Gly Gln Pro Glu
                165                 170                 175
```

```
Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

<210> SEQ ID NO 3
<211> LENGTH: 8
<212> TYPE: PRT
<213> ORGANISM: Homo sapiens

<400> SEQUENCE: 3

Pro Cys Pro Ala Pro Pro Val Ala
1               5

<210> SEQ ID NO 4
<211> LENGTH: 4
<212> TYPE: PRT
<213> ORGANISM: Homo sapiens

<400> SEQUENCE: 4

Asp Lys Lys Val
1

<210> SEQ ID NO 5
<211> LENGTH: 4
<212> TYPE: PRT
<213> ORGANISM: Homo sapiens

<400> SEQUENCE: 5

Asp Lys Arg Val
1

<210> SEQ ID NO 6
<211> LENGTH: 12
<212> TYPE: PRT
<213> ORGANISM: Homo sapiens

<400> SEQUENCE: 6

Glu Pro Lys Ser Cys Asp Lys Thr His Thr Cys Pro
1               5                   10

<210> SEQ ID NO 7
<211> LENGTH: 9
<212> TYPE: PRT
<213> ORGANISM: Homo sapiens

<400> SEQUENCE: 7

Glu Ser Lys Tyr Gly Pro Pro Cys Pro
1               5

<210> SEQ ID NO 8
<211> LENGTH: 20
<212> TYPE: PRT
<213> ORGANISM: Artificial sequence
<220> FEATURE:
<223> OTHER INFORMATION: Synthetic

<400> SEQUENCE: 8

Glu Pro Lys Ser Cys Asp Lys Thr His Thr Cys Pro Pro Cys Pro Ala
1               5                   10                  15
```

Pro Pro Val Ala
            20

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Glu Ser Lys Tyr Gly Pro Pro Cys Pro Pro Cys Pro Ala Pro Pro Val
1               5                   10                  15

Ala

<210> SEQ ID NO 10
<211> LENGTH: 104
<212> TYPE: PRT
<213> ORGANISM: Homo sapiens

<400> SEQUENCE: 10

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser Gln
            20                  25                  30

Glu Asp Pro Glu Val Gln Phe Asn Trp Tyr Val Asp Gly Val Glu Val
        35                  40                  45

His Asn Ala Lys Thr Lys Pro Arg Glu Glu Gln Phe Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Gly Leu Pro Ser Ser Ile
                85                  90                  95

Glu Lys Thr Ile Ser Lys Ala Lys
            100

<210> SEQ ID NO 11
<211> LENGTH: 107
<212> TYPE: PRT
<213> ORGANISM: Homo sapiens

<400> SEQUENCE: 11

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 12

```
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 326
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

```
          275                 280                 285
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 15
<211> LENGTH: 327
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Leu Gly Lys
            325

<210> SEQ ID NO 16
<211> LENGTH: 60
<212> TYPE: DNA
<213> ORGANISM: Artificial sequence
<220> FEATURE:
<223> OTHER INFORMATION: Synthetic

<400> SEQUENCE: 16
ttcgcgcagc ttaggtttat gccaggggggg acgggtggca cgggtcgtgg tggacaccgt     60

<210> SEQ ID NO 17
<211> LENGTH: 40
<212> TYPE: DNA
<213> ORGANISM: Artificial sequence
<220> FEATURE:
<223> OTHER INFORMATION: Synthetic

<400> SEQUENCE: 17
aagcttatac tcgagctcta gattgggaac ccgggtctct     40

<210> SEQ ID NO 18
<211> LENGTH: 58
<212> TYPE: DNA
<213> ORGANISM: Artificial sequence
<220> FEATURE:
<223> OTHER INFORMATION: Synthetic

<400> SEQUENCE: 18
cccaccgtgc ccagcaccac ctgtggcagg accatcagtc ttcctgttcc ccccaaaa     58

<210> SEQ ID NO 19
<211> LENGTH: 44
<212> TYPE: DNA
<213> ORGANISM: Artificial sequence
<220> FEATURE:
<223> OTHER INFORMATION: Synthetic

<400> SEQUENCE: 19
tgtgtcttca gggagaggga cagagaccca tttactcgcc ggcg     44

<210> SEQ ID NO 20
<211> LENGTH: 60
<212> TYPE: DNA
<213> ORGANISM: Artificial sequence
<220> FEATURE:
<223> OTHER INFORMATION: Synthetic

<400> SEQUENCE: 20
ctcgggttta gaacactgtt ttgagtgtgt acgggtggca cgggtcgtgg tggacaccgt     60

<210> SEQ ID NO 21
<211> LENGTH: 51
<212> TYPE: DNA
<213> ORGANISM: Artificial sequence
<220> FEATURE:
<223> OTHER INFORMATION: Synthetic

<400> SEQUENCE: 21
aaatcttgtg acaaaactca cacatgccca ccgtgcccag caccacctgt g     51

<210> SEQ ID NO 22
<211> LENGTH: 54
<212> TYPE: DNA

```
<213> ORGANISM: Artificial sequence
<220> FEATURE:
<223> OTHER INFORMATION: Synthetic

<400> SEQUENCE: 22
gagaaaacca tctccaaagc caaagggcag ccccgagaac cacaggtgta cacc          54

<210> SEQ ID NO 23
<211> LENGTH: 54
<212> TYPE: DNA
<213> ORGANISM: Artificial sequence
<220> FEATURE:
<223> OTHER INFORMATION: Synthetic

<400> SEQUENCE: 23
ctcttttggt agaggtttcg gtttcccgtc ggggctcttg gtgtccacat gtgg          54

<210> SEQ ID NO 24
<211> LENGTH: 39
<212> TYPE: DNA
<213> ORGANISM: Artificial sequence
<220> FEATURE:
<223> OTHER INFORMATION: Artificial

<400> SEQUENCE: 24 cttcaggag agggacagag gcccatttac tcgccggcg                            39

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
gctgacagac taacagactg                                                20

<210> SEQ ID NO 26
<211> LENGTH: 24
<212> TYPE: DNA
<213> ORGANISM: Artificial sequence
<220> FEATURE:
<223> OTHER INFORMATION: Synthetic

<400> SEQUENCE: 26
gacctcaggg gtccgggaga tcat                                           24

<210> SEQ ID NO 27
<211> LENGTH: 26
<212> TYPE: DNA
<213> ORGANISM: Artificial sequence
<220> FEATURE:
<223> OTHER INFORMATION: Synthetic

<400> SEQUENCE: 27
atacattata cgaagttata ccggta                                         26

<210> SEQ ID NO 28
<211> LENGTH: 990
<212> TYPE: DNA
<213> ORGANISM: Artificial sequence
<220> FEATURE:
<223> OTHER INFORMATION: Synthetic

<400> SEQUENCE: 28
gcctccacca agggcccatc ggtcttcccc ctggcaccct cctccaagag cacctctggg    60
```

```
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag caccacctgt ggcaggacca      360
tcagtcttcc tgttcccccc aaaacccaag gacactctca tgatctcccg gacccctgag      420
gtcacgtgcg tggtggtgga cgtgagccag gaagacccg aggtccagtt caactggtac      480
gtggatggcg tggaggtgca taatgccaag acaaagccgc gggaggagca gttcaacagc      540
acgtaccgtg tggtcagcgt cctcaccgtc ctgcaccagg actggctgaa cggcaaggag      600
tacaagtgca aggtctccaa caaaggcctc ccgtcctcca tcgagaaaac catctccaaa      660 gccaagggc agcccgaga ccacaggtg tacaccctgc cccatcccg ggatgagctg      720 accaagaacc aggtcagcct gacctgcctg gtcaaaggct tctatcccag cgacatcgcc      780
gtggagtggg agagcaatgg gcagccggag aacaactaca agaccacgcc tcccgtgctg      840
gactccgacg gctccttctt cctctacagc aagctcaccg tggacaagag caggtggcag      900
caggggaacg tcttctcatg ctccgtgatg catgaggctc tgcacaacca ctacacgcag      960
aagtccctct ccctgtctcc gggtaaatga                                       990

<210> SEQ ID NO 29
<211> LENGTH: 981
<212> TYPE: DNA
<213> ORGANISM: Artificial sequence
<220> FEATURE:
<223> OTHER INFORMATION: Synthetic

<400> SEQUENCE: 29
gccagcacaa aaggtcctag cgttttccca cttgccccat gttcaaggtc aacctccgaa       60
agtaccgccg ctcttggctg tctcgtaaaa gattattttc ccgaacctgt aactgtctcc      120
tggaactccg gcgcactcac ttccggcgta catccttcc ccgctgtcct ccaatcttcc      180
ggtctctact ccctgtcttc tgttgtcact gttccatcat cctcactcgg cacaaaaaca      240
tatacctgca acgttgatca caagccaagt aataccaaag ttgataagcg cgtcgaatcc      300
aaatacggtc ccccctgccc accgtgccca gcaccacctg tggcaggacc atcagtcttc      360
ctgttccccc caaaacccaa ggacactctc atgatctccc ggacccctga ggtcacgtgc      420
gtggtggtgg acgtgagcca ggaagacccc gaggtccagt tcaactggta cgtggatggc      480
gtggaggtgc ataatgccaa gacaaagccg cgggaggagc agttcaacag cacgtaccgt      540
gtggtcagcg tcctcaccgt cctgcaccag gactggctga acggcaagga gtacaagtgc      600
aaggtctcca acaaaggcct cccgtcctcc atcgagaaaa ccatctccaa agccaagggg      660
cagccccgag agccacaggt gtacaccctg cccccatccc aggaggagat gaccaagaac      720
caggtcagcc tgacctgcct ggtcaaaggc ttctacccca gcgacatcgc cgtggagtgg      780
gagagcaatg ggcagccgga gaacaactac aagaccacgc ctcccgtgct ggactccgac      840
ggctccttct tcctctacag caggctcacc gtggacaaga gcaggtggca ggaggggaat      900
gtcttctcat gctccgtgat gcatgaggct ctgcacaacc actacacaca gaagtccctc      960
tccctgtctc tgggtaaatg a                                                981

<210> SEQ ID NO 30
```

<211> LENGTH: 329
<212> TYPE: PRT
<213> ORGANISM: Artificial sequence
<220> FEATURE:
<223> OTHER INFORMATION: Synthetic

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 31
<211> LENGTH: 326
<212> TYPE: PRT
<213> ORGANISM: Artificial sequence
<220> FEATURE:
<223> OTHER INFORMATION: Synthetic

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 32
<211> LENGTH: 708
<212> TYPE: DNA
<213> ORGANISM: Artificial sequence
<220> FEATURE:
<223> OTHER INFORMATION: Synthetic

<400> SEQUENCE: 32
gacaagaaag ttgagcccaa atcttgtgac aaaactcaca catgcccacc gtgcccagca    60
ccacctgtgg caggaccatc agtcttcctg ttccccccaa acccaaggga cactctcatg   120

```
atctcccgga ccccctgaggt cacgtgcgtg gtggtggacg tgagccagga agaccccgag    180
gtccagttca actggtacgt ggatggcgtg gaggtgcata atgccaagac aaagccgcgg    240
gaggagcagt tcaacagcac gtaccgtgtg gtcagcgtcc tcaccgtcct gcaccaggac    300
tggctgaacg gcaaggagta caagtgcaag gtctccaaca aaggcctccc gtcctccatc    360
gagaaaacca tctccaaagc caagggcag ccccgagaac acaggtgta caccctgccc     420 ccatcccggg atgagctgac caagaaccag gtcagcctga cctgcctggt caaaggcttc    480
tatcccagcg acatcgccgt ggagtgggag agcaatgggc agccggagaa caactacaag    540
accacgcctc ccgtgctgga ctccgacggc tccttcttcc tctacagcaa gctcaccgtg    600
gacaagagca ggtggcagca ggggaacgtc ttctcatgct ccgtgatgca tgaggctctg    660
cacaaccact acacgcagaa gtccctctcc ctgtctccgg gtaaatga               708
```

```
<210> SEQ ID NO 33
<211> LENGTH: 699
<212> TYPE: DNA
<213> ORGANISM: Artificial sequence
<220> FEATURE:
<223> OTHER INFORMATION: Synthetic

<400> SEQUENCE: 33
gataagcgcg tcgaatccaa atacggtccc ccctgcccac cgtgcccagc accacctgtg     60
gcaggaccat cagtcttcct gttccccca aaacccaagg acactctcat gatctcccgg    120 accccctgagg tcacgtgcgt ggtggtggac gtgagccagg aagaccccga ggtccagttc    180
aactggtacg tggatggcgt ggaggtgcat aatgccaaga caaagccgcg ggaggagcag    240
ttcaacagca cgtaccgtgt ggtcagcgtc ctcaccgtcc tgcaccagga ctggctgaac    300
ggcaaggagt acaagtgcaa ggtctccaac aaaggcctcc cgtcctccat cgagaaaacc    360
atctccaaag ccaaagggca gccccgagag ccacaggtgt acaccctgcc cccatcccag    420
gaggagatga ccaagaacca ggtcagcctg acctgcctgg tcaaaggctt ctaccccagc    480
gacatcgccg tggagtggga gagcaatggg cagccggaga caactacaa gaccacgcct    540 cccgtgctgg actccgacgg ctccttcttc tctacagca ggctcaccgt ggacaagagc     600
aggtggcagg aggggaatgt cttctcatgc tccgtgatgc atgaggctct gcacaaccac    660
tacacacaga gtccctctc cctgtctctg ggtaaatga                            699
```

```
<210> SEQ ID NO 34
<211> LENGTH: 357
<212> TYPE: DNA
<213> ORGANISM: Artificial sequence
<220> FEATURE:
<223> OTHER INFORMATION: Synthetic

<400> SEQUENCE: 34
gacgtccaac tggtgcagtc agggctgaa gtgaaaaaac ctggggcctc agtgaaggtg      60
tcctgcaagg cttctggcta caccttact aggtacacga tgcactgggt aaggcaggca    120
cctggacagg gtctggaatg gattggatac attaatccta gccgtggtta tactaattac    180 gcagacagc tcaagggccg cttcacaatc actacagaca atccaccag cacagcctac    240 atggaactga gcagcctgcg ttctgaggac actgcaacct attactgtgc aagatattat    300
gatgatcatt actgccttga ctactggggc caaggcacca cggtcaccgt ctcctca      357
```

```
<210> SEQ ID NO 35
<211> LENGTH: 990
```

```
<212> TYPE: DNA
<213> ORGANISM: Artificial sequence
<220> FEATURE:
<223> OTHER INFORMATION: Synthetic

<400> SEQUENCE: 35
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag caccacctgt ggcaggacca     360
tcagtcttcc tgttcccccc aaaacccaag gacactctca tgatctcccg gacccctgag     420
gtcacgtgcg tggtggtgga cgtgagccag gaagaccccg aggtccagtt caactggtac     480
gtggatggcg tggaggtgca taatgccaag acaaagccgc gggaggagca gttcaacagc     540
acgtaccgtg tggtcagcgt cctcaccgtc ctgcaccagg actggctgaa cggcaaggag     600
tacaagtgca aggtctccaa caaaggcctc ccgtcctcca tcgagaaaac catctccaaa     660
gccaaagggc agccccgaga accacaggtg tacaccctgc ccccatcccg ggatgagctg     720
accaagaacc aggtcagcct gacctgcctg gtcaaaggct tctatcccag cgacatcgcc     780
gtggagtggg agagcaatgg gcagccggag aacaactaca agaccacgcc tcccgtgctg     840
gactccgacg gctccttctt cctctacagc aagctcaccg tggacaagag caggtggcag     900
caggggaacg tcttctcatg ctccgtgatg catgaggctc tgcacaacag attcacgcag     960
aagtccctct ccctgtctcc gggtaaatga                                      990

<210> SEQ ID NO 36
<211> LENGTH: 981
<212> TYPE: DNA
<213> ORGANISM: Artificial sequence
<220> FEATURE:
<223> OTHER INFORMATION: Synthetic

<400> SEQUENCE: 36
gccagcacaa aggtcctag cgttttttcca cttgccccat gttcaaggtc aacctccgaa      60
agtaccgccg ctcttggctg tctcgtaaaa gattattttc ccgaacctgt aactgtctcc     120
tggaactccg gcgcactcac ttccggcgta cataccttcc ccgctgtcct ccaatcttcc     180
ggtctctact ccctgtcttc tgttgtcact gttccatcat cctcactcgg cacaaaaaca     240
tatacctgca acgttgatca caagccaagt aataccaaag ttgataagcg cgtcgaatcc     300
aaatacggtc ccccctgccc accgtgccca gcaccacctg tggcaggacc atcagtcttc     360
ctgttccccc caaaacccaa ggacactctc atgatctccc ggacccctga ggtcacgtgc     420
gtggtggtgg acgtgagcca ggaagacccc gaggtccagt tcaactggta cgtggatggc     480
gtggaggtgc ataatgccaa gacaaagccg cgggaggagc agttcaacag cacgtaccgt     540
gtggtcagcg tcctcaccgt cctgcaccag gactggctga acggcaagga gtacaagtgc     600
aaggtctcca acaaaggcct cccgtcctcc atcgagaaaa ccatctccaa agccaaaggg     660
cagccccgag agccacaggt gtacaccctg cccccatccc aggaggagat gaccaagaac     720
caggtcagcc tgacctgcct ggtcaaaggc ttctacccca gcgacatcgc cgtggagtgg     780
gagagcaatg ggcagccgga gaacaactac aagaccacgc ctcccgtgct ggactccgac     840
```

```
ggctccttct tcctctacag caggctcacc gtggacaaga gcaggtggca ggagggaat      900 gtcttctcat gctccgtgat gcatgaggct ctgcacaaca gattcacaca gaagtccctc    960
tccctgtctc tgggtaaatg a                                              981
```

<210> SEQ ID NO 37
<211> LENGTH: 329
<212> TYPE: PRT
<213> ORGANISM: Artificial sequence
<220> FEATURE:
<223> OTHER INFORMATION: Synthetic

<400> SEQUENCE: 37

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn Arg Phe Thr Gln
305                 310                 315                 320

Lys Ser Leu Ser Leu Ser Pro Gly Lys
                325
```

<210> SEQ ID NO 38
<211> LENGTH: 326
<212> TYPE: PRT
<213> ORGANISM: Artificial sequence
<220> FEATURE:
<223> OTHER INFORMATION: Synthetic

<400> SEQUENCE: 38

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Leu Gly Lys
                325
```

<210> SEQ ID NO 39
<211> LENGTH: 41
<212> TYPE: DNA
<213> ORGANISM: Artificial sequence
<220> FEATURE:

<223> OTHER INFORMATION: Synthetic

<400> SEQUENCE: 39
gtgagcgctc ttcggcagac gtccaactgg tgcagtcagg g                    41

<210> SEQ ID NO 40
<211> LENGTH: 47
<212> TYPE: DNA
<213> ORGANISM: Artificial sequence
<220> FEATURE:
<223> OTHER INFORMATION: Synthetic

<400> SEQUENCE: 40
cagctagctc ttccggctga ggagacggtg accgtggtgc cttggcc              47

<210> SEQ ID NO 41
<211> LENGTH: 107
<212> TYPE: PRT
<213> ORGANISM: Artificial sequence
<220> FEATURE:
<223> OTHER INFORMATION: Synthetic

<400> SEQUENCE: 41

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 42
<211> LENGTH: 107
<212> TYPE: PRT
<213> ORGANISM: Artificial sequence
<220> FEATURE:
<223> OTHER INFORMATION: Synthetic

<400> SEQUENCE: 42

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Leu Gly Lys
            100                 105

```
<210> SEQ ID NO 43
<211> LENGTH: 98
<212> TYPE: PRT
<213> ORGANISM: Homo sapiens

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 44
<211> LENGTH: 98
<212> TYPE: PRT
<213> ORGANISM: Homo sapiens

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val
```

ANTIBODIES COMPRISING CHIMERIC CONSTANT DOMAINS

CROSS-REFERENCE TO RELATED APPLICATIONS

This application is a continuation of U.S. application Ser. No. 15/147,791, filed May 5, 2016, which is a division of U.S. application Ser. No. 14/170,166, filed Jan. 31, 2014, now U.S. Pat. No. 9,359,437, which claims the benefit under 35 U.S.C. § 119(e) of U.S. Provisional Application No. 61/759,578, filed 1 Feb. 2013, each of which is herein incorporated by reference.

SEQUENCE LISTING

This application incorporates by reference the Sequence Listing submitted in Computer Readable Form as file 8550U503-Sequence.txt, created on Sep. 12, 2018 and containing 43,593 bytes.

FIELD OF THE INVENTION

The present invention concerns antibodies or antigen-binding proteins engineered with recombinant polypeptides comprising a chimeric constant region, more specifically including a chimeric hinge region in the heavy chain constant region. The present invention relates to antibodies and antigen-binding proteins comprising such recombinant polypeptides that reduce effector functions and provide an advantage for use in therapy.

BACKGROUND OF THE INVENTION

Immunoglobulins of the IgG class are attractive as therapeutic agents. IgGs exists as four subclasses in humans, IgG1, IgG2, IgG3, and IgG4. The heavy chain constant ($C_H$) region of IgG comprises three domains, $C_H1$, $C_H2$, $C_H3$, where $C_H1$ and $C_H2$ are linked by a hinge. Although the role of each subclass appears to vary between species, it is known that the heavy chain constant domain is responsible for various biological effector functions. The human IgG subclasses mediate a plethora of cellular immune responses through their interaction with Fcγ receptors (FcγRs), such as cell killing, complement activation, phagocytosis and opsonization. In an attempt to understand and manipulate the effects of IgG subclass binding to FcγRs, researchers have made various mutations to the constant domains of IgGs and studied the resulting IgG/FcγR interaction (see e.g. Canfield and Morrison *J Exp Med* 73, 1483-1491 (1991); Chappel, M. S., et al. *JBC* 268(33), 25124-31 (1993); and Armour, K. L., et al. *Eur J Immunol* 29, 2613-24 (1999)).

Fc dependent cytotoxic activity of human IgG antibodies requires binding of the Fc region of the antibody (which consists of at least a functional CH2 and CH3 domain) to an FcγR on the surface of an effector cell, such as a natural killer cell, an activated macrophage or the like. Complement-mediated lysis can also be triggered by the interaction of the Fc region with various complement components. With regard to FcγR binding, it has been suggested that several amino acid residues in the hinge region and in the $C_H2$ domain of the antibody are important (see Sarmay, G, et al. *Mol Immunol* 29, 633-9 (1992); Greenwood, J et al., *Eur. J. Immunol*, 23(5), 1098 (1993), Morgan, A. et al, *Immunology*, 86, 319 (1995), Stevenson, G T, *Chemical Immunology*, 65, 57-72 (1997)). Glycosylation of a site (N297) in the CH2 domain and variations in the composition of its carbohydrates also strongly affect the IgG/FcγR interaction (Stevenson, G T, *Chemical Immunology*, 65, 57-72 (1997); Sibéril et al *Immunol Ltrs* 106, 111-118 (2006)).

For certain antibody therapies, it may be advantageous to engineer the Fc receptor binding properties so as to activate all, some, or none of the available effector mechanisms, without affecting the antibody's pharmacokinetic properties. The desired combination of therapeutic properties may not be available in the natural antibody repertoire. The design of antibodies with reduced effector function should be efficacious for example when the therapeutic objective is not to kill a target cell, but to block or activate a cell surface molecule on its surface without triggering cytotoxicity. Another setting in which reduced binding to Fc receptors could be desirable is when the antibody is bispecific, and its desired therapeutic properties arise from the different binding specificities. For example, a common usage of bispecific antibodies is to combine a tumor targeting specificity with a T cell activating specificity in order to trigger tumor-specific T cell killing. In this case, if the Fc portion binds to an Fc receptor, then potentially that could trigger undesirable killing of cells bearing Fc receptors by T cells, or killing of T cells by Fc receptor-bearing cells such as natural killer cells or macrophages.

Thus, there exists a need for improved biological therapies, such as antibodies with desirable properties for use in such therapies. Applicants have discovered that recombinant proteins containing substituted or otherwise modified antibody heavy chains, including recombinant antibodies and recombinant receptor-Fc fusion proteins, have altered Fc receptor binding activity, which reduce the risk of unwanted side effects, and thus provide improved therapeutic effect.

SUMMARY OF THE INVENTION

The antibodies, antigen-binding proteins and Fc-fusion proteins that are disclosed herein are engineered to have reduced binding to Fc receptors.

One aspect of the invention provides a recombinant polypeptide comprising a chimeric Fc region, wherein the Fc region comprises a chimeric hinge comprising the amino acid sequence EPKSCDKTHTCPPCPAPPVA (SEQ ID NO: 8). The invention also provides a recombinant polypeptide comprising a chimeric Fc region, wherein the Fc region comprises a chimeric hinge comprising the amino acid sequence ESKYGPPCPPCPAPPVA (SEQ ID NO: 9).

Another aspect of the invention provides a recombinant polypeptide comprising a chimeric Fc region, wherein the Fc region comprises a chimeric hinge comprising the amino acid sequence EPKSCDKTHTCPPCPAPPVA (SEQ ID NO: 8) linked to an IgG4 CH2 region. Still another aspect of the invention provides a recombinant polypeptide comprising a chimeric Fc region, wherein the Fc region comprises a chimeric hinge comprising the amino acid sequence ESKYGPPCPPCPAPPVA (SEQ ID NO: 9) linked to an IgG4 CH2 region.

In some embodiments, the recombinant polypeptide comprises a chimeric Fc region, wherein the Fc region comprises an IgG1 or IgG4 CH3 region, or a variant thereof. In other embodiments, the recombinant polypeptide comprises a chimeric Fc region, wherein the Fc region binds to FcγRIIA. In other aspects the recombinant polypeptide comprises a chimeric Fc region, wherein the Fc region binds to FcγRIIA and FcγRIIB.

In other embodiments, the invention provides a recombinant polypeptide comprising a chimeric Fc region, wherein the Fc region comprises chimeric hinge comprising an amino acid sequence EPKSCDKTHTCPPCPAPPVA (SEQ ID NO: 8) and the recombinant polypeptide binds to FcγRIIA.

In still other aspects, the invention provides a recombinant polypeptide comprising a chimeric Fc region, wherein the Fc region comprises a chimeric hinge comprising an amino acid sequence ESKYGPPCPPCPAPPVA (SEQ ID NO: 9) and the recombinant polypeptide binds to FcγRIIA.

A further aspect of the invention provides a recombinant polypeptide comprising a heavy chain constant (CH) region comprising, from N-terminus to C-terminus, a CH1 domain, a chimeric hinge, a CH2 domain, and a CH3 domain wherein the CH1 domain comprises a human IgG1 CH1 or a human IgG4 CH1 having at least the amino acid sequence DKKV or DKRV from positions 212 to 215 (EU numbering), the chimeric hinge comprises a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering), the CH2 domain comprises a human IgG4 CH2 domain amino acid sequence from positions 237 to 340 (EU numbering), and the CH3 domain comprises a human IgG1 or a human IgG4 CH3 domain sequence from positions 341 to 447 (EU numbering), or a variant thereof.

Some embodiments of the invention provide a recombinant polypeptide wherein the CH1 domain comprises a human IgG1 CH1 amino acid sequence (SEQ ID NO: 43), and the chimeric hinge comprises the amino acid sequence EPKSCDKTHTCPPCPAPPVA (SEQ ID NO: 8). Still another embodiment of the invention provides a recombinant polypeptide wherein the CH1 domain comprises a human IgG4 CH1 amino acid sequence (SEQ ID NO: 44), and the chimeric hinge comprises the amino acid sequence ESKYGPPCPPCPAPPVA (SEQ ID NO: 9).

Another embodiment of the invention provides a recombinant polypeptide wherein the CH1 domain comprises the amino acid sequence DKKV (SEQ ID NO: 4), and the chimeric hinge comprises the amino acid sequence EPKSCDKTHTCPPCPAPPVA (SEQ ID NO: 8). Still another embodiment of the invention provides a recombinant polypeptide wherein the CH1 domain comprises the amino acid sequence DKRV (SEQ ID NO: 5), and the chimeric hinge comprises the amino acid sequence ESKYGPPCPPCPAPPVA (SEQ ID NO: 9). In another aspect, the CH1 domain comprises a variant of SEQ ID NO: 43 or 44.

Another embodiment of the invention provides a recombinant polypeptide wherein the CH2 domain comprises the amino acid sequence SEQ ID NO: 10. Yet another embodiment of the invention provides a recombinant polypeptide wherein the CH3 domain comprises the amino acid sequence SEQ ID NO: 11 or SEQ ID NO: 12. In another aspect, the CH3 domain comprises SEQ ID NO: 41 or 42.

An aspect of the invention provides a recombinant polypeptide, wherein the polypeptide comprises N'-VD1-X1$_n$-Y1-Y2-X2-X3-C', wherein:

N' is the N-terminus and C' is the C-terminus of the polypeptide,

VD1 is an amino acid sequence comprising an antigen-binding domain,

X1 is an amino acid sequence comprising a domain selected from the group consisting of an IgG1 CH1 domain or a variant thereof, an IgG4 CH1 domain or a variant thereof, and at least positions 212-215 (EU numbering) of an IgG1 or IgG4 CH1 domain, Y1 comprises an amino acid sequence from positions 216-227 (EU numbering) of an IgG1 or IgG4 hinge region, Y2 comprises the human IgG2 lower hinge region amino acid sequence PCPAPPVA (SEQ ID NO: 3) from positions 228 to 236 (EU numbering), X2 is an amino acid sequence comprising an IgG4 CH2 domain, or a variant thereof, and X3 is an amino acid sequence comprising an IgG1 CH3 domain or an IgG4 CH3 domain, or a variant thereof; wherein n=0 or 1.

In some embodiments of the invention, n=1. In yet another embodiment of the invention, X1 comprises the amino acid sequence DKKV (SEQ ID NO: 4), and Y1-Y2 comprises a chimeric hinge consisting of the amino acid sequence EPKSCDKTHTCPPCPAPPVA (SEQ ID NO: 8). In still another embodiment of the invention, X1 comprises the amino acid sequence DKRV (SEQ ID NO: 5), and Y1-Y2 comprises a chimeric hinge consisting of the amino acid sequence ESKYGPPCPPCPAPPVA (SEQ ID NO: 9). In one more embodiment, X1 comprises SEQ ID NO 43 or SEQ ID NO: 44. In another aspect of the invention, X2 comprises SEQ ID NO: 10. In another embodiment of the invention, X3 comprises SEQ ID NO: 11 or SEQ ID NO: 12. In yet another embodiment, X3 comprises SEQ ID NO: 41 or SEQ ID NO: 42.

Another aspect of the invention provides a recombinant polypeptide wherein the heavy chain constant region (CH) region comprises an amino acid sequence at least 99% identical to any one of SEQ ID NO: 1, SEQ ID NO: 2, SEQ ID NO: 30, SEQ ID NO: 31, SEQ ID NO: 37 or SEQ ID NO: 38.

In some embodiments, n=0 and Y1-Y2 comprises a chimeric hinge having the amino acid sequence EPKSCDKTHTCPPCPAPPVA (SEQ ID NO: 8). In other embodiments, n=0 and Y1-Y2 comprises a chimeric hinge having the amino acid sequence ESKYGPPCPPCPAPPVA (SEQ ID NO: 9).

In another embodiment of the invention, the recombinant polypeptide is an antigen-binding protein. In another embodiment, the recombinant polypeptide is a Fc-fusion protein, such as a receptor-Fc fusion protein. In yet another embodiment of the invention, the recombinant polypeptide is an antibody.

A further aspect of the invention provides a recombinant polypeptide, antigen-binding protein, Fc-fusion protein or antibody that exhibits decreased effector functions when compared to a corresponding recombinant polypeptide, antigen-binding protein, Fc-fusion protein or antibody comprising the wild-type IgG1 or IgG4 heavy chain constant region, at a concentration of at least 10 nM. The invention thus provides a recombinant polypeptide, antigen-binding protein, Fc-fusion protein or antibody having decreased binding, cytotoxic activity, and cellular proliferation.

The invention further provides a recombinant polypeptide, antigen-binding protein, Fc-fusion protein or antibody that exhibits cytotoxic activity of less than about 50%, at a concentration of at least 10 nM or at least 100 nM. The invention also provides a recombinant polypeptide, antigen-binding protein, Fc-fusion protein or antibody that exhibits cytotoxic activity of less than about 40%, or less than about 30%, or less than about 20%, or less than about 10%, or less than about 5%, or even undetectable, at a concentration of at least 10 nM or at least 100 nM.

In other embodiments, the recombinant polypeptide, antigen-binding protein, Fc-fusion protein or antibody exhibits CDC activity of less than about 50% cytotoxicity, or less than 40%, 30%, 20%, 10%, or 5%, 4%, 3%, 2%, or even 0% or undetectable cytotoxicity, as measured in an in vitro or ex vivo cell killing assay. In certain embodiments, CDC activity is less than 50%, 40%, 30%, 20%, 10%, or 5%, 4%, 3%, 2%, or even 0% or undetectable, at a concentration of 100 nM. In more embodiments, the recombinant polypeptide, antigen-binding protein, Fc-fusion protein or antibody exhibits ADCC activity of less than about 50% cytotoxicity, or less than cytotoxicity 40%, 30%, 20%, 10%, or 5%, 4%, 3%, 2%, or even 0% or undetectable cytotoxicity, as measured in an in vitro or ex vivo cell killing assay. In certain embodiments, ADCC activity is less than 50%, 40%, 30%, 20%, 10%, or 5%, 4%, 3%, 2%, or even 0% or undetectable ADCC activity, at a concentration of 100 nM.

In still other embodiments, the recombinant polypeptide, antigen-binding protein, Fc-fusion protein or antibody exhibits ADCP activity of less than about 50% ADCP activity, or less than 40%, 30%, 20%, 10%, or 5%, 4%, 3%, 2%, or even 0% or undetectable ADCP activity, as measured in an in vitro or ex vivo cellular phagocytosis assay. In certain embodiments, ADCP activity is less than 50%, 40%, 30%, 20%, 10%, or 5%, 4%, 3%, 2%, or even 0% or undetectable ADCP activity, at a concentration of 100 nM.

The invention further provides a recombinant polypeptide wherein the cytotoxic activity is at least about 10-fold less than the cytotoxic activity of a corresponding polypeptide comprising a wild-type IgG1 or wild-type IgG4 heavy chain constant region. The invention also provides a recombinant polypeptide wherein the cytotoxic activity is at least about 10-fold less, about 20-filed less, about 50-fold less, or about 100-fold less, or about 1000-fold less than the cytotoxic activity of a corresponding polypeptide comprising a wild-type IgG1 or wild-type IgG4 heavy chain constant region.

An aspect of the invention provides a composition comprising the recombinant polypeptide.

Another aspect of the invention provides a nucleic acid molecule encoding any one of the recombinant polypeptides of the invention. The invention further provides a nucleic acid molecule encoding a recombinant polypeptide of the invention, wherein the recombinant polypeptide comprises an amino acid sequence selected from the group consisting of SEQ ID NO: 1, SEQ ID NO: 2, SEQ ID NO: 30, SEQ ID NO: 31, SEQ ID NO: 38 and SEQ ID NO: 37.

The invention further provides a nucleic acid molecule comprising a nucleotide sequence having greater than 99% sequence identity to SEQ ID NO: 28, SEQ ID NO: 29, SEQ ID NO: 32, or SEQ ID NO: 33. The invention also provides a nucleic acid molecule comprising a nucleotide sequence having greater than 99% sequence identity to SEQ ID NO: 36 or SEQ ID NO: 35.

The invention also provides a nucleic acid molecule comprising a nucleotide sequence selected the group consisting of SEQ ID NO: 28, SEQ ID NO: 29, SEQ ID NO: 32, SEQ ID NO: 33, SEQ ID NO: 36 and SEQ ID NO: 35.

An aspect of the invention provides a vector comprising any one of the nucleic acid molecules of the invention. The invention further provides a vector wherein the nucleic acid molecule of the invention is operatively linked to an expression control sequence suitable for expression in a host cell. The invention also provides a vector of the invention wherein the expression control sequence comprises a promoter selected from the group consisting of SV40, CMV, CMV-IE, CMV-MIE, UbC, RSV, SL3-3, MMTV, Ubi and HIV LTR. The invention further provides a vector of the invention wherein the promoter is a CMV-MIE/TetO or CMV-MIE/Arc hybrid promoter. The invention also provides a vector of the invention comprising one or more selectable marker genes selected from the group consisting of bla, bls, BSD, bsr, Sh ble, hpt, tetR, tetM, npt, kanR and pac.

Another aspect of the invention provides a cell comprising a nucleic acid of the invention. The invention further provides a cell comprising a vector of the invention.

The invention further provides a cell comprising a nucleic acid of the invention, wherein the nucleic acid is integrated into the genome of the cell. The invention also provides a cell comprising a nucleic acid encoding a protein expression enhancer. The invention still further provides a cell comprising a nucleic acid encoding an XBP polypeptide.

In an embodiment of the invention, the cell is a eukaryotic cell. In an embodiment of the invention, the cell is an animal cell. In an embodiment of the invention, the cell is a mammalian cell. In another embodiment of the invention, the cell is a CHO cell. In an embodiment of the invention, the cell is a CHO-K1 cell.

An aspect of the invention provides a method of making an antibody comprising a chimeric hinge region, said method comprising:

(a) transfecting a host cell with a nucleic acid molecule encoding the light chain of said antibody, said nucleic acid molecule comprising a nucleotide sequence encoding the $V_L$ region of a selected antigen-specific antibody and a nucleotide sequence encoding the constant $C_L$ region of an Ig, wherein said nucleotide sequence encoding the $V_L$ region of a selected antigen-specific antibody and said nucleotide sequence encoding the $C_L$ region of an Ig are operably linked together; (b) transfecting the host cell of step (a) with a nucleic acid molecule encoding the heavy chain of said antibody, said nucleic acid molecule comprising a nucleotide sequence encoding the $V_H$ region of a selected antigen-specific antibody and a nucleotide sequence encoding a constant $C_H$ region of a human Ig, wherein the nucleotide sequence encoding the $C_H$ region comprises the nucleotide sequence encoding SEQ ID NO: 1, SEQ ID NO: 2, SEQ ID NO: 30, SEQ ID NO: 31, SEQ ID NO: 38 or SEQ ID NO: 37, wherein said nucleotide sequence encoding the $V_H$ region of a selected antigen-specific antibody and said nucleotide sequence encoding the $C_H$ region of said Ig are operably linked together; and (c) making said antibody by co-expressing the nucleic acid molecules of (a) and (b) in said host cell.

A method of making an antibody comprising a chimeric hinge region, said method comprising:

(a) transfecting a host cell with a nucleic acid molecule encoding the light chain of said antibody, said nucleic acid molecule comprising a nucleotide sequence encoding the VL region of a selected antigen-specific antibody and a nucleotide sequence encoding the constant CL region of an Ig, wherein said nucleotide sequence encoding the VL region of a selected antigen-specific antibody and said nucleotide sequence encoding the CL region of an Ig are operably linked together; (b) transfecting the host cell of step (a) with a nucleic acid molecule encoding the heavy chain of said antibody, said nucleic acid molecule comprising a nucleotide sequence encoding the $V_H$ region of a selected antigen-specific antibody and a nucleotide sequence encoding a constant CH region of a human Ig, wherein the nucleotide sequence encoding the CH region comprises the chimeric hinge nucleotide sequence encoding SEQ ID NO: 8 or SEQ ID NO: 9, wherein said nucleotide sequence encoding the VH region of a selected antigen-specific antibody and said nucleotide sequence encoding the CH region of said Ig are operably linked together; and (c) making said antibody by co-expressing the nucleic acid molecules of (a) and (b) in said host cell.

In another aspect of the invention, the method of making an antibody further comprises the steps of culturing the host cell of step (b) hereinabove, wherein the antibody is secreted into a cell culture medium; and isolating the antibody from the cell culture media.

An aspect of the invention provides a method of making a receptor-Fc fusion protein comprising a chimeric hinge region, said method comprising:
(a) transfecting a host cell with a nucleic acid molecule encoding said receptor-Fc fusion protein, said nucleic acid molecule comprising a nucleotide sequence encoding a receptor protein, fused to a nucleotide sequence encoding a constant $C_H$ region of a human Ig, wherein the nucleotide sequence encoding the $C_H$ region comprises the nucleotide sequence encoding SEQ ID NO: 1, SEQ ID NO: 2, SEQ ID NO: 30, SEQ ID NO: 31, SEQ ID NO: 38 or SEQ ID NO: 37, wherein said nucleotide sequence encoding the receptor protein and said nucleotide sequence encoding the $C_H$ region of said Ig are operably linked together; and (b) making said receptor-Fc fusion protein by expressing the nucleic acid molecule of (a) in said host cell.

In another aspect of the invention, the method of making a receptor-Fc fusion comprises the steps of culturing the host cell of step (b) hereinabove, wherein the receptor-Fc fusion protein is secreted into a cell culture medium; and isolating the receptor-Fc fusion protein from the cell culture media.

An aspect of the invention provides a method of making a receptor-Fc fusion protein comprising a chimeric hinge region, said method comprising:
(a) transfecting a host cell with a nucleic acid molecule encoding said receptor-Fc fusion protein, said nucleic acid molecule comprising a nucleotide sequence encoding a receptor protein, fused to a nucleotide sequence encoding a constant CH region of a human Ig, wherein the nucleotide sequence encoding the CH region comprises the chimeric hinge nucleotide sequence encoding SEQ ID NO: 8 or SEQ ID NO: 9, wherein said nucleotide sequence encoding the receptor protein and said nucleotide sequence encoding the CH region of said Ig are operably linked together; and (b) making said receptor-Fc fusion protein by expressing the nucleic acid molecule of (a) in said host cell.

In other embodiments, the method of making an antibody comprises:
(a) producing a first cell culture comprising cells expressing a first heavy chain polypeptide of interest;
(b) producing a second cell culture comprising cells expressing a second heavy chain polypeptide of interest;
(c) combining the first and second cell culture, or the supernatants thereof; and
(d) recovering the first and second polypeptides in heterodimeric form; wherein the heavy chains of the first and second heavy chain polypeptides each comprise an amino acid sequence selected from the group consisting of SEQ ID NO: 1, SEQ ID NO: 2, SEQ ID NO: 30, SEQ ID NO: 31, SEQ ID NO: 38 and SEQ ID NO: 37. In the above methods, the first cell culture further comprises a first cognate light chain of interest and the second cell culture further comprises a second cognate light chain of interest, wherein the first and second cognate light chains are covalently bound to the first and second heavy chain polypeptides and are thus recovered. In other embodiments of the above methods, the heavy chains of the first and second heavy chain polypeptides each comprise a chimeric hinge amino acid sequence selected from the group consisting of SEQ ID NO: 8 and SEQ ID NO: 9.

In other embodiments, the invention provides a method of making an antibody comprising a first single chain variable fragment-Fc (scFv-Fc) produced in a first cell culture, and a second scFv-Fc produced in a second cell culture, wherein the Fc of the first and second scFv-Fc each comprise an amino acid sequence selected from the group consisting of SEQ ID NO: 1, SEQ ID NO: 2, SEQ ID NO: 30, SEQ ID NO: 31, SEQ ID NO: 38 and SEQ ID NO: 37, combining the first and second cell cultures or the supernatants thereof, and recovering or isolating the first and second scFv-Fc in heterodimeric form. In some embodiments, the first and second scFv-Fc are secreted into the cell culture medium (e.g. supernatant), and the method comprises combining the first and second cell culture media, and recovering or isolating the heterodimeric protein. In some embodiments of the above methods, the Fc of the first and second scFv-Fc each comprises a chimeric hinge amino acid sequence selected from the group consisting of SEQ ID NO: 8 and SEQ ID NO: 9.

In some embodiments of the invention, the host cell is selected from the group consisting of CHO, COS, retinal cell, Vero, CV1, 293, MDCK, HaK, BHK, HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, a cell line derived from any of the aforementioned cells, and a PER.C6® cell.

Another aspect of the invention provides a bispecific antibody comprising:
(a) a first heavy chain comprising an antigen-binding domain capable of recognizing and binding to a first target antigen, (b) a second heavy chain comprising an antigen-binding domain capable of recognizing and binding to a second target antigen, and (c) a common light chain antigen-binding domain capable of recognizing and binding to the first or second target antigen, wherein the heavy chain of (a) or (b) or both (a) and (b) comprises the heavy chain constant region comprising the amino acid sequence of SEQ ID NO: 1, SEQ ID NO:2, SEQ ID NO: 30, or SEQ ID NO: 31, or wherein the heavy chain of (a) or (b) or both (a) and (b) comprises the chimeric hinge region comprising the amino acid sequence of SEQ ID NO: 8 or SEQ ID NO: 9.

A further aspect of the invention provides a bispecific antibody of the invention comprising:(a) a first heavy chain comprising a first heavy chain constant region comprising SEQ ID NO: 1, SEQ ID NO:2, SEQ ID NO: 30, or SEQ ID NO: 31, and (b) a second heavy chain comprising a second heavy chain constant region comprising SEQ ID NO: 38 or SEQ ID NO: 37.

These and other objects, along with advantages and features of the invention disclosed herein, will be made more apparent from the description, drawings, and claims that follow.

BRIEF DESCRIPTION OF DRAWINGS

FIG. 1 shows the corresponding amino acid numbering conventions for the hinge region of hIgG1, hIgG2 and hIgG4. Amino acid numbering is according to the most recently updated IMGT Scientific Chart (IMGT®, the international ImMunoGeneTics information system®, http://www.imgt.org/IMGTScientificChart/Numbering/Hu_IGHGnber.html (created: 17 May 2001, last updated: 10 Jan. 2013) and the EU index as reported in Kabat, E. A. et al. Sequences of Proteins of Immunological interest. 5$^{th}$ ed. US Department of Health and Human Services, NIH publication No. 91-3242 (1991). (wt=wild-type; —means no corresponding number was reported for the particular reference; —means that no corresponding amino acid was reported in that position for the particular reference.)

FIG. 2 illustrates hinge amino acids used in the construction of chimeric hinge regions and the corresponding amino acid conventions.

FIG. 3. Amino acid sequence of the human IgG1 heavy chain constant region including CH1, hinge, CH2 and CH3 domains as described as IGHG1 in UniProtKB/Swiss-Prot Accn. No. P01857 (SEQ ID NO:13).

FIG. 4. Amino acid sequence of the human IgG2 heavy chain constant region including CH1, hinge, CH2 and CH3 domains as described as IGHG2 in UniProtKB/Swiss-Prot Accn. No. P01859 (SEQ ID NO:14).

FIG. 5. Amino acid sequence of the human IgG4 heavy chain constant region including CH1, hinge, CH2 and CH3 domains as described as IGHG4 in UniProtKB/Swiss-Prot Accn. No. P01861 (SEQ ID NO:15).

FIG. 6A: Background fluorescence was measured for control assays, i.e. Jurkat cells incubated with secondary antibody only (sec) and unstained Jurkat cells. FIG. 6B: Comparison of Jurkat cell binding to antibody containing a chimeric hinge heavy chain constant region (Ab 1=sIgG4) vs. binding to antibody containing a corresponding antigen-binding domain and a wild-type (wt) IgG4 constant region (Control Ab 2). FIG. 6C: Comparison of Jurkat cell binding to antibody containing a chimeric hinge heavy chain constant region (Ab 2=sIgG1) vs. binding to antibody containing a corresponding antigen-binding domain and a wild-type (wt) IgG1 heavy chain constant region (Control Ab 1).

DETAILED DESCRIPTION OF THE INVENTION

Figure 6A:
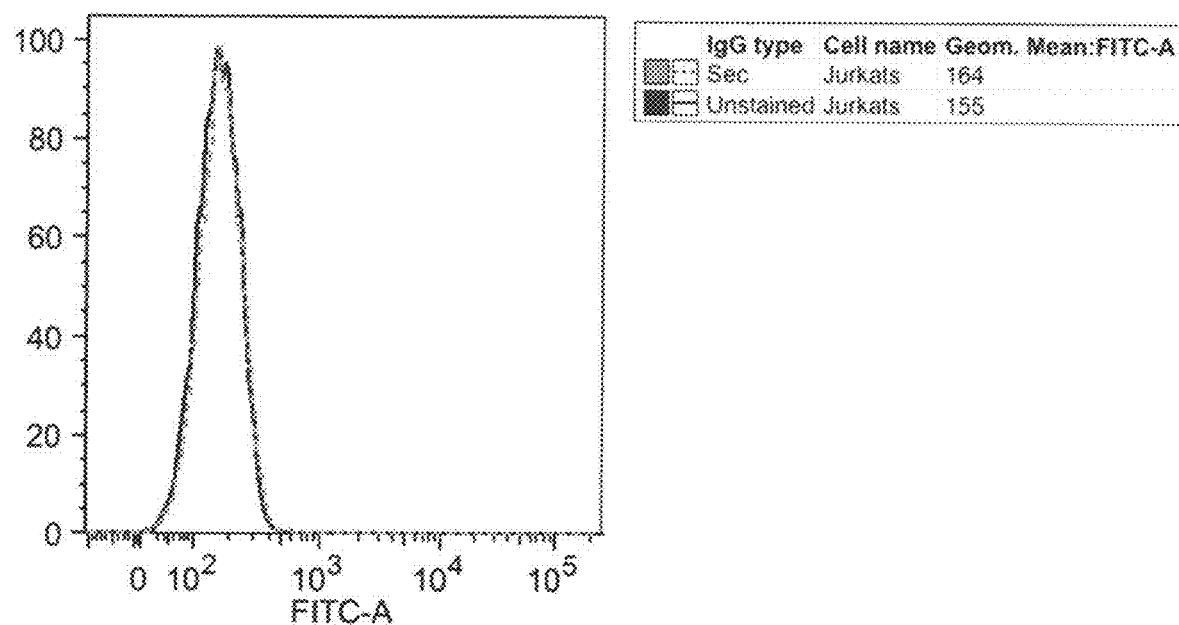
FIGS. 6A, 6B and 6C. Single-parameter histograms showing antibody binding (% of Max) to antigen on Jurkat cells in a fluorescent binding assay.

It is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice of the present invention, particular methods and materials are now described. All publications mentioned herein are incorporated herein by reference in their entirety.

The term "immunoglobulin" refers to a class of structurally related glycoproteins consisting of two pairs of polypeptide chains, one pair of light (L) chains and one pair of heavy (H) chains, which may all four be inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically comprises a heavy chain variable region (abbreviated herein as $V_H$ or VH) and a heavy chain constant region ($C_H$ or CH). The "heavy chain constant region", as used herein, typically comprises three domains, $C_H1$, $C_H2$, and $C_H3$, whereas the $C_H1$ and $C_H2$ domains are linked by a hinge, or a functional fragment thereof. Each light chain typically comprises a light chain variable region (abbreviated herein as $V_L$ or VL) and a light chain constant region. There are two types of light chains in humans, and other mammals: kappa (κ) chain and lambda (λ) chain. The light chain constant region typically comprises one domain ($C_L$). The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus (N-terminus) to carboxy-terminus (C-terminus) in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is according to IMGT, Sequences of Proteins of Immunological Interest, 5th Ed. Public Health Service, National Institutes of Health, Bethesda, Md. (1991), or by the EU numbering system of Kabat (also known as "EU numbering" or "EU index"), e.g., as in Kabat, E. A. et al. Sequences of Proteins of Immunological interest. 5$^{th}$ ed. US Department of Health and Human Services, NIH publication No. 91-3242 (1991).

The term "antibody" (Ab) as used herein, refers to an immunoglobulin molecule, or a derivative thereof, which has the ability to specifically bind to an antigen. The variable regions of the heavy and light chains of the immunoglobulin molecule contain a binding domain that interacts with an antigen as outlined above under "immunoglobulin". An antibody may also be a bispecific antibody, diabody, or similar molecule (see for instance PNAS USA 90(14), 6444-8 (1993) for a description of diabodies). Further, it has been shown that the antigen-binding function of an antibody may be performed by fragments of a full-length antibody, i.e. "antigen-binding fragments" or "antigen-binding proteins". As with full antibody molecules, antigen-binding proteins may be monospecific or multispecific (e.g., bispecific). Examples of binding molecules or fragments encompassed within the term "antibody" include, but are not limited to (i) a Fab' or Fab fragment, a monovalent fragment consisting of the $V_L$, $V_H$, $C_L$ and $C_H1$ domains, or a monovalent antibody as described in the international patent publication number WO2007059782; (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of a $V_L$ and $V_H$ domains, (v) a dAb fragment (Ward et al., Nature 341, 544-546 (1989)), which consists essentially of a $V_H$ domain and also called domain antibodies (Holt et al; Trends Biotechnol. 2003 November;21(11):484-90); (vi) camelid or nanobodies (Revets et al; Expert Opin Biol Ther. 2005 January;5 (1):111-24) and (vii) an isolated complementarity determining region (CDR).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or during gene rearrangement or by somatic mutation in vivo).

A multispecific antigen-binding fragment of an antibody (e.g., a bispecific antibody) will typically comprise at least two different variable domains, wherein each variable domain is capable of specifically binding to a separate antigen or to a different epitope on the same antigen. Any multispecific antibody format, including bispecific antibody formats disclosed herein, may be adapted for use in the context of an antigen-binding fragment of an antibody of the present invention using routine techniques available in the art.

Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term "antibody" unless otherwise noted or clearly indicated by context. Although such polypeptides are generally included within the meaning of antibody, they collectively, and each independently, are unique features of the present invention, exhibiting different biological properties and utility. These and other antibody fragments and recombinant polypeptides that are useful in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, and any antibody fragments retaining the ability to specifically bind to the antigen (antigen-binding fragments or molecules) provided by any known technique, such as enzymatic cleavage, peptide synthesis, and recombinant techniques. An antibody as generated can possess any Ig isotype or combination thereof. Any scFv may be fused to the heavy chain constant regions of the invention by known techniques.

Other exemplary bispecific formats that can be used in the context of the present invention include, without limitation, e.g., scFv-based bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, dual acting Fab (DAF)-IgG, and Mab2 bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al. 2013, J. Am. Chem. Soc. 9;135(1):340-6 [Epub: Dec. 21, 2012]).

Further exemplary multispecific formats can be used in the context of the present invention include, without limitation, e.g., involving a first antigen-binding domain that specifically binds a target molecule, and a second antigen-binding domain that specifically binds an internalizing effector protein, wherein such second antigen-binding domains are capable of activating and internalizing the effector protein, e.g. a receptor. (See U.S. Application Publication. No. 2013/0243775A1, published on Sep. 19, 2013, which is incorporated by reference.)

Recombinant proteins may be produced by standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, N.Y.).

The phrase "complementarity determining regions" or the term "CDR," includes an amino acid sequence encoded by a nucleic acid sequence of an organism's immunoglobulin (Ig) genes. CDRs are regions of hypervariability that are normally (i.e., in the context of a wild-type animal) interspersed within the more conserved framework regions (FRs) in a variable region of a light chain or a heavy chain of e.g., an antibody or a T cell receptor (TCR). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "antigen-binding domain", as used herein, is the amino acid sequence of a heavy chain or light chain capable of selectively recognizing and binding to antigen with a $K_D$ at least in the micromolar range. The antigen-binding domain of the invention includes at least one CDR.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

The phrase "heavy chain" or "immunoglobulin (Ig) heavy chain", as used herein, includes Ig heavy chain constant region sequence from any organism, and unless otherwise specified includes a heavy chain variable domain. Heavy chain variable domains include three heavy chain CDRs and four FR regions, unless otherwise specified. Fragments of heavy chain variable domains include CDRs, or both CDRs and FRs. A typical heavy chain constant region has, following the variable domain (from N-terminal to C-terminal), a CH1 domain, a hinge, a CH2 domain, and a CH3 domain. A functional fragment of a heavy chain in an antigen-binding protein includes a fragment that is capable of specifically recognizing an antigen (e.g., recognizing the antigen with a $K_D$ in the micromolar, nanomolar, or picomolar range), that is capable of being expressed in and secreted from a cell, and that comprises at least one CDR. For the purposes of this invention, a functional fragment of a heavy chain constant region includes at least an Fc domain or fragment thereof.

The phrase "Fc-containing protein" includes antibodies, bispecific antibodies, antibody-binding fragments, trap molecules and other receptor-Fc fusion proteins, and other binding proteins that comprise at least a functional portion of an immunoglobulin CH2 and CH3 region, such as ligand-Fc fusion proteins. A "functional portion" refers to a CH2 and CH3 region that can bind an Fc receptor e.g., an FcγR, (namely FcγRI (CD64), FcγRIIa (CD32a), FcγRIIb (CD32b), FcγRIIIa (CD16a), or FcγRIIIb (CD16b)) or FcRn, (the neonatal Fc receptor, which confers to antibodies their extended half-life). If the CH2 and CH3 region contains deletions, substitutions, and/or insertions or other modifications that render it unable to bind any Fc receptor, then the CH2 and CH3 region is considered to be non-functional. As such, when diminishing or eliminating certain effector functions is desired, any Fc-containing protein may be engineered to comprise a chimeric heavy chain constant region or fragment as described herein.

The phrase "Fc-fusion proteins", and specifically "receptor-Fc fusion proteins" includes recombinant proteins engineered to contain a functional Fc fragment as described herein. For example a "receptor-Fc fusion protein" includes a chimeric protein comprising an amino acid sequence of a receptor protein fused to an amino acid sequence of an Fc domain of Ig. Examples of receptor proteins used in fusion proteins are known in the art (see e.g. Klinkert, et al. *J Neuroimmunol.* 72(2):163-8 (1997); Milligan, G., et al. *Curr Pharm Des.* 10(17):1989-2001 (2004); and Schwache D, and Müller-Newen G, *Eur J Cell Biol.* 91(6-7):428-34 (2012), doi: 10.1016/j.ejcb.2011.07.008. Epub 2011 Sep. 29).

In the context of the present invention, receptor-Fc fusion proteins are encoded by a nucleotide sequence encoding a receptor protein fused to a nucleotide sequence of a chimeric heavy chain constant region as described herein. In some embodiments, the nucleotide sequence of the receptor protein encodes for the ligand-binding domain or the extracellular domain of the receptor. In other embodiments, the nucleotide sequence of the receptor protein encodes for the extracellular domain of the receptor and the transmembrane domain of the receptor. Receptor-Fc fusion proteins are also exemplified in US20090137416 A1.

Flow cytometry-based autologous secretion trap (FASTR) methods that utilize the hFcγRI allow rapid isolation of high expression clones expressing or secreting an antibody or receptor-Fc fusion protein of the invention. (See, e.g., US20090137416 A1, which is herein incorporated by reference.) Such high expression clones may be employed to isolate cells expressing proteins comprising a chimeric heavy chain constant region of the invention. FASTR methods may be utilized to directly screen and isolate cells expressing any recombinant polypeptide, antigen-binding protein, antibody, or Fc fusion protein of the invention.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions. Generally (i.e. in the context of a wild-type animal), a full-length light chain includes, from amino terminus to carboxyl terminus, a VL domain that includes FR1-CDR1-FR2-CDR2-FR3-CDR3-FR4, and a light chain constant domain.

The polypeptides of the invention comprise amino acid sequences that are derived from an immunoglobulin domain. A polypeptide or amino acid sequence "derived from" a designated protein refers to the origin of the polypeptide.

The term "hinge", as used herein, is intended to include the region of consecutive amino acid residues that connect the C-terminus of the $C_H1$ to the N-terminus of the $C_H2$ domain of an immunoglobulin. Several amino acids of the N-terminus of the $C_H2$ domain, which are coded by the $C_H2$ exon, are also considered part of the "lower hinge". Without being bound by any one theory, amino acids of the hinge region of IgG1, IgG2 and IgG4 have been characterized as comprising 12-15 consecutive amino acids encoded by a distinct hinge exon, and several N-terminal amino acids of the $C_H2$ domain (encoded by the $C_H2$ exon) (Brekke, O. H., et al. *Immunology Today* 16(2):85-90 (1995)). On the other hand, IgG3 comprises a hinge region consisting of four segments: one upper segment resembling the hinge region of IgG1, and 3 segments that are identical amino acid repeats unique to IgG3.

In the present disclosure for the convenience of the practitioner of the invention, amino acids of the hinge region for human IgG1, IgG2 and IgG4 have been identified herein by the EU numbering system of Kabat (Kabat, E. A. et al., Sequences of Proteins of Immunological interest. 5th ed. US Department of Health and Human Services, NIH publication No. 91-3242 (1991)), also known as "EU numbering" or the "EU index", as updated according to the IMGT® Scientific Chart, IMGT®, the international ImMunoGeneTics information system®, http://www.imgt.org/IMGTScientific-Chart/Numbering/Hu_IGHGnber.html, created: 17 May 2001, last updated: 10 Jan. 2013.

Figure 1:
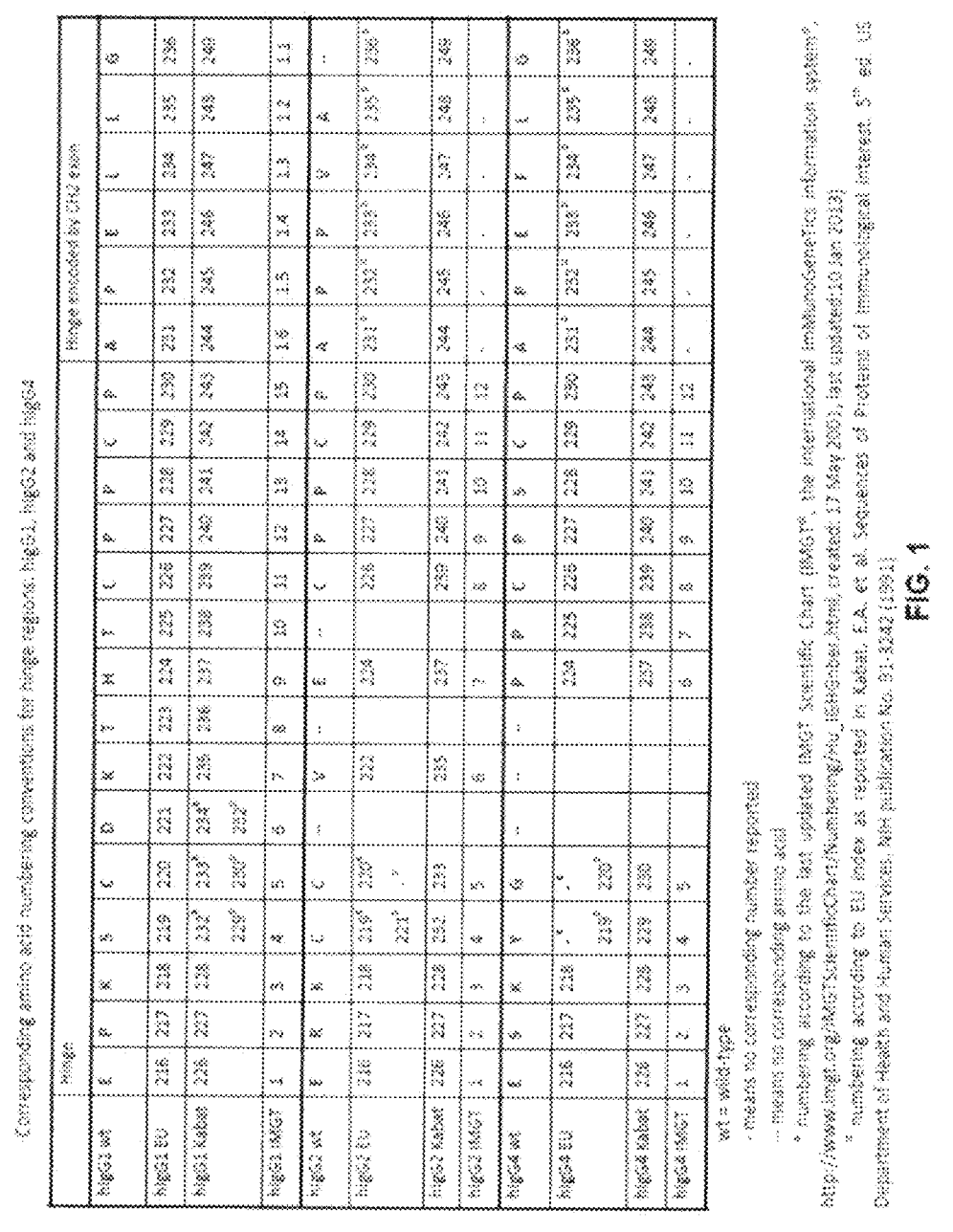

Correspondence between EU numbering for human IgG1, IgG2 and IgG4 hinge amino acids and IMGT unique domain numbering, IMGT exon numbering, and Kabat numbering conventions (see also Kabat, E. A. et al., 1991, supra) are described in FIG. 1 and as follows:

TABLE 1

IgG1 hinge numbering

| IgG1 (IGHG1) amino acids [SwissProt P01857] | IMGT Unique Numbering for the HINGE[a] | IMGT Exon Numbering[a] | EU Numbering | Kabat Numbering |
|---|---|---|---|---|
| (E) | 1 | 1 | 216 | 226 |
| P | 2 | 2 | 217 | 227 |
| K | 3 | 3 | 218 | 228 |
| S | 4 | 4 | 219 | 232[a] [229][b] |
| C | 5 | 5 | 220 | 233[a] [230][b] |
| D | 6 | 6 | 221 | 234[a] [232][b] |
| K | 7 | 7 | 222 | 235 |
| T | 8 | 8 | 223 | 236 |
| H | 9 | 9 | 224 | 237 |
| T | 10 | 10 | 225 | 238 |
| C | 11 | 11 | 226 | 239 |
| P | 12 | 12 | 227 | 240 |
| P | 13 | 13 | 228 | 241 |
| C | 14 | 14 | 229 | 242 |
| P | 15 | 15 | 230 | 243 |

TABLE 2

IgG1 C-domain hinge numbering

| IgG1 (IGHG1) amino acids [SwissProt P01857] | IMGT Unique Numbering for C-domains[a] | IMGT Exon Numbering[a] | EU Numbering | Kabat Numbering |
|---|---|---|---|---|
| (A) | 1.6 | 1 | 231 | 244 |
| P | 1.5 | 2 | 232 | 245 |
| E | 1.4 | 3 | 233 | 246 |
| L | 1.3 | 4 | 234 | 247 |
| L | 1.2 | 5 | 235 | 248 |
| G | 1.1 | 6 | 236 | 249 |

TABLE 3

IgG2 hinge numbering

| IgG2 (IGHG2) amino acids [SwissProt P01859] | IMGT Unique Numbering for the HINGE[a] | IMGT Exon Numbering[a] | EU Numbering | Kabat Numbering |
|---|---|---|---|---|
| (E) | 1 | 1 | 216 | 226 |
| R | 2 | 2 | 217 | 227 |
| K | 3 | 3 | 218 | 228 |
| C | 4 | 4 | 219[a] (221)[b] | 232 |
| C | 5 | 5 | 220[a] (—)[b] | 233 |
| V | 6 | 6 | 222 | 235 |
| E | 7 | 7 | 224 | 237 |
| C | 8 | 8 | 226 | 239 |
| P | 9 | 9 | 227 | 240 |
| P | 10 | 10 | 228 | 241 |
| C | 11 | 11 | 229 | 242 |
| P | 12 | 12 | 230 | 243 |

TABLE 4

IgG2 C-domain hinge numbering

| IgG2 (IGHG2) amino acids [Swiss Prot P01859] | EU numbering | Kabat numbering |
|---|---|---|
| (A) | 231 | 244 |
| P | 232 | 245 |
| P | 233 | 246 |
| V | 234 | 247 |
| A | 235 | 248 |
| — | 236 | 249 |

TABLE 5

IgG4 hinge numbering

| IgG4 (IGHG4) amino acids [SwissProt P01861] | IMGT Unique Numbering for the HINGE[a] | IMGT Exon Numbering[a] | EU Numbering | Kabat Numbering |
|---|---|---|---|---|
| (E) | 1 | 1 | 216 | 226 |
| S | 2 | 2 | 217 | 227 |
| K | 3 | 3 | 218 | 228 |
| Y | 4 | 4 | —[a] (219)[b] | 229 |
| G | 5 | 5 | —[a] (220)[b] | 230 |
| P | 6 | 6 | 224 | 237 |
| P | 7 | 7 | 225 | 238 |
| C | 8 | 8 | 226 | 239 |
| P | 9 | 9 | 227 | 240 |
| S | 10 | 10 | 228 | 241 |
| C | 11 | 11 | 229 | 242 |
| P | 12 | 12 | 230 | 243 |

TABLE 6

IgG4 C-domain hinge numbering

| IgG4 (IGHG4) amino acids [SwissProt P01861] | EU Numbering | Kabat Numbering |
|---|---|---|
| (A) | 231 | 244 |
| P | 232 | 245 |
| E | 233 | 246 |
| F | 234 | 247 |
| L | 235 | 248 |
| G | 236 | 249 |

Amino acids resulting from exon splicing are shown in parentheses.
— means no corresponding number reported
— means no corresponding amino acid in this position
[a] numbering according to the last updated IMGT Scientific Chart
[b] numbering according to EU index as reported in Kabat, E A, et al. 1991

See also, e.g., Lefranc, M.-P. et al., *Devel Comp Immunol*, 29, 185-203 (2005); and Edelman, G. M. et al. *PNAS USA*, 63:78-85 (1969).

For the purposes of this disclosure, an "upper hinge" region is intended to include amino acid residues from positions 216 to 227 according to EU numbering (amino acid residues from positions 226 to 240 according to Kabat numbering) (see also FIG. 2). A "lower hinge" region is intended to include amino acid residues from positions 228 to 236 according to EU numbering (amino acid residues from positions 241 to 249 according to Kabat numbering) (see also FIG. 2)

The term "chimeric", as used herein, means composed of parts of different origin. The phrase "chimeric protein" includes a first amino acid protein linked to a second amino acid protein that is not normally linked in nature. The amino acid sequences may normally exist as separate proteins or in a different arrangement on the same protein, and are brought together in a fusion polypeptide in a new arrangement. Chimeric proteins may be created by various methods known in the art, e.g. by chemical synthesis or by creating a polynucleotide that encodes for amino acids of the chimeric protein in the desired arrangement. Exemplary chimeric proteins include the chimeric hinge sequences connecting heavy chain domains of IgG, and the fusion proteins engineered to make the human antibodies, antigen-binding proteins and receptor-Fc fusion proteins of the present invention.

The chimeric proteins disclosed herein were designed to minimize the creation of immunogenic epitopes in the junctions, e.g. compared to a wild-type IgG Fc region or domain. The engineered proteins of the invention therefore have reduced immunogenicity, and display reduced binding to Fc receptors, as well as reduced to no effector functions.

The term "chimeric hinge", as used herein, is intended to include a chimeric protein comprising a first amino acid sequence derived from the hinge region of one Ig molecule and a second amino acid sequence derived from the hinge region of a different class or subclass of Ig molecule. Exemplary chimeric hinges of the present invention comprise a first amino acid sequence, or an "upper hinge" sequence, derived from a human IgG1 or human IgG4 hinge region, and a second amino acid sequence, or a "lower hinge" sequence, derived from a human IgG2 hinge region. In certain embodiments, the first or "upper hinge" sequence comprises amino acid residues from positions 216 to 227 according to EU numbering. In some embodiments, the second or "lower hinge" sequence comprises amino acid residues from positions 228 to 236 according to EU numbering.

The term "humanized antibody", as used herein, is intended to include antibodies in which CDR sequences are derived from the germline of another mammalian species, such as a mouse, and have been grafted onto human framework sequences. Humanized monoclonal antibodies may be generated by a hybridoma which includes a B lymphocyte cell obtained from a transgenic or transchromosomal non-human animal, such as a transgenic mouse, having a genome comprising a human heavy chain transgene and a light chain transgene, fused to an immortalized cell. For example, when non-human antibodies are prepared with respect to a particular antigen, the variable regions can be "reshaped" or "humanized" by grafting CDRs derived from nonhuman antibody on the FRs present in the human antibody to be modified. Application of this approach has been reported by Sato, K. et al. *Cancer Research* 53:851-856 (1993); Riechmann, L., et al., *Nature* 332:323-327 (1988); Verhoeyen, M., et al., *Science* 239:1534-1536 (1988); Kettleborough, C. A., et al., *Protein Engineering* 4:773-3783 (1991); Maeda, H., et al., *Human Antibodies Hybridoma* 2:124-134 (1991); Gorman, S. D., et al., *Proc Natl Acad Sci USA* 88:4181-4185 (1991); Tempest, P. R., et al., *Bio/Technology* 9:266-271 (1991); Co, M. S., et al., *Proc Natl Acad Sci USA* 88:2869-2873 (1991); Carter, P., et al., *Proc Natl Acad Sci USA* 89:4285-4289 (1992); and Co, M. S. et al., *J Immunol* 148:1149-1154 (1992). In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which are altered with respect to the original antibody, which are also termed one or more CDRs "derived from" one or more CDRs from the original antibody. Humanized antibodies may refer to chimeric molecules prepared using recombinant techniques.

In another embodiment, chimeric antibodies comprising human variable regions linked to murine constant regions, such as those produced by cell lines generated by a VELOCIMMUNE mouse, are humanized by replacing the murine constant region for a human constant region comprising SEQ ID NO: 1, SEQ ID NO:2, SEQ ID NO: 30, SEQ ID NO: 31, SEQ ID NO: 38 or SEQ ID NO:37.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "mouse or murine monoclonal antibody" refers to antibodies displaying a single binding specificity which have variable and constant regions derived from murine or mouse germline immunoglobulin sequences.

As used herein, the term "binding" in the context of the binding of an antibody, Ig, antibody-binding fragment, or Fc-containing protein to either, e.g., a predetermined antigen or to a FcR, typically refers to an interaction or association between a minimum of two entities, or molecular structures, such as an antibody-antigen interaction, or an Fc-containing protein to an FcγR (wherein the Fc-containing protein is an antibody, Ig, antibody-binding fragment, or Fc-fusion protein, e.g. receptor-Fc fusion).

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen or FcR as the ligand and the antibody, Ig, antibody-binding fragment, or Fc-containing protein as the analyte (or antiligand). Accordingly, the antibody or other binding protein binds to the predetermined antigen or receptor with an affinity corresponding to a $K_D$ value that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein).

The term "$K_D$" (M), as used herein, refers to the dissociation equilibrium constant of a particular antibody-antigen interaction, or the dissociation equilibrium constant of an antibody, Ig, antibody-binding fragment, or Fc-containing protein to an FcγR. There is an inverse relationship between $K_D$ and binding affinity, therefore the smaller the $K_D$ value, the higher the affinity. Thus, the term "lower affinity" relates to a lower ability to form an interaction and therefore a larger $K_D$ value.

The term "$k_d$" ($sec^{-1}$ or 1/s), as used herein, refers to the dissociation rate constant of a particular antibody-antigen interaction, or the dissociation rate constant of an antibody, Ig, antibody-binding fragment, or Fc-containing protein to an FcγR. Said value is also referred to as the $k_{off}$ value.

The term "$k_a$" ($M^{-1} \times sec^{-1}$ or 1/M), as used herein, refers to the association rate constant of a particular antibody-antigen interaction, or the association rate constant of an antibody, Ig, antibody-binding fragment, or Fc-containing protein to an FcγR.

The term "$K_A$" ($M^{-1}$ or 1/M), as used herein, refers to the association equilibrium constant of a particular antibody-antigen interaction, or the association equilibrium constant of an antibody, Ig, antibody-binding fragment, or Fc-containing protein to an FcγR. The association equilibrium constant is obtained by dividing the $k_a$ by the $k_d$.

The term "$EC_{50}$" or "$EC_{50}$", as used herein, refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. Thus, reduced binding is observed with an increased $EC_{50}$, or half maximal effective concentration value.

In one embodiment, decreased binding can be defined as an increased $EC_{50}$ antibody concentration which enables binding to the half-maximal amount of target cells.

In some embodiments, decreased cytotoxic activity can be defined as an increased $EC_{50}$ antibody concentration which enables lysis of the half-maximal amount of target cells.

In other embodiments, decreased proliferation can be defined as an increased $EC_{50}$ antibody concentration which enables proliferation of the half-maximal amount of target cells.

The phrase "bispecific antibody" as used herein includes antibodies that are specific for different epitopes of one target polypeptide or may contain antigen-binding domains specific for more than one target polypeptide. See, e.g., Tutt et al. (1991) *J. Immunol.* 147:60-69. For example, the human antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity. As such, bispecific antibody also includes two antibodies of different specificity.

Another strategy, for example using a common light chain, may be employed as described in US Patent Application Publication No. 20100331527A1, wherein two antibodies of different specificity use the same light chain. In certain embodiments, the heavy chain of at least one of the Ig heavy chains in a bispecific antibody is modified to comprise a chimeric heavy chain constant region comprising a recombinant polypeptide of the invention. In some embodiments, at least one of the heavy chains is modified in the CH3 domain resulting in a differential affinity for the bispecific antibody for an affinity reagent, such as Protein A, for ease of isolation. In another embodiment, at least one of the heavy chains in such bispecific antibody comprises an amino acid modification at i) 95R or ii) 95R and 96F in the IMGT numbering system (95R and 96F correspond to 435R and 436F in the EU numbering system), for example SEQ ID NO: 37 and SEQ ID NO: 38. (See US20100331527A1, the contents of which are herein incorporated by reference.) A multispecific antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antigen-binding protein or antibody of the present invention using routine techniques available in the art.

As used herein, "isotype" refers to the immunoglobulin class (for instance, IgG1, IgG2, IgG3, IgG4, IgD, IgA, IgE, or IgM) that is encoded by heavy chain constant region genes.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former, but not the latter, is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specific antigen binding peptide (in other words, the amino acid residue is within the footprint of the specific antigen binding peptide).

As used herein, a humanized antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody V domain sequence is at least 90%, such as at least 95%, for instance at least 96%, such as at least 97%, for instance at least 98%, or such as at least 99% identical in amino acid V domain sequence to the amino acid sequence encoded by the germline immunoglobulin gene.

Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. Mice that express antibodies that are fully human, or partly human and partly mouse, have previously been reported. For example, a transgenic mouse can have a human light chain transgene and either a human heavy chain transgene or human heavy chain transchromosome, such that the mouse produces human antibody when immunized with target antigen and/or cells expressing the target antigen. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching.

VELOCIMMUNE® genetically engineered mice comprise a replacement of unrearranged V(D)J gene segments at endogenous mouse loci with human V(D)J gene segments. VELOCIMMUNE® mice express chimeric antibodies having human variable domains and mouse constant domains (see, e.g., U.S. Pat. No. 7,605,237). Most other reports concern mice that express fully human antibodies from fully human transgenes in mice that have disabled endogenous immunoglobulin loci.

The VELOCIMMUNE® mouse includes, in part, having a genome comprising human variable regions operably linked to endogenous mouse constant region loci such that the mouse produces antibodies comprising a human heavy chain variable region and a mouse heavy chain constant region in response to antigenic stimulation. The DNA encoding the variable regions of the heavy chains of the antibodies can be isolated and operably linked to DNA encoding the human heavy chain constant regions of the invention. The DNA can then be expressed in a cell capable of expressing the fully human heavy chain of the antibody.

A transgenic, nonhuman animal can also be used for production of antibodies against a specific antigen by introducing into the animal genes encoding such specific antibody, for example by operatively linking the genes to a gene which is expressed in the milk of the animal.

The phrase "effector functions", as used herein, is intended to include the functional capabilities imparted by an Fc-containing protein upon binding to an FcγR. Without being bound to any one theory, formation of an Fc/FcγR complex recruits a variety of effector cells to sites of bound antigen, typically resulting in diverse signaling events within the cells and important subsequent immune responses.

An "effectorless polypeptide" refers to a recombinant polypeptide, antigen-binding protein or antibody which has altered or reduced effector function as compared to a corresponding recombinant polypeptide, antigen-binding protein or antibody comprising a wild-type heavy chain constant region of the IgG1 or IgG4 isotype. In some embodiments, the effector function that is reduced or altered is a cytotoxic effector function, e.g., cytotoxicity, complement-dependent cytotoxicity (CDC), antibody-dependent cytotoxicity (ADCC), or antibody-dependent cellular phagocytosis (ADCP). In one embodiment, the effector function that is reduced or altered is complement-dependent cytotoxicity. In another embodiment, the effector function that is reduced or altered is antibody-dependent cytotoxicity. In other embodiments, the effector function that is reduced or altered is cellular proliferation.

Several antibody effector functions are mediated at least in part by Fc receptors (FcRs), which bind the Fc region of an antibody in the constant domain (specifically, the $C_H2$ and $C_H3$ domain) of a typical immunoglobulin. There are a number of Fc receptors which are specific for the different classes of immunoglobulins, i.e. IgG, IgE, IgA, IgM, and IgD. The human IgG Fc receptor family is divided into three groups: FcγRI (CD64), which is capable of binding IgG with high affinity, FcγRII (CD32) and FcγRIII (CD16) both of which are low affinity receptors. Each FcγR subclass is encoded by two or three genes, and alternative RNA splicing leads to multiple transcripts, hence, a broad diversity in FcγR isoforms exists (e.g. FcγRIA (CD64; FCGR1A), FcγRIB (CD64; FCRG1B), FcγRIIA (CD32; FCGR2A), FcγRIIB (CD32; FCGR2B), FcγRIIC (CD32; FCGR2C), FcγRIIIA (CD16a; FCGR3A), and FcγRIIIB (CD16b; FCGR3B)). Additionally, the FcRn, or neonatal Fc receptor (also known as the Fc receptor transporter, alpha, or FCGRT) is capable of transferring IgG antibodies from mother to fetus across the placenta. Furthermore, Fc receptors are expressed on a variety of cells, including, e.g., B cells, monocytes, dendritic cells, neutrophils, and certain lymphocytes. For example, U937 cells, a human monocyte cell line, express both FcγRI and FcγRIIA (see e.g., Jones, et al. *J Immunol* 135(5):3348-53 (1985); and Brooks, et al. *J Exp Med* 170:1369-85 (October 1989)).

Binding of an Ig Fc to its receptor brings these effector cells to sites of the bound antigen, resulting ultimately in a variety of signaling and immune responses, including B cell activation, inflammatory responses, cytotoxic responses, and phagocytic responses. As such, reduced or altered binding of an Ig Fc to its receptor may result in reduced effector functions.

Alternatively, increased "effector functions" such as cytotoxicity, complement-dependent cytotoxicity ("CDC"), antibody-dependent cytotoxicity ("ADCC") and abnormal antibody production, may be unwanted side effects associated with certain therapeutic antibodies.

The phrase "antibody-dependent cellular cytotoxicity", "Antibody-dependent cell-dependent cytotoxicity", or "ADCC" means an activity to damage a target cell when an Fcγ receptor-bearing cell (an immune cell or the like) binds to an Fc portion of a specific antibody through the Fcγ receptor, when the specific antibody has attached to a cell-surface antigen of the target cell. Thus, ADCC is a mechanism by which Fc receptor-positive effector cells can lyse target cells that have adherent antigen-specific molecule. The ADCC activity can be evaluated by a number of well-known methods, including measuring the fluorescent intensity using a fluorescent dye such as calcein AM (Wako Pure Chemical Industries, Ltd., 349-07201). When this approach is employed, the cytotoxic activity (%) can be calculated, using the obtained values, according to the equation: $(A-C)/(B-C)\times100$, wherein A is a fluorescent value in each sample, B is an average fluorescent value of the cells lysed and released into a medium with Nonidet P-40 having a final concentration of 1%, and C is an average fluorescent value when only the medium was added.

The phrase "antibody-dependent cellular phagocytosis" or "ADCP", as used herein, relates to effector function that eliminates (or kills) a target cell by engulfing the target cell rather than inducing cytolysis. ADCP may be an important in vivo mechanism for killing tumor cells. ADCP can be measured by two-color fluorescence flow cytometry methods, for example methods utilizing, e.g. PKH2 (green fluorescent dye) and phycoerythrin-conjugated (red) monoclonal antibodies against different cell surface proteins to differentiate the test cells, thus determining phagocytic activity and rate of phagocytosis. Therapeutic strategies that selectively activate FcγRIIa relative to FcγRIIb may enhance macrophage phagocytic activity (Richards, J O, et al. 2008 *Mol Cancer Ther* 7(8):2517-27).

The phrase "complement-directed cytotoxicity" or "CDC", as used herein, includes a cytotoxic activity by the complement system. The CDC activity is measured by well-known methods, for example the target cells, antibody, and complement solution (such as baby rabbit complement (Cedarlane Technologies) are incubated and are allowed to react, according to standard protocols (NIAID Manual of Tissue Typing Techniques 1979-1980, Edited by J. G. Ray, NIH Publication No. NIH-83-545.) The cytotoxic activity can be calculated in the same manner as the measurement of the ADCC activity. The cytotoxic activity can also be measured using a fluorescent dye (such as calcein) or radioactive dyes similarly to the above with respect to ADCC.

The phrase "cytotoxicity" or "direct cytotoxicity" includes any cytotoxic activity including that which is independent of NK cells. Cytotoxicity may be measured by techniques well known in the art, for example, determining cell lysis or cell death, i.e. apoptosis. Direct cell lysis, or cell killing, can be evaluated by a number of well-known methods, including measuring the fluorescent intensity using calcein and calculating an average fluorescent value in a similar fashion as described with respect to ADCC hereinabove. Alternatively, a cytotoxic molecule, such as an antibody, is effective in an apoptosis assay by activating a genetic program of controlled cell death. Apoptosis is characterized by well defined cytological and molecular events including a change in the refractive index of the cell, cytoplasmic shrinkage, nuclear condensation and cleavage of DNA into regularly sized fragments. Cells that are undergoing apoptosis shut down metabolism, lose membrane integrity and form membrane blebs. The apoptotic activity is measured using standard methods of determining dying and/or dead cells. In order to measure apoptosis, cytotoxicity assays can be employed. These assays may be radioactive or non-radioactive assays that measure increases in plasma membrane permeability, since dying cells become leaky, colorimetric assays may be employed that measure reduction in the metabolic activity of mitochondria based on the knowledge that mitochondria in dead cells cannot metabolize dyes, while mitochondria in live cells can. Bioluminescent cytotoxicity assays (e.g. CytoTox-Glo™, Promega) were developed to measure the release of stable protease markers into the cell culture medium. Protease activity is considered a robust enzymatic cell death marker, and may be used as a ratiometric measurement of viable and dead cells (Niles, A. L., et al. *Anal Biochem*, 366(2): 197-206, 15 Jul. 2007).

One can also measure early indicators for apoptosis such as alterations in membrane asymmetry resulting in occurrence of phosphatidylserine on the outside of the cell surface (Annexin V based assays). Alternatively, later stages of apoptosis, such as activation of caspases can be measured in populations of cells or in individual cells. In addition, measurement of release of cytochrome C and AIF into cytoplasm by mitochondria or fragmentation of chromosomal DNA can be determined. Terminal deoxynucleotidyl transferase dUTP nick end labeling (TUNEL) is a common method for detecting DNA fragmentation that results from apoptotic signaling cascades. The assay relies on the presence of nicks in the DNA which can be identified by terminal deoxynucleotidyl transferase, an enzyme that will catalyze the addition of bromolated dUTPs that are secondarily detected with a specific labelled antibody.

Cytotoxicity may be complement-directed, or antibody-directed, or directly associated with the binding of a cytotoxic molecule or cell.

In certain embodiments, antibodies of the invention exhibit cytotoxicity of less than 20% cytolysis (i.e. % cytotoxicity), or less than 10%, or 5%, 4%, 3%, 2%, or even 0% or undetectable cytolysis (cytotoxicity), as measured in an in vitro or ex vivo cell killing assay. In certain embodiments, antibodies of the invention exhibit less than 20%, 10%, or 5%, 4%, 3%, 2%, or even 0% or undetectable cytotoxicity, at an antibody concentration of 10 nM.

In other embodiments, antibodies exhibit apoptotic activity of less than 20% cytolysis (i.e. % cytotoxicity), or less than 10%, or 5%, 4%, 3%, 2%, or even 0% or undetectable cytolysis (cytotoxicity), as measured in an in vitro or ex vivo cell killing assay. In still other embodiments, In certain embodiments, antibodies of the invention exhibit less than 20%, 10%, or 5%, 4%, 3%, 2%, or even 0% or undetectable apoptotic activity, at an antibody concentration of 10 nM.

In still other embodiments, antibodies exhibit CDC activity of less than about 50% cytotoxicity, or less than cytotoxicity 40%, 30%, 20%, 10%, or 5%, 4%, 3%, 2%, or even 0% or undetectable cytotoxicity, as measured in an in vitro or ex vivo cell killing assay. In still other embodiments, In certain embodiments, antibodies of the invention exhibit less than 50%, 40%, 30%, 20%, 10%, or 5%, 4%, 3%, 2%, or even 0% or undetectable CDC activity, at an antibody concentration of 100 nM. In more embodiments, antibodies exhibit ADCC activity of less than about 50% cytotoxicity, or less than cytotoxicity 40%, 30%, 20%, 10%, or 5%, 4%, 3%, 2%, or even 0% or undetectable cytotoxicity, as measured in an in vitro or ex vivo cell killing assay. In still other embodiments, In certain embodiments, antibodies of the invention exhibit less than 50%, 40%, 30%, 20%, 10%, or 5%, 4%, 3%, 2%, or even 0% or undetectable ADCC activity, at an antibody concentration of 100 nM.

The present invention provides antibodies, antigen-binding proteins and Fc-fusion proteins that comprise recombinant polypeptides comprising a chimeric hinge, and further provide reduced effector functions. The properties of such recombinant polypeptides of the invention may be compared to the properties of one or more reference proteins. See the examples below for reference, or control antibodies and antigen-binding proteins which have corresponding variable regions and constant regions (e.g. having a wild-type IgG1 $C_H$ region (SEQ ID NO:13) or a wild-type IgG4 $C_H$ region (SEQ ID NO:15)) compared to the chimeric antibodies of the invention, and may be used in certain testing methodologies for comparison of functional or pharmacokinetic properties to the antibodies and antigen-binding proteins of the invention. It is understood that a corresponding wild-type IgG $C_H$ region differs from chimeric $C_H$ regions of the invention in that the "wild-type" IgG $C_H$ region is derived from the natural IgG amino acid sequence containing (from N-terminal to C-terminal) a CH1 domain, a hinge, a CH2 domain, and a CH3 domain. Wild-type IgG may include variants having one or more amino acid modifications while retaining essentially the same functional characteristics as natural IgG. A corresponding antibody or polypeptide may be assembled to have the same target binding domain (e.g. $V_H$ and/or $V_L$) as the antibody or polypeptide having the chimeric $C_H$ region, or otherwise has essentially the same functionality for the purpose of comparison in certain assays.

It has been shown in the Examples that isolated antibodies of the invention bind weakly to FcγR expressing cells, e.g. effector cells, but however lack effector functions, such as cytotoxicity and proliferation, compared to the effector functions of a corresponding antibody comprising a wild-type IgG1 or IgG4 $C_H$ region.

Further Aspects of the Invention

In one aspect, the invention provides a recombinant polypeptide comprising a chimeric hinge region. In some aspects, the chimeric hinge region comprises a human IgG2 lower hinge amino acid sequence PCPAPPVA (SEQ ID NO: 3) from positions 228 to 236 (EU numbering). In other aspects, the chimeric hinge region comprises: a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering), from N-terminus to C-terminus.

In other aspects, the chimeric hinge region comprises: an upper hinge amino acid sequence from positions 216 to 227 (EU numbering) selected from the group consisting of SEQ ID NO:4 and SEQ ID NO:5, and a lower hinge amino acid sequence PCPAPPVA (SEQ ID NO: 3) from positions 228 to 236 (EU numbering), from N-terminus to C-terminus.

The invention provides a recombinant polypeptide comprising, from N-terminus to C-terminus, a CH1 domain, a chimeric hinge, a CH2 domain, and a CH3 domain wherein: the CH1 domain comprises at least the amino acid sequence DKKV or DKRV from positions 212 to 215 (EU numbering), the chimeric hinge comprises a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering), the CH2 domain comprises a human IgG4 CH2 domain amino acid sequence from positions 237 to 340 (EU numbering), and the CH3 domain comprises a human IgG1 or a human IgG4 CH3 domain sequence from positions 341 to 447 (EU numbering), or a variant thereof. In one embodiment, the present invention provides a monoclonal antibody comprising a heavy chain constant region comprising or consisting of SEQ NO: 1, SEQ ID NO: 2, SEQ ID NO: 30, or SEQ ID NO: 31. In another embodiment, the present invention provides a monoclonal antibody comprising at least one heavy chain with a constant region comprising or consisting of SEQ ID NO: 38 or 37.

human IgG1 or a human IgG4 upper hinge amino acid sequence from positions 216 to 227 (EU numbering), or a natural variant thereof, and a human IgG2 lower hinge amino acid sequence from positions 228 to 236 (EU numbering), the CH2 domain comprises a human IgG4 CH2 domain sequence from positions 237 to 340 (EU numbering), or a natural variant thereof, and the CH3 domain comprises a human IgG1 or a human IgG4 CH3 domain sequence from positions 341 to 447 (EU numbering), or a natural variant thereof, and the CH region has an amino acid sequence with at least about 95%, or about 96%, or about 97%, or about 98%, or about 99% identity to SEQ ID NO: 30 or SEQ ID NO: 31. In some embodiments, the CH region has an amino acid sequence with at least about 95%, or about

TABLE 7

Representative chimeric $C_H$ constructs

| $C_H$ construct SEQ ID NO | CH1 | Upper Hinge | Lower Hinge | CH2 | CH3 |
|---|---|---|---|---|---|
| 1 | DKRV (SEQ ID NO: 5) | ESKYGPPCP (SEQ ID NO: 7) | PCPAPPVA (SEQ ID NO: 3) | SEQ ID NO: 10 | SEQ ID NO: 12 |
| 2 | DKKV (SEQ ID NO: 4) | EPKSCDKTHTCP (SEQ ID NO: 6) | PCPAPPVA (SEQ ID NO: 3) | SEQ ID NO: 10 | SEQ ID NO: 11 |
| 30 | SEQ ID NO: 43 | EPKSCDKTHTCP (SEQ ID NO: 6) | PCPAPPVA (SEQ ID NO: 3) | SEQ ID NO: 10 | SEQ ID NO: 11 |
| 31 | SEQ ID NO: 44 | ESKYGPPCP (SEQ ID NO: 7) | PCPAPPVA (SEQ ID NO: 3) | SEQ ID NO: 10 | SEQ ID NO: 12 |
| 37 | SEQ ID NO: 43 | EPKSCDKTHTCP (SEQ ID NO: 6) | PCPAPPVA (SEQ ID NO: 3) | SEQ ID NO: 10 | SEQ ID NO: 41 |
| 38 | SEQ ID NO: 44 | ESKYGPPCP (SEQ ID NO: 7) | PCPAPPVA (SEQ ID NO: 3) | SEQ ID NO: 10 | SEQ ID NO: 42 |

In some embodiments, the recombinant polypeptide is selected from the group consisting of an antibody, antigen-binding protein and receptor-Fc fusion protein.

In some embodiments, the isolated antibody, antigen-binding protein, or receptor-Fc fusion protein comprises a heavy chain construct comprising a CH region, from N-terminus to C-terminus, a CH1 domain, a chimeric hinge, a CH2 domain, and a CH3 domain, wherein the CH1 domain comprises the amino acid sequence DKKV or DKRV, the chimeric hinge comprises a human IgG1 or a human IgG4 upper hinge amino acid sequence from positions 216 to 227 (EU numbering), or a natural variant thereof, and a human IgG2 lower hinge amino acid sequence from positions 228 to 236 (EU numbering), the CH2 domain comprises a human IgG4 CH2 domain sequence from positions 237 to 340 (EU numbering), or a natural variant thereof, and the CH3 domain comprises a human IgG1 or a human IgG4 CH3 domain sequence from positions 341 to 447 (EU numbering), or a natural variant thereof, and the CH region has an amino acid sequence with at least about 95%, or about 96%, or about 97%, or about 98%, or about 99% identity to SEQ ID NO:1 or SEQ ID NO:2.

In another embodiment, the present invention provides an isolated antibody, antigen-binding protein, or receptor-Fc fusion protein comprising a heavy chain construct comprising a CH region, from N-terminus to C-terminus, a CH1 domain, a chimeric hinge, a CH2 domain, and a CH3 domain, wherein the CH1 domain comprises the amino acid sequence DKKV or DKRV, the chimeric hinge comprises a 96%, or about 97%, or about 98%, or about 99% identity to SEQ ID NO: 38 or SEQ ID NO: 37.

Such "variant" or "natural variant" $C_H$ domains of the invention, e.g. Fc domains and Fc domain fragments, comprise one or more additions, deletions, or substitutions of amino acids when compared to the wild-type sequence that such $C_H$ domains of the invention are derived from, but essentially function as desired. In some examples, the $C_H$ domain or Fc domain exhibits weak or no binding to certain FcγR expressing cells, e.g. effector cells, resulting in altered effector functions, such as cytotoxicity and proliferation. In one example, such variants include modifications such as additions, deletions, or substitutions of amino acids in the CH3 domain engineered for the isolation of bispecific molecules.

In one embodiment, the present invention provides a monoclonal antibody comprising a heavy chain variable region and a heavy chain constant region comprising or consisting of SEQ ID NO:1, SEQ ID NO:2, SEQ ID NO: 30, SEQ ID NO: 31, SEQ ID NO: 38, or SEQ ID NO: 37, or a sequence with at least about 95%, or about 96%, or about 97%, or about 98%, or about 99% to such heavy chain constant region. In another embodiment, the present invention provides a monoclonal antibody comprising a light chain variable region, a heavy chain variable region and a heavy chain constant region comprising or consisting of SEQ ID NO:1, SEQ ID NO:2, SEQ ID NO: 30, SEQ ID NO: 31, SEQ ID NO: 38, or SEQ ID NO: 37, or a sequence with at least about 95%, or about 96%, or about 97%, or about 98%, or about 99% to such heavy chain constant region.

In another embodiment, the invention is an isolated antibody, or antigen-binding fragment thereof, comprising a heavy chain constant region ($C_H$) having (i) the amino acid sequence of SEQ NO: 1 or having the amino acid sequence encoded by SEQ ID NO: 33, or (ii) the amino acid sequence of SEQ NO: 31 or having the amino acid sequence encoded by SEQ ID NO: 29, or (iii) a sequence with at least about 95%, or about 96%, or about 97%, or about 98%, or about 99% identity to a sequence described in (i) or (ii). In another embodiment, the invention is an isolated antibody, or antigen-binding fragment thereof, comprising a heavy chain constant region ($C_H$) having (i) the amino acid sequence of SEQ NO: 2 or having the amino acid sequence encoded by SEQ ID NO: 32, or (ii) the amino acid sequence of SEQ NO: 30 or having the amino acid sequence encoded by SEQ ID NO: 28, or (iii) a sequence with at least about 95%, or about 96%, or about 97%, or about 98%, or about 99% identity to a sequence described in (i) or (ii).

In still another embodiment, the invention is an isolated antibody, or antigen-binding fragment thereof, comprising a heavy chain constant region ($C_H$) having (i) the amino acid sequence of SEQ NO: 38 or having the amino acid sequence encoded by SEQ ID NO: 36, or (ii) the amino acid sequence of SEQ NO: 37 or having the amino acid sequence encoded by SEQ ID NO: 35, or (iii) a sequence with at least about 95%, or about 96%, or about 97%, or about 98%, or about 99% identity to a sequence described in (i) or (ii).

In some embodiments, the isolated antibody is a monoclonal antibody. In other embodiments, the isolated antibody, or antigen binding fragment thereof, is a humanized, chimeric, single-chain antibody or bispecific antibody.

In another embodiment, the invention is an Fc-containing protein comprising (i) the amino acid sequence of SEQ NO: 1 or the amino acid sequence encoded by SEQ ID NO: 33, or (ii) the amino acid sequence of SEQ NO: 31 or the amino acid sequence encoded by SEQ ID NO: 29, or (iii) a sequence with at least about 95%, or about 96%, or about 97%, or about 98%, or about 99% identity to a sequence described in (i) or (ii). In another embodiment, the invention is an Fc-containing protein comprising (i) the amino acid sequence of SEQ NO: 2 or the amino acid sequence encoded by SEQ ID NO: 32, or (ii) the amino acid sequence of SEQ NO: 30 or the amino acid sequence encoded by SEQ ID NO: 28, or (iii) a sequence with at least about 95%, or about 96%, or about 97%, or about 98%, or about 99% identity to a sequence described in (i) or (ii).

In another embodiment, the invention is an Fc-containing protein comprising (i) the amino acid sequence of SEQ NO: 38 or the amino acid sequence encoded by SEQ ID NO: 36, or (ii) the amino acid sequence of SEQ NO: 37 or the amino acid sequence encoded by SEQ ID NO: 35, or (iii) a sequence with at least about 95%, or about 96%, or about 97%, or about 98%, or about 99% identity to a sequence described in (i) or (ii).

In another embodiment, the present invention provides a composition comprising the antibody, antigen-binding protein or Fc fusion protein described.

The present invention provides an antibody or antigen-binding protein that lacks cytotoxic or cytolytic effector function. In some aspects, the antibody or antigen-binding protein lacks cytotoxic or cytolytic effector function and comprises SEQ ID NO:1, SEQ ID NO:2, SEQ ID NO: 30, SEQ ID NO: 31, SEQ ID NO: 38, or SEQ ID NO: 37.

The present invention provides an antibody or antigen-binding protein having cytotoxic activity that is at least 10-fold less, or at least 50-fold less, or at least 100-fold less, or at least 1000-fold less, or at least 10000-fold less than the cytotoxic activity of a corresponding antibody comprising a wild-type IgG1 or wild-type IgG4 CH region.

The present invention provides an antibody capable of binding to an FcγR, wherein such antibody comprises a recombinant polypeptide comprising SEQ ID NO:1, SEQ ID NO:2, SEQ ID NO: 30, SEQ ID NO: 31, SEQ ID NO: 38, or SEQ ID NO: 37. In some embodiments, the antibody is capable of binding to an FcγR with lower affinity compared to the binding affinity of a corresponding antibody comprising a wild-type IgG1 or wild-type IgG4 heavy chain constant region. In some embodiments, the antibody is capable of activating an FcγR at a half-maximal concentration ($EC_{50}$) of greater than about 10 nM, or about 20 nM, or about 30 nM, or about 40 nM, about 50 nM, about 100 nM. In some embodiments, the FcγR is a human or cynomolgus FcγRII. In other embodiments, the FcγR is FcγRIIA or FcγRIIB. In some embodiments, the antibody is capable of binding to FcγRIIA having an affinity ($K_D$ value) of about 10 μM, or about 20 μM, or about 30 μM, or about 40 μM, about 50 μM, about 100 μM. In other embodiments, the antibody or recombinant polypeptide binds to FcγRIIA with an affinity greater than the affinity of the antibody or recombinant polypeptide to FcγRIIB.

In some embodiments, the antibody is capable of binding to FcγRIIB having an affinity (KD value) of about 10 μM, or about 20 μM, or about 30 μM, or about 40 μM, about 50 μM, about 100 μM. In some embodiments, the antibody or recombinant polypeptide binds to FcγRIIA with an affinity ($K_D$ value) substantially similar to the affinity of the antibody or recombinant polypeptide to FcγRIIB.

For certain embodiments, it may be desirable for the chimeric antibodies of the invention to engage, and even indirectly enhance FcγRIIA-mediated activity, even though the chimeric antibodies may have wild-type affinities for FcγRIIA. Without being bound to any one theory, certain antibodies, and thus therapeutics, may benefit from a weakened interaction (compared to wild-type antibodies) with the inhibitory receptor FcγRIIB, which may shift the balance between the activating FcγRIIA and the inhibitory FcγRIIB receptors in favor of activation.

The present invention encompasses the production of monoclonal antibodies comprising a recombinant polypeptide comprising SEQ ID NO: 1, SEQ ID NO: 2, SEQ ID NO: 30, SEQ ID NO: 31, SEQ ID NO: 38, or SEQ ID NO: 37 and having specificities for various target antigens. The invention provides a method for producing an antibody comprising: a) introducing the vector comprising a nucleic acid molecule encoding an antibody, or fragment thereof, of the invention into a mammalian host cell, b) culturing the host cell capable of expressing the antibody, and c) isolating the antibody from the cell culture media.

Monoclonal antibodies of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B lymphocyte cells obtained from mice immunized with an antigen of interest, for instance, in the form of cells expressing the antigen on the surface, or a nucleic acid encoding an antigen of interest. Monoclonal antibodies may also be obtained from hybridomas derived from antibody-expressing cells of immunized humans or non-human mammals such as rats, rabbits, dogs, primates, etc.

In one embodiment, the antibody of the invention is a human antibody. Human monoclonal antibodies may be generated using transgenic or transchromosomal mice carrying parts of the human immune system rather than the mouse system. Such transgenic and transchromosomic mice include mice referred to herein as VELOCIMMUNE mice, HuMAb mice and KM mice, respectively, and are collectively referred to herein as "transgenic mice" and are described hereinabove.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957. Expression vectors comprising a mouse UP-II promoter operatively linked to the DNA encoding the Ig heavy and light chain sequences of interest may be engineered for expression and secretion of the proteins of interest in urine of a transgenic animal (See, e.g., U.S. Pat. No. 5,824,543).

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., *J. Mol. Biol.* 227, 381 (1991) (phage display), Vaughan et al., *Nature Biotech* 14, 309 (1996) (phage display), Hanes and Plucthau, *PNAS USA* 94, 4937-4942 (1997) (ribosomal display), Parmley and Smith, *Gene* 73, 305-318 (1988) (phage display), Scott *TIBS* 17, 241-245 (1992), Cwirla et al., *PNAS USA* 87, 6378-6382 (1990), Russel et al., *Nucl. Acids Research* 21, 1081-1085 (1993), Hogenboom et al., *Immunol. Reviews* 130, 43-68 (1992), Chiswell and McCafferty *TIBTECH* 10, 80-84 (1992), and U.S. Pat. No. 5,733,743). If display technologies are utilized to produce antibodies that are not human, such antibodies may be humanized.

The engineered heavy chain constant ($C_H$) regions of the invention will provide reduced effector functions. Either of the human light chain constant ($C_L$) regions, kappa or lambda, may be used. If desired, the class of an antibody of the present invention may be switched by known methods.

The present invention provides the antibodies of the invention produced by a host cell. In one embodiment, the invention provides a method for producing a monoclonal antibody comprising a) immunizing VELOCIMMUNE® mice with an antigen sufficient to cause an antibody immune response, b) obtaining serum from such mice and testing for antibody titer against said antigen, c) harvesting B cells from the spleens of such immunized mice shown to have elevated antibody titers and fusing said B cells with mouse myeloma cells to form such hybridoma, d) isolating chimeric antibody from such hybridoma by protein A chromatography, such chimeric antibody having a human variable region and a mouse constant region, e) selecting a chimeric antibody having desirable characteristics, and f) replacing the mouse constant regions of such antibodies with a human constant region of the invention, for example, such human constant region comprising SEQ ID NO:1, SEQ ID NO:2, SEQ ID NO: 30, SEQ ID NO: 31, SEQ ID NO: 38, or SEQ ID NO: 37.

In one embodiment, the antibody of the invention is a full-length IgG antibody. In another embodiment, the antibody of the invention is an antibody fragment or a single-chain antibody. In still another embodiment, the antibody of the invention is a fully human IgG antibody.

In some aspects of the invention, the antibody is a bispecific antibody wherein each antigen-binding domain of such molecule or antibody comprises a $V_H$ region paired with a $V_L$ region. In certain embodiments, the bispecific antibody comprises a first antigen-binding domain and a second antigen binding domain each comprise different, distinct $V_H$ regions ith a common $V_L$ region. In some embodiments, the bispecific antibodies are constructed comprising a first antigen-binding domain that specifically binds a first antigen, wherein the first antigen-binding domain comprises an $V_H$ region/$V_L$ region pair derived from a first antibody directed against the first antigen; and a second antigen-binding domain that specifically binds a second antigen, wherein the second antigen-binding domain comprises an $V_H$ region derived from a second antibody directed against a second antigen paired with an $V_L$ region derived from the first antibody (e.g., the same $V_L$ region that is included in the antigen-binding domain of the first antibody). In some embodiments, the heavy chain of at least one of the antibodies, i.e. the first antibody or the second antibody or both antibodies, in a bispecific antibody is modified to comprise a chimeric heavy chain constant region ($C_H$ region). In other embodiments, the bispecific antibody comprises SEQ ID NO:1, SEQ ID NO:2, SEQ ID NO: 30, SEQ ID NO: 31, SEQ ID NO: 38, or SEQ ID NO: 37.

In some aspects of the invention, two antibodies of different specificity use the same light chain. In certain embodiments, the heavy chain of at least one of the Ig heavy chains in a bispecific antibody is modified to comprise a chimeric heavy chain constant region comprising a recombinant polypeptide of the invention. In some embodiments, at least one of the heavy chains is modified in the CH3 domain resulting in a differential affinity for the bispecific antibody for an affinity reagent, such as Protein A, for ease of isolation. In another embodiment, at least one of the heavy chains in such bispecific antibody comprises an amino acid modification at i) 95R or ii) 95R and 96F in the IMGT numbering system (95R and 96F correspond to 435R and 436F in the EU numbering system).

In other aspects, the antibody is a bispecific antibody wherein the bispecific antibody comprises:
(a) a first heavy chain comprising an antigen-binding domain capable of recognizing and binding to a first target antigen,
(b) a second heavy chain comprising an antigen-binding domain capable of recognizing and binding to a second target antigen,
(c) a common light chain antigen-binding domain capable of recognizing and binding to the first or second target antigen,
wherein the heavy chain of (a) or (b) or both (a) and (b) further comprises the heavy chain constant region comprising SEQ ID NO:1 or SEQ ID NO: 31.

In still other aspects, the antibody is a bispecific antibody wherein the bispecific antibody comprises:
(a) a first heavy chain comprising an antigen-binding domain capable of recognizing and binding to a first target antigen,
(b) a second heavy chain comprising an antigen-binding domain capable of recognizing and binding to a second target antigen,
(c) a common light chain antigen-binding domain capable of recognizing and binding to the first or second target antigen,
wherein the heavy chain of (a) or (b) or both (a) and (b) further comprises the heavy chain constant region comprising SEQ ID NO:2 or SEQ ID NO: 30.

In another aspect, at least one of the heavy chains of (a) or (b) in such bispecific antibody hereinabove comprises an amino acid modification at (i) 435R or (ii) 435R and 436F (EU numbering) ((i)95R or (ii) 95R and 96F in the IMGT numbering system).

In other aspects, the antibody is a bispecific antibody wherein the bispecific antibody comprises (a) a first heavy chain comprising an antigen-binding domain capable of recognizing and binding to a first target antigen, and a first heavy chain constant region comprising SEQ ID NO: 1, SEQ ID NO:2, SEQ ID NO: 30, or SEQ ID NO: 31; (b) a second heavy chain comprising an antigen-binding domain capable of recognizing and binding to a second target antigen, and a second heavy chain constant region comprising SEQ ID NO: 38 or SEQ ID NO: 37; and (c) common light chain antigen-binding domain capable of recognizing and binding to the first or second target antigen.

In one embodiment, the antibody is a monovalent antibody. Accordingly, in one embodiment, the antibody is a monovalent antibody, wherein said antibody is constructed by a method comprising : i) providing a nucleic acid molecule encoding the light chain of said monovalent antibody, said construct comprising a nucleotide sequence encoding the $V_L$ region of a selected antigen specific antibody and a nucleotide sequence encoding the constant $C_L$ region of an Ig, wherein said nucleotide sequence encoding the $V_L$ region of a selected antigen specific antibody and said nucleotide sequence encoding the $C_L$ region of an Ig are operably linked together, and wherein the nucleotide sequence encoding the $C_L$ region has been modified such that the $C_L$ region does not contain any amino acids capable of forming disulfide bonds or covalent bonds with other peptides comprising an identical amino acid sequence of the $C_L$ region in the presence of polyclonal human IgG or when administered to an animal or human being; ii) providing a nucleic acid construct encoding the heavy chain of said monovalent antibody, said construct comprising a nucleotide sequence encoding the $V_H$ region of a selected antigen specific antibody and a nucleotide sequence encoding a constant $C_H$ region of a human Ig, wherein the nucleotide sequence encoding the $C_H$ region comprises nucleic acids encoding SEQ ID NO:1, SEQ ID NO:2, SEQ ID NO: 30, SEQ ID NO: 31, SEQ ID NO: 38, or SEQ ID NO: 37, wherein such nucleotide sequence has been modified and does not comprise any amino acid residues which participate in the formation of disulphide bonds or covalent or stable non-covalent inter-heavy chain bonds with other peptides comprising an identical amino acid sequence of the $C_H$ region of the human Ig in the presence of polyclonal human IgG or when administered to an animal, such as a human, wherein said nucleotide sequence encoding the $V_H$ region of a selected antigen specific antibody and said nucleotide sequence encoding the $C_H$ region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the antibody is a monovalent antibody, which comprises: i) a variable region or an antigen-binding domain of said region, and ii) a $C_H$ region of an immunoglobulin or a fragment thereof comprising SEQ ID NO:1, SEQ ID NO:2, SEQ ID NO: 30, SEQ ID NO: 31, SEQ ID NO: 38, or SEQ ID NO: 37, wherein the $C_H$ region or fragment thereof has been modified such that the region does not comprise any amino acid residues which are capable of forming disulfide bonds with an identical $C_H$ region or other covalent or stable non-covalent inter-heavy chain bonds with an identical $C_H$ region in the presence of polyclonal human IgG.

In another further embodiment, the sequence of said monovalent antibody has been modified so that it does not comprise any acceptor sites for N-linked glycosylation.

In general, antibodies described herein may be modified by inclusion of any suitable number of such modified amino acids and/or associations with conjugated substituents. Suitability in this context is generally determined by the ability to at least substantially retain the antibody or antigen binding fragment's selectivity and/or specificity associated. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. The inclusion of one or more modified amino acids may be advantageous in, for example, further increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, N.J.

Antibodies of the invention may also be chemically modified by covalent conjugation to a polymer to, for instance, further increase their circulating half-life. Exemplary polymers, and methods to attach them to peptides, are illustrated in for instance U.S. Pat. Nos. 4,766,106, 4,179, 337, 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

In one embodiment, antibodies comprising one or more radiolabeled amino acids are provided. A radiolabeled antibody may be used for both diagnostic and therapeutic purposes. In another embodiment, antibodies of the present invention may be conjugated to a molecule which is a therapeutic agent or a detectable marker. In one embodiment, the therapeutic agent is a cytotoxic agent, such as a radioisotope. Examples of radioisotopes for polypeptides include, but are not limited to, $^{3}$H, $^{14}$C, $^{15}$N, $^{35}$S, $^{90}$Y, $^{99}$Tc, and $^{125}$I, $^{131}$I, $^{186}$Re, and $^{225}$Ac. Methods for preparing radiolabeled amino acids and related peptide derivatives are known in the art (see for instance Junghans et al., in *Cancer Chemotherapy and Biotherapy* 655-686 (2nd edition, Chafner and Longo, eds., Lippincott Raven (1996)) and U.S. Pat. No. 4,681,581, 4,735,210, 5,101,827, 5,102,990 (US RE35,500), U.S. Pat. Nos. 5,648,471 and 5,697,902. For example, a radioisotope may be conjugated by a chloramine T method. In further embodiments, a detectable marker may be a radiolabel, an enzyme, a chromophore, or a fluorescent label.

In a further aspect, the invention relates to an expression vector encoding a polypeptide, e.g. an antibody, antigen-binding protein or receptor-Fc fusion protein of the invention. Such expression vectors may be used for recombinant production of polypeptides of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an antibody-encoding nucleic acid molecule is comprised in a naked DNA or RNA vector, including, for example, a linear expression element (as described in, for instance, Sykes and Johnston, *Nat Biotech* 12, 355-59 (1997)), a compacted nucleic acid vector (as described in for instance U.S. Pat. No. 6,077,835 and/or WO 00/70087), or a plasmid vector such as pBR322, pUC 19/18, or pUC 118/119. Such nucleic acid vectors and the usage thereof are well known in the art (see, for instance, U.S. Pat. Nos. 5,589,466 and 5,973,972).

In another embodiment, the vector comprises the nucleic acid molecule encoding an antibody or polypeptide of the invention, including an expression vector comprising the nucleic acid molecules described wherein the nucleic acid molecule is operatively linked to an expression control sequence.

In one embodiment, the vector is suitable for expression of a polypeptide or antibody of the invention in a bacterial cell. Examples of such vectors include expression vectors such as BlueScript (Stratagene), pIN vectors (Van Heeke & Schuster, *J Biol Chem* 264, 5503-5509 (1989), pET vectors (Novagen, Madison, Wis.) and the like.

An expression vector may also or alternatively be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH (reviewed in: F. Ausubel et al., ed. Current Protocols in Molecular Biology, Greene Publishing and Wiley InterScience New York (1987), and Grant et al., *Methods in Enzymol* 153, 516-544 (1987)).

A vector comprising a nucleic acid molecule of the invention is provided, wherein the nucleic acid molecule is operatively linked to an expression control sequence suitable for expression in a mammalian host cell.

Expression control sequences are engineered to control and drive the transcription of genes of interest, and subsequent expression of proteins in various cell systems. Plasmids combine an expressible gene of interest with expression control sequences (i.e. expression cassettes) that comprise desirable elements such as, for example, promoters, enhancers, selectable markers, operators, etc. In an expression vector of the invention, antibody-encoding nucleic acid molecules may comprise or be associated with any suitable promoter, enhancer, selectable marker, operator, repressor protein, polyA termination sequences and other expression-facilitating elements.

"Promoter" as used herein indicates a DNA sequence sufficient to direct transcription of a DNA sequence to which it is operably linked, i.e., linked in such a way as to permit transcription of the antibody-encoding nucleotide sequence when the appropriate signals are present. The expression of a antibody-encoding nucleotide sequence may be placed under control of any promoter or enhancer element known in the art. Examples of such elements include strong expression promoters (e. g., human CMV IE promoter/enhancer or CMV major IE (CMV-MIE) promoter, as well as RSV, SV40 late promoter, SL3-3, MMTV, ubiquitin (Ubi), ubiquitin C (UbC), and HIV LTR promoters).

In some embodiments, the vector comprises a promoter selected from the group consisting of SV40, CMV, CMV-IE, CMV-MIE, RSV, SL3-3, MMTV, Ubi, UbC and HIV LTR.

Nucleic acid molecules of the invention may also be operatively linked to an effective poly (A) termination sequence, an origin of replication for plasmid product in *E. coli*, an antibiotic resistance gene as selectable marker, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions).

Selectable markers are elements well-known in the art. Under the selective conditions, only cells that express the appropriate selectable marker can survive. Commonly, selectable marker genes express proteins, usually enzymes, that confer resistance to various antibiotics in cell culture. In other selective conditions, cells that express a flourescent protein marker are made visible, and are thus selectable. Embodiments include beta-lactamase (bla) (beta- lactam antibiotic resistance or ampicillin resistance gene or ampR), bls (blasticidin resistance acetyl transferase gene), bsd (blasticidin-S deaminase resistance gene), bsr (blasticidin-S resistance gene), Sh ble (Zeocin® resistance gene), hygromycin phosphotransferase (hpt) (hygromycin resistance gene), tetM (tetracycline resistance gene or tetR), neomycin phosphotransferase II (npt) (neomycin resistance gene or neoR), kanR (kanamycin resistance gene), and pac (puromycin resistance gene).

In certain embodiments, the vector comprises one or more selectable marker genes selected from the group consisting of bla, bls, BSD, bsr, Sh ble, hpt, tetR, tetM, npt, kanR and pac. In other embodiments, the vector comprises one or more selectable marker genes encoding green fluorescent protein (GFP), enhanced green fluorescent protein (eGFP), cyano fluorescent protein (CFP), enhanced cyano fluorescent protein (eCFP), or yellow fluorescent protein (YFP).

For the purposes of this invention, gene expression in eukaryotic cells may be tightly regulated using a strong promoter that is controlled by an operator that is in turn regulated by a regulatory fusion protein (RFP). The RFP consists essentially of a transcription blocking domain, and a ligand-binding domain that regulates its activity. Examples of such expression systems are described in US20090162901A1, which is herein incorporated by reference in its entirety.

As used herein "operator" indicates a DNA sequence that is introduced in or near a gene in such a way that the gene may be regulated by the binding of the RFP to the operator and, as a result, prevents or allow transcription of the gene of interest, i.e. a nucleotide encoding a polypeptide of the invention. A number of operators in prokaryotic cells and bacteriophage have been well characterized (Neidhardt, ed. Escherichia coli and Salmonella; Cellular and Molecular Biology 2d. Vol 2 ASM Press, Washington D.C. 1996). These include, but are not limited to, the operator region of the LexA gene of E. coli, which binds the LexA peptide, and the lactose and tryptophan operators, which bind the repressor proteins encoded by the LacI and trpR genes of E. coli. These also include the bacteriophage operators from the lambda $P_R$ and the phage P22 ant/mnt genes which bind the repressor proteins encoded by lambda cI and P22 arc. In some embodiments, when the transcription blocking domain of the RFP is a restriction enzyme, such as NotI, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box. In specific embodiments, the operator is preferably placed immediately downstream of the promoter. In other embodiments, the operator is placed within 10 base pairs of the promoter.

In certain embodiments, the operator is selected from the group consisting of tet operator (tetO), NotI recognition sequence, LexA operator, lactose operator, tryptophan operator and Arc operator (AO). In some embodiments, the repressor protein is selected from the group consisting of TetR, LexA, LacI, TrpR, Arc, LambdaC1 and GAL4. In other embodiments, the transcription blocking domain is derived from a eukaryotic repressor protein, e.g. a repressor domain derived from GAL4.

In an exemplary cell expression system, cells are engineered to express the tetracycline repressor protein (TetR) and a protein of interest is placed under transcriptional control of a promoter whose activity is regulated by TetR. Two tandem TetR operators (tetO) are placed immediately downstream of a CMV-MIE promoter/enhancer in the vector. Transcription of the gene encoding the protein of interest directed by the CMV-MIE promoter in such vector may be blocked by TetR in the absence of tetracycline or some other suitable inducer (e.g. doxycycline). In the presence of an inducer, TetR protein is incapable of binding tetO, hence transcription then translation (expression) of the protein of interest occurs. (See, e.g., U.S. Pat. No. 7,435,553, which is herein incorporated by reference in its entirety.)

Another exemplary cell expression system includes regulatory fusion proteins such as TetR-$ER_{LBD}$T2 fusion protein, in which the transcription blocking domain of the fusion protein is TetR and the ligand-binding domain is the estrogen receptor ligand-binding domain ($ER_{LBD}$) with T2 mutations ($ER_{LBD}$T2; Feil et al. (1997) Biochem. Biophys. Res. Commun. 237:752-757). When tetO sequences were placed downstream and proximal to the strong CMV-MIE promoter, transcription of the nucleotide sequence of interest from the CMV-MIE/tetO promoter was blocked in the presence of tamoxifen and unblocked by removal of tamoxifen. In another example, use of the fusion protein Arc2-$ER_{LBD}$T2, a fusion protein consisting of a single chain dimer consisting of two Arc proteins connected by a 15 amino acid linker and the ERLBDT2 (supra), involves an Arc operator (AO), more specifically two tandem arc operators immediately downstream of the CMV-MIE promoter/enhancer. Cell lines may be regulated by Arc2-ERLBDT2, wherein cells expressing the protein of interest are driven by a CMV-MIE/ArcO2 promoter and are inducible with the removal of tamoxifen. (See, e.g., US 20090162901A1, which is herein incorporated by reference.)

In some embodiments, a vector of the invention comprises a CMV-MIE/TetO or CMV-MIE/AO2 hybrid promoter.

The vectors of the invention may also employ Cre-lox tools for recombination technology in order to facilitate the replication of a gene of interest. A Cre-lox strategy requires at least two components: 1) Cre recombinase, an enzyme that catalyzes recombination between two loxP sites; and 2) loxP sites (e.g. a specific 34-base pair bp sequence consisting of an 8-bp core sequence, where recombination takes place, and two flanking 13-bp inverted repeats) or mutant lox sites. (See, e.g. Araki et al. *PNAS* 92:160-4 (1995); Nagy, A. et al. *Genesis* 26:99-109 (2000); Araki et al. *Nuc Acids Res* 30(19):e103 (2002); and US20100291626A1, all of which are herein incorporated by reference). In another recombination strategy, yeast-derived FLP recombinase may be utilized with the consensus sequence FRT (see also, e.g. Dymecki, S. *PNAS* 93(12): 6191-6196).

In another aspect, a gene (i.e. a nucleotide sequence encoding a recombinant polypeptide of the invention) is inserted within an expression-enhancing sequence of the expression cassette, and is optionally operably linked to a promoter, wherein the promoter-linked gene is flanked 5' by a first recombinase recognition site and 3' by a second recombinase recognition site. Such recombinase recognition sites allow Cre-mediated recombination in the host cell of the expression system. In some instances, a second promoter-linked gene is downstream (3') of the first gene and is flanked 3' by the second recombinase recognition site. In still other instances, a second promoter-linked gene is flanked 5' by the second recombinase site, and flanked 3' by a third recombinase recognition site. In some embodiments, the recombinase recognition sites are selected from a loxP site, a lox511 site, a lox2272 site, and a FRT site. In other embodiments, the recombinase recognition sites are different. In a further embodiment, the host cell comprises a gene capable of expressing a Cre recombinase.

In one embodiment, the vector comprises a first gene encoding a light chain of an antibody or a heavy chain of an antibody of the invention, and a second gene encoding a light chain of an antibody or a heavy chain of an antibody of the invention.

In some embodiments, the vector further comprises an X-box-binding-protein 1 (mXBP1) gene capable of enhancing protein production/protein secretion through control of the expression of genes involved in protein folding in the endoplasmic reticulum (ER). (See, e.g. Ron D, and Walter P. *Nat Rev Mol Cell Biol.* 8:519-529 (2007)).

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g. *S. cerevisiae, S. pombe, P. partoris, P. methanolica*, etc.), plant cells, insect cells (e.g. SF-9, SF-21, baculovirus-infected insect cells, *Trichoplusia ni*, etc.), non-human animal cells, human cells, or cell fusions such as, for example, hybridomas or quadromas. In certain embodiments, the cell is a human, monkey, ape, hamster, rat or mouse cell. In other embodiments, the cell is eukaryotic and is selected form the following cells: CHO (e.g. CHO K1, DXB-11 CHO, Veggie-CHO), COS (e.g. COS-7), retinal cells, Vero, CV1, kidney (e.g. HEK293, 293 EBNA, MSR 293, MDCK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In some embodiments, the cell comprises one or more viral genes, e.g. a retinal cell that expresses a viral gene (e.g. a PER.C6® cell).

In an even further aspect, the invention relates to a recombinant eukaryotic or prokaryotic host cell, such as a transfectoma, which produces an antibody of the invention as defined herein or a bispecific molecule of the invention as defined herein. Examples of host cells include yeast, bacterial, and mammalian cells, such as CHO or HEK cells. For example, in one embodiment, the present invention provides a cell comprising a nucleic acid stably integrated into the cellular genome that comprises a sequence coding for expression of an antibody comprising a recombinant polypeptide of the present invention. In another embodiment, the present invention provides a cell comprising a non-integrated (i.e., episomal) nucleic acid, such as a plasmid, cosmid, phagemid, or linear expression element, which comprises a sequence coding for expression of an antibody comprising the recombinant polypeptide of the invention. In other embodiments, the present invention provides a cell line produced by stably transfecting a host cell with a plasmid comprising an expression vector of the invention.

In a further aspect, the invention relates to a method for producing an antibody, or antigen-binding protein, or receptor-Fc fusion protein of the invention, said method comprising the steps of a) culturing a hybridoma or a host cell of the invention as described herein above, and b) purifying the antibody, or antigen-binding protein, or receptor-Fc fusion (supra) from the culture media.

In an even further aspect, the invention relates to a composition comprising: an antibody or antigen-binding fragment thereof, antigen-binding protein or receptor-Fc fusion protein as defined herein, or a bispecific molecule as defined herein.

The compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen antibody of the present invention and the chosen mode of administration. The actual dosage levels of the active ingredients in the pharmaceutical compositions of the present invention may be varied so as to obtain an amount of the active ingredient which is effective to achieve the appropriate stability of drug substance, desired therapeutic response for a particular patient, composition, and mode of administration. The selected dosage level will depend upon a variety of pharmacokinetic factors.

The pharmaceutical composition may be administered by any suitable route and mode. Suitable routes of administering an antibody of the present invention in vivo are well known in the art and may be selected by those of ordinary skill in the art. (Daugherty, A L, and Msrny, R J, *Adv Drug Delivery Rev,* 58(5-6): 686-706 (2006)).

Labeled antibodies of the invention can be used for diagnostic purposes to detect, diagnose, or monitor diseases or disorders. The invention provides for the detection or diagnosis of a disease or disorder, comprising: (a) assaying the existence of antigen in cells or tissue samples of a subject using one or more antibodies that immunospecifically bind to the target antigen; and (b) comparing the level of the antigen with a control level, e.g. levels in normal tissue samples, whereby an increase in the assayed level of antigen compared to the control level of antigen is indicative of the disease or disorder, or indicative of the severity of the disease or disorder.

Antibodies of the invention can be used to assay antigen levels in a biological sample using immunohistochemical methods well-known in the art. Other antibody-based methods useful for detecting protein include immunoassays such as the enzyme linked immunoassay (ELISA) and the radioimmunoassay (RIA). Suitable antibody labels may be used in such kits and methods, and labels known in the art include enzyme labels, such as alkaline phophatase and glucose oxidase; radioisotope labels, such as iodine ($^{125}$I, $^{131}$I) carbon ($^{14}$C), sulfur ($^{35}$S), tritium ($^{3}$H), indium ($^{121}$I), and technetium ($^{99m}$Tc); and luminescent labels, such as luminol and luciferase; and flourescent labels, such as flourescein and rhodamine.

Presence of labeled antibodies may be detected in vivo for diagnosis purposes. In one embodiment, diagnosis comprises: a) administering to a subject an effective amount of a labeled antibody; b) waiting for a time interval following administration for permitting labeled antibody to concentrate at sites where antigen may be detected and to allow for unbound labeled antibody to be cleared to background level; c) determining a background level; and d) detecting the labeled antibody in the subject, such that detection of labeled antibody above the background level is indicative that the subject has the disease or disorder, or is indicative of the severity of the disease or disorder. In accordance with such embodiment, the antibody is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

EXAMPLES

The following examples are provided to describe to those of ordinary skill in the art how to make and use methods and compositions of the invention, and are not intended to limit the scope of what the inventors regard as their invention. Efforts have been made to ensure the accuracy with respect to numbers used (e.g. amounts, concentrations, temperature, etc.) but some experimental errors and deviations should be accounted for.

Example 1

Preparation of the Recombinant Polypeptides

Generating the recombinant polypeptides, for example a chimeric $C_H$ IgG4 (SEQ ID NO: 31) and a chimeric $C_H$ IgG1 (SEQ ID NO: 30), was done using standard cloning techniques. First, the chimeric IgG4 $C_H$ was generated through a two-step PCR amplification process. Two PCR fragments, Fragment 1 and 2, were amplified using starting construct pR85501 (containing a wild-type hIgG4 $C_H$ DNA) and using primers oSP030-oSP031 and oSP032-oSP033 (see Table 8), respectively. The primers introduced the desired IgG2 lower hinge sequence (which encodes SEQ ID NO:3) and the flanking restriction sites into the fragments. These two fragments were then joined using PCR primers oSP031 and oSP033. The resulting sequence was inserted into pR85501via XhoI-NotI restriction sites generating a vector construct pR85502 that contains a chimeric IgG4 $C_H$ having an IgG2 lower hinge sequence. The sequence was confirmed using primers KO_oLRC120 and oKO021.

In addition, a chimeric IgG1 $C_H$ was generated through multiple step PCR amplification. Fragment 1a was generated using primers oSP031 and oSP035 (see Table 8 below) from template pR85503 (which contains a wild-type human IgG1 $C_H$ DNA). Fragment 2a was amplified with primers oSP036 and oSP038 using pR85502 (containing the chimeric IgG4 $C_H$ DNA) as a template. Fragment 3 was made using primers oSP037 and oSP039 from template pR85503 (wild-type hIgG1 $C_H$ DNA). Fragments 1a and 2a were joined using primers oSP031 and oSP038, which generated Fragment 4. Joining Fragments 2a and 3 using primers oSP036 and oSP039 created Fragment 5. Fragment 4 and 5 were then fused using primers oSP031 and oSP039. The resulting sequence was inserted into pR85501 via XhoI-NotI restriction sites generating a construct pR85504 that has an IgG1 constant region with the IgG2 lower hinge and IgG4 CH2 domain. The sequence was confirmed using primers KO_oLRC120 and oKO021.

TABLE 8

Primers for PCR generation of chimeric $C_H$ nucleic acid constructs

| Primer name | Primer Sequence (SEQ ID NO) |
| --- | --- |
| oSP030 | 5'-TTCGCGCAGCTTAGGTTTATGCCAGGGGGGACGGGTGGCACGGGTCGTGGTGGACACCGT-3' (antisense)(SEQ ID NO: 16) |
| oSP031 | 5'-AAGCTTATACTCGAGCTCTAGATTGGGAACCCGGGTCTCT-3' (SEQ ID NO: 17) |
| oSP032 | 5'-CCCACCGTGCCCAGCACCACCTGTGGCAGGACCATCAGTCTTCCTGTTCCCCCCAAAA-3' (SEQ ID NO: 18) |
| oSP033 | 5'-TGTGTCTTCAGGGAGAGGGACAGAGACCCATTTACTCGCC GGCG-3' (antisense) (SEQ ID NO: 19) |
| oSP035 | 5'-CTCGGGTTTAGAACACTGTTTTGAGTGTGTACGGGTGGCACGGGTCGTGGTGGACACCGT-3' (antisense)(SEQ ID NO: 20) |
| oSP036 | 5'-AAATCTTGTGACAAAACTCACACATGCCCACCGTGCCCAGCACCACCTGTG-3' (SEQ ID NO: 21) |
| oSP037 | 5'-GAGAAAACCATCTCCAAAGCCAAAGGGCAGCCCCGAGAACCACAGGTGTACACC-3' (SEQ ID NO: 22) |
| oSP038 | 5'- CTCTTTTGGTAGAGGTTTCGGTTTCCCGTCGGGGCTCTTG GTGTCCACATGTGG-3' (antisense) (SEQ ID NO: 23) |
| oSP039 | 5'-CTTCAGGGAGAGGGACAGAGGCCCATTTACTCGCCGGCG-3' (antisense) (SEQ ID NO: 24) |
| KO_oLRC120 | 5'-GCTGACAGACTAACAGACTG-3' (SEQ ID NO: 25) |
| KO_Fc-4-3 | 5'-GACCTCAGGGGTCCGGGAGATCAT-3' (SEQ ID NO: 26) |
| oKO021 | 5'-ATACATTATACGAAGTTATACCGGTA-3' (SEQ ID NO: 27) |
| oKO014 | 5'- GTGAGCGCTCTTCGGCAGACGTCCAACTGGTGCAGTCAGGG-3' (SEQ ID NO: 39) |
| oKO015 | 5'-CAGCTAGCTCTTCCGGCTGAGGAGACGGTGACCGTGGTGCCTTGGCC-3' (SEQ ID NO: 40) |

Example 2

Generation of Chimeric Heavy Chain Antibodies

Exemplary antibodies were obtained using standard methodologies. An anti-hCD3 antibody (anti-hCD3 antibody "L2K") was used to construct the chimeric antibodies of this example. L2K was obtained by well-known methods based on WO2004/106380. Anti-hCD3_L2K, designated herein as Control Antibody 1, contains a wild-type human IgG1 heavy chain constant region (SEQ ID NO:13).

The bispecific antibodies created in accordance with the present Example comprise two separate antigen-binding domains (i.e., binding arms). An anti-hCD3 x anti-hCD20 (Bispecific antibody), designated herein as Control Antibody 2, was obtained as described in US Patent Application Publication No. US20100331527A1. The bispecific antibody was constructed using standard methodologies wherein a heavy chain and a light chain from an "L2K" anti-CD3 antibody of WO2004/106380 were combined with a heavy chain from an anti-CD20 antibody (see e.g. PCT International Application No. PCT/US13/60511, filed on Sep. 19, 2013, which is herein incorporated by reference in its entirety). Control Antibody 2 contains wild-type human IgG4 heavy chain constant regions (SEQ ID NO:15), yet the anti-CD3 arm has a modified CH3 domain (SEQ ID NO:42) for ease of purification.

Control Antibody 3 was obtained using the same methodologies as described herein to combine the variable regions of Control Ab 2 (Anti-hCD3×anti-hCD20 Bispecific Ab) with a wild-type human IgG1 heavy chain constant regions (SEQ ID NO:13), having a modified CH3 domain (SEQ ID NO:41) in the anti-CD3 heavy chain arm.

Control Antibody 4 contains an antigen-binding domain capable of binding CA9 antigen and a wild-type human IgG1 heavy chain constant region (SEQ ID NO:13).

Control Antibody 5 is an anti-hCD3 x anti-hCD20 bispecific antibody obtained according to the methods of PCT International Application No. PCT/US13/60511, filed on Sep. 19, 2013, which is herein incorporated by reference in its entirety. Briefly, a first antigen-binding domain comprising a heavy chain variable region derived from an anti-CD20 antibody ("CD20-VH") is paired with a light chain variable region derived from an anti-CD3 antibody ("CD3-VL"). The CD20-VH/CD3-VL pairing creates an antigen-binding domain that specifically recognizes CD20. A second antigen-binding domain comprising a heavy chain variable region derived from an anti-CD3 antibody ("CD3-VH") is paired with a light chain variable region derived from an anti-CD3 antibody ("CD3-VL"). The CD3-VH/CD3-VL pairing creates an antigen-binding domain that specifically recognizes CD3. Control Antibody 5 is engineered with wild-type human IgG1 heavy chain constant regions (SEQ ID NO:13), yet the anti-CD3 arm has a modified CH3 domain (SEQ ID NO:41) in the heavy chain constant region for ease of purification.

Isotype controls were made that do not bind to the same target antigen as the tested antibodies, e.g. do not bind CD3 or CD20 antigen. Wild-type IgG1 Isotype Control contains the wt heavy chain constant region amino acid sequence of SEQ ID NO:13. Wild-type IgG4 "CPPC" Isotype Control has the wt CH amino acid sequence of SEQ ID NO:15, except having the "CPPC" hinge mutation S228P (according to EU numbering).

The constant region of Control Antibody 1 was replaced with a chimeric human constant region of the invention, e.g SEQ ID NO: 31 or SEQ ID NO: 30. Replacement of the constant region was done by obtaining a L2K variable region nucleic acid sequence (plasmid pR85505) that was amplified using primers oKO014 and oKO015 (see Table 8). The L2K variable region (SEQ ID NO: 34) was then introduced into plasmid pR85502 using Sap1 restriction site for cloning. The sequence of the resulting plasmid pR85506 was confirmed using primers KO_oLRC120 and oKO_Fc_4-3. This construct was used to generate Antibody 1 of the invention, sIgG4-anti-CD3_L2K (also known herein as sIgG4) (which comprises SEQ ID NO:31), using standard methodologies for isolating antibodies.

In a second example, the L2K variable region was amplified using primers oKO014 and oKO015 (see Table 8) using plasmid pR85505 as template. The variable region was then introduced into plasmid pR85504 using Sap1 restriction site for cloning. The sequence of the resulting plasmid pR85507 was confirmed using primers KO_oLRC120 and oKO_Fc_4-3. This construct was used to generate Antibody 2 of the invention, sIgG1-anti-CD3_L2K (also known herein as sIgG1) (which comprises SEQ ID NO:30), using standard methodologies.

Antibody 3 was constructed from the anti-CD3 x anti-CD20 bispecific antibody of Control Antibody (Ab) 5. Control Ab 5 had its heavy chain constant regions replaced with chimeric constant heavy chain regions, the anti-CD20 arm having an heavy chain constant region amino acid sequence comprising SEQ ID NO: 30, and the anti-CD3 arm having a mutation in the CH3 domain of the CH (SEQ ID NO:37) to create Antibody 3 (also known herein as sIgG1*).

Similarly, Antibody 4 was created from bispecific antibody Control Ab 5 whereas heavy chain constant regions were replaced with chimeric CH, the anti-CD20 arm having an heavy chain constant region amino acid sequence comprising SEQ ID NO: 31, and the anti-CD3 arm having a mutation in the CH3 domain of the CH (SEQ ID NO:38) to create Antibody 4 (also known herein as sIgG4*).

The chimeric antibodies comprising constant regions of SEQ ID NO:30 or SEQ ID NO:31 (or bispecific antibodies comprising SEQ ID NO:30/37 or SEQ ID NO:31/38), and the control antibodies, were used in certain experiments set out in the Examples that follow.

Example 3

Chimeric Antibodies Specifically Bind to Jurkat cells

After chimeric antibodies were converted to fully human IgGs, specific antigen binding properties were determined. The example antibody constructs and control antibodies, as set forth in Example 2, were tested using fluorescence-activated cell sorting (FACS) for their ability to bind to Jurkat cells (human T-cell line expressing target antigens CD3+, CD20). FACS data was acquired using the following protocol: Cells at $2 \times 10^5$ per well were incubated with serially diluted antibodies and 100 µl supplements for 1 hour at 4° C. Post incubation, cells were washed twice and appropriate secondary antibodies (e.g. fluorescent-tagged FITC anti-human IgG) were added and incubated for an additional 30 minutes at 4° C., then washed twice. Cells were re-suspended in cold PBS containing 1% BSA and analyzed by flow cytometry on a FACSCanto II™ flow cytometer (BD Biosciences). Jurkat cells were gated by side and forward scatter sorting. Each $EC_{50}$ for cell binding titration was determined using Prism (GraphPad Software, San Diego, Calif.) with values calculated using a 4-parameter non-linear regression analysis.

Figure 6B:
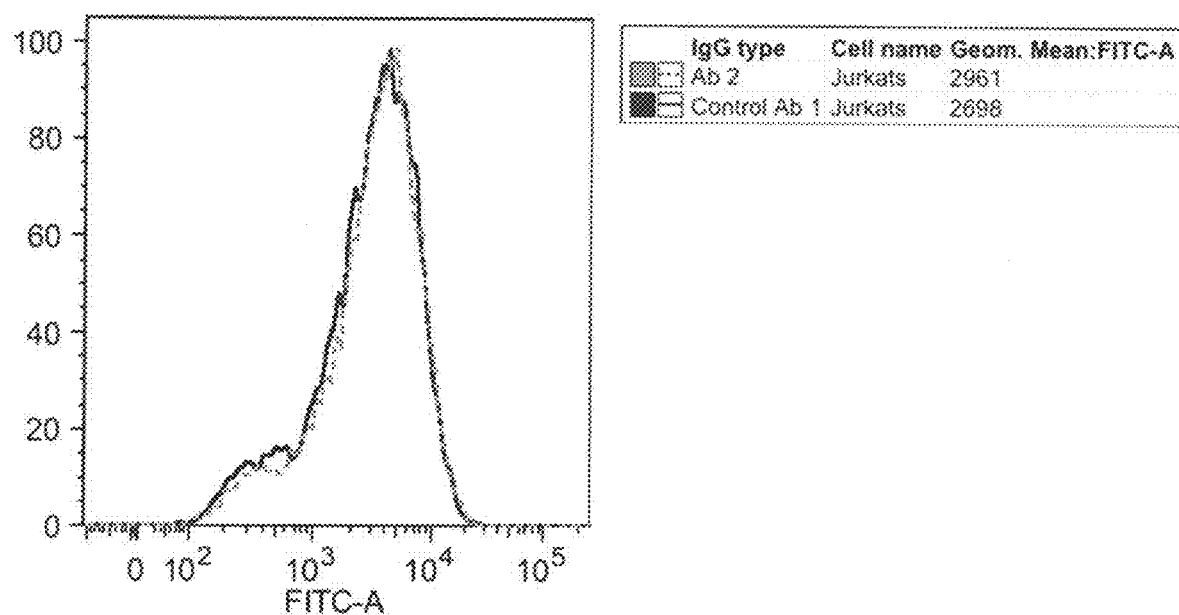
Figure 6C:
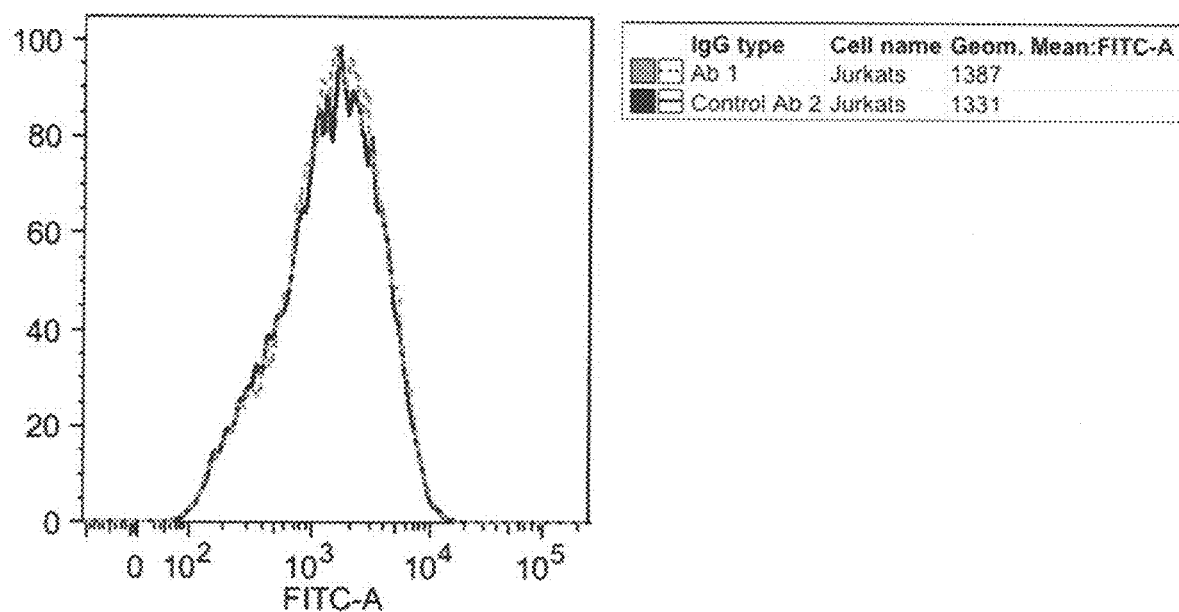

It was determined that chimeric antibodies bind to Jurkat cells at equal concentrations compared to control antibodies having a wild-type $C_H$ region, therefore chimeric antibodies with altered $C_H$ regions have not lost their ability to bind antigen. See FIG. 6.

Example 4

Characterization of Antibodies-Binding to U937 Cells

Figure 7:
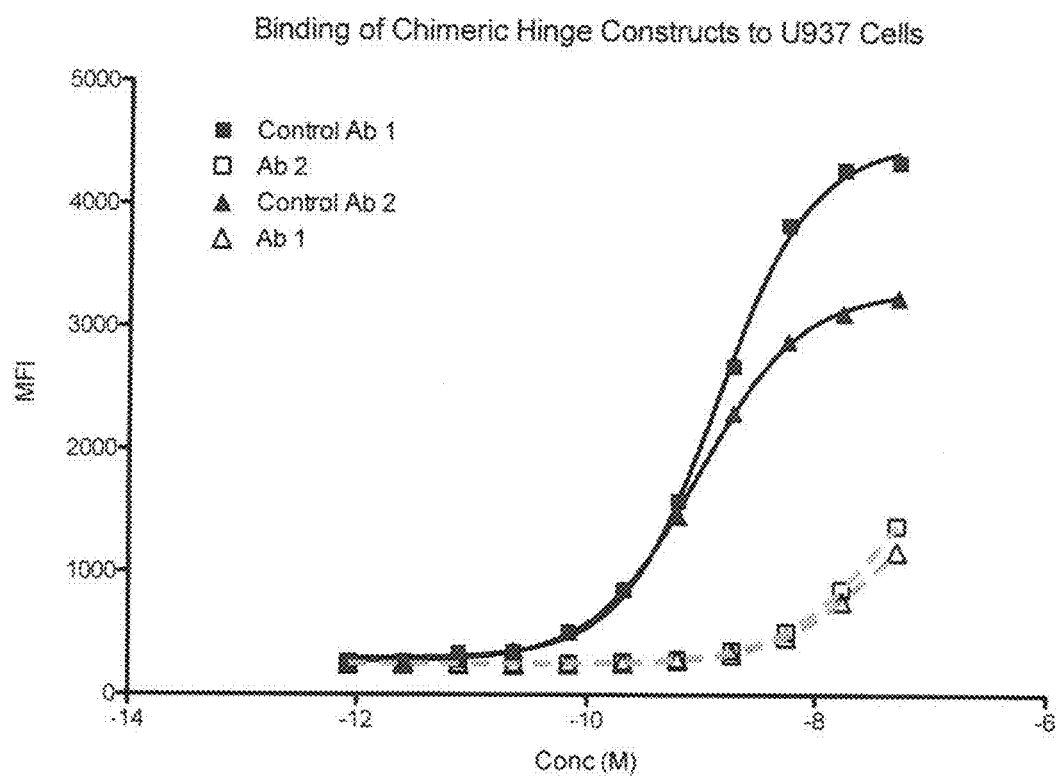
FIG. 7. Dose-response curve depicting chimeric hinge antibody ability to bind U937 cells. Half-maximal concentration ($EC_{50}$) values with respect to binding (mean fluorescence intensity) are given. (Control antibody 1=wt IgG1 $C_H$; Antibody 2=sIgG1; Control Ab2=wt IgG4 $C_H$; and Antibody 1=sIgG4.)

U937 cells, a monocyte cell line expressing FcγRI and FcγRIIA, were plated and allowed to incubate with serial dilutions of Ab (the highest concentration of Ab used is 50 nM). Cells were incubated with Abs for 1 hr at 4° C. then washed twice. U937 cells were then incubated with secondary Ab (FITC goat anti-human Fab) for 30 min at 4° C. then washed twice. Cells were analyzed by flow cytometry using standard methods and median fluorescent intensity (MFI) was recorded. Results are summarized in Table 9 and FIG. 7 where it is demonstrated that chimeric Abs, Antibody 1 (sIgG4) and Antibody 2 (sIgG1), bind to U937 cells at high concentrations.

TABLE 9

Binding of Chimeric Abs vs. Wild-type Abs to U937 cells

| Antibody (Ab) | $EC_{50}$ (nM) |
| --- | --- |
| Control Ab 1 | 1.3 |
| sIgG1 (Ab2) | 45.4 |
| Control Ab 2 | 0.91 |
| sIgG4 (Ab 1) | 33.5 |

Example 5

Characterization of Antibodies-U937 Cytotoxic Assay

Figure 8:
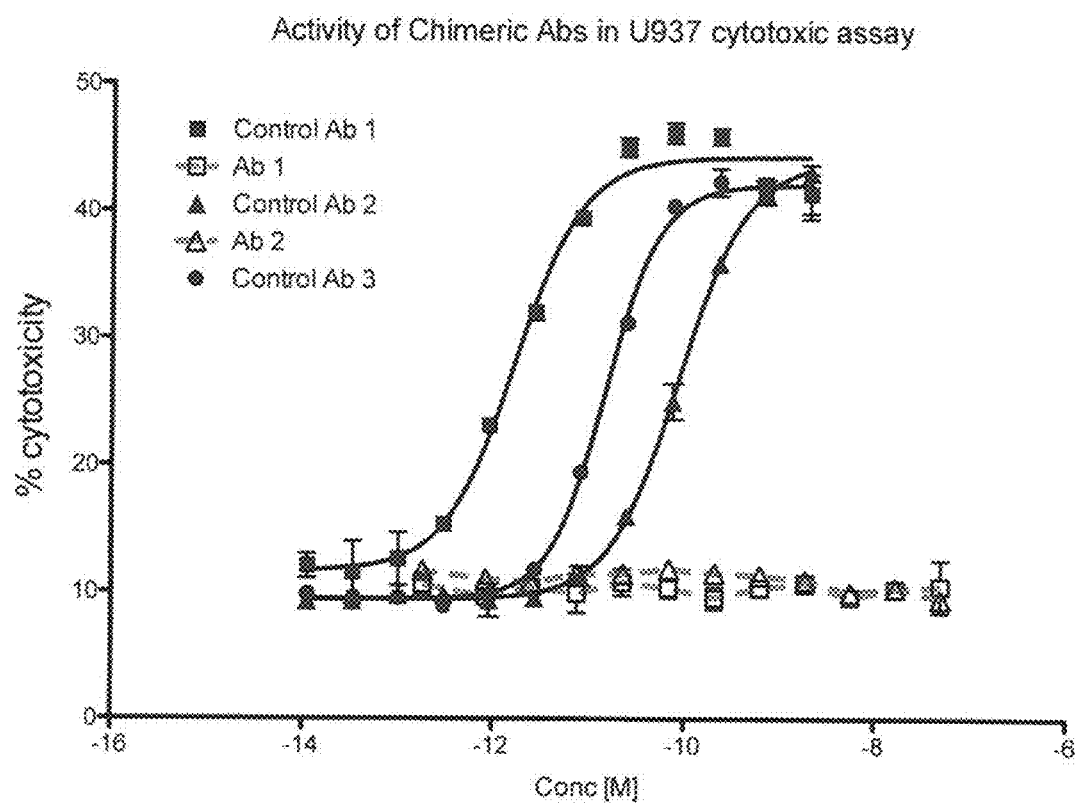
FIG. 8. Dose-response curve depicting chimeric hinge antibody lack of cytotoxicity with respect to U937 cells in the presence of activated PBMCs (T cells). Half-maximal concentration ($EC_{50}$) values with respect to % cytotoxicity are reflected. (Control antibody 1=wt IgG1 $C_H$; Antibody 1=sIgG4; Control Ab 2=wt IgG4 $C_H$; and Antibody 2=sIgG1; Control Ab 3=wt IgG1 $C_H$.)

U937 cells were used as a positive killer effector control in the following cytoassay. As such, the ability of antibodies with chimeric $C_H$ regions to kill U937 cells via Fc/FcγR interactions was tested. Calcein killing assays were carried out using the following protocol: Human and cynomolgus Peripheral Blood Mononuclear Cells (PBMCs) were isolated over Ficoll-Paque (GE Healthcare Life Sciences) or via Lympholyte-Mammal density cell separation media (Cedarlane Laboratories), respectively. The isolated PBMCs were activated over a course of several days with media containing recombinant human IL-2 (30 U/ml) and T-cell activation beads (anti-CD3/CD28 for human PBMC, anti-CD2/CD3/CD28 for cynomolgus PBMC). Activated T-cells were isolated from the PBMCs by centrifugation, then resuspended in 1 ml media. The magnetized beads were removed from the T-cells. Target cells (U937) were labeled with calcein, then washed and followed by incubation with the isolated activated T-cells (10:1 effector: target ratio) and antibody, using 3-fold serial dilutions of antibody over a course of 3 hours at 37° C. Following incubation, the plates were centrifuged and supernatants were transferred to a translucent black clear bottom plate for fluorescence analysis. Each $EC_{50}$, defined as the molar concentration of antibody that induces 50% cytotoxicity, was determined using Prism (GraphPad Software, San Diego, Calif.). Values were calculated using a 4-parameter non-linear regression analysis. Results are summarized in FIG. 8.

The cytotoxic activity of Antibody 1 (sIgG4) and Antibody 2 (sIgG1) is significantly diminished as compared to corresponding antibodies containing wild-type IgG4 and IgG1 hinge regions. See FIG. 8. Interestingly, although the chimeric Abs weakly bind at higher concentrations as shown in Example 4, they do not kill U937 cells in the cytoassay.

Example 6

Characterization of Antibodies-Proliferation of hPBMCs

Figure 9:
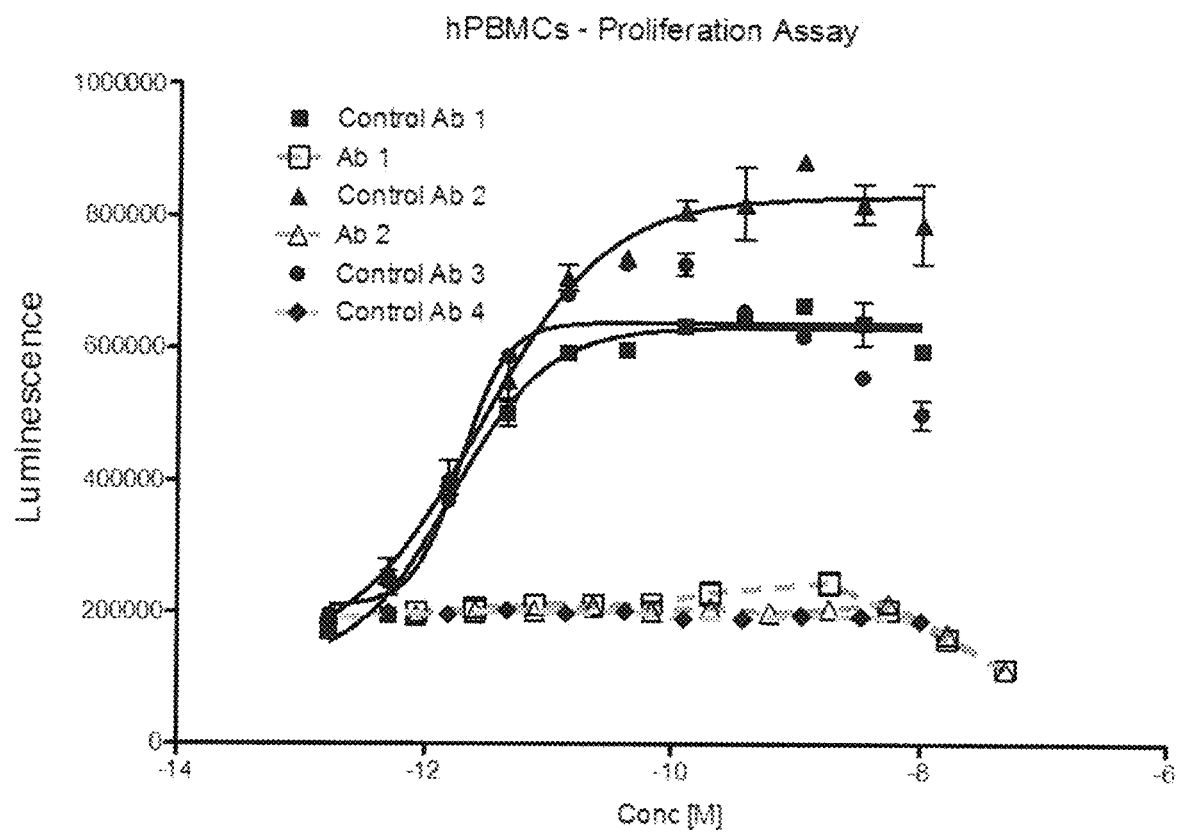
FIG. 9. Dose-response curve depicting the half-maximal concentration ($EC_{50}$) with respect to cell viability in a PBMC proliferation assay. (Control antibody 1=wt IgG1 $C_H$; Antibody 1=sIgG4; Control Ab 2=wt IgG4 $C_H$; Antibody 2=sIgG1; Control Ab 3=wt IgG1 $C_H$; and Control Ab 4=non-specific Ab with wt IgG1 $C_H$).

The ability of chimeric antibodies and control constructs to stimulate Peripheral Blood Mononuclear Cells (PBMCs) and induce proliferation was assessed using ATP catalyzed quantification (CellTiter Glo®). The activation of PBMCs results in the release of cytokines, which drive cellular proliferation. Proliferation data was acquired using the following protocol: Human or cynomolgus monkey derived PBMC ($5 \times 10^5$/well) were incubated with a 3-fold serial dilution of anti-CD20×CD3 or Control antibody (including Control Ab 4 specific to CA9 antigen) in 96 well plates for 72 h at 37° C. Following incubation, CellTiter Glo® was added and luminescence was measured using a VICTOR X5 multi-label plate reader (PerkinElmer). The $EC_{50}$ of cell viability (ATP catalyzed quantification) was determined using Prism (GraphPad Software, San Diego, Calif.). Values were calculated using a 4-parameter non-linear regression analysis and are shown in FIG. 9.

Antibody 1 (sIgG4) and Antibody 2 (sIgG1) do not activate cellular proliferation in comparison to corresponding antibodies containing wild-type IgG4 and IgG1 hinge regions. See FIG. 9.

Example 7

Surface Plasmon Resonance Derived Binding Affinities and Kinetic Constants of Chimeric Antibodies The anti-CD3×anti-CD20 bispecific antibodies having chimeric constant heavy chain regions sIgG1* (Antibody 3) and sIgG4* (Antibody 4) were analyzed using Surface Plasmon Resonance (SPR) (Biacore) technology to determine their kinetic binding parameters to human and cynomolgus Fcγ receptors. Isotype controls, namely wt-IgG1 Isotype Control and wt-IgG4 CPPC Isotype Control, were tested in a similar manner.

Briefly, SPR experiments were performed at 25° C. on a Biacore T200 instrument employing a carboxymethyl dextran-coated (CM-5) chip. A mouse monoclonal anti-penta-histidine antibody (GE Healthcare) was immobilized on the surface of the CM-5 sensor chip using standard amine-coupling chemistry. 140RU-376RU of His-tagged human or monkey FcγR proteins were captured on the anti-penta-histidine amine-coupled CM-5 chip and stock solutions of antibodies were injected at 20 μl/min for 2.5 min over the captured proteins. mAb binding response was monitored and, for low affinity receptors, steady-state binding equilibrium was calculated. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D(M) = k_d/k_a$; and $t_{1/2}$ (min) = $(\ln 2/(60*k_d)$.

TABLE 10

Kinetic binding parameters for wild-type (wt) and chimeric heavy chain antibodies
Binding to His-captured human FcγRI at 25° C.

| Antibody | $k_a$ (M$^{-1}$sec$^{-1}$) | $k_d$ ($^1$sec$^{-1}$) | $K_D$ (10$^{-9}$M) | T$^{1/2}$ (min) |
|---|---|---|---|---|
| wt-IgG1 Isotype Control | 1.74E+05 | 7.48E−04 | 4.3 | 15 |
| wt-IgG4 CPPC Isotype Control | 1.71E+05 | 2.36E−03 | 13.9 | 5 |
| sIgG1* (Ab 3) | NB | NB | NB | NB |
| sIgG4* (Ab 4) | NB | NB | NB | NB |

NB: No binding

As the results in Table 10 demonstrate, sIgG1* and sIgG4* bispecific antibodies display no binding to human FcγRI, compared to antibodies having the wild-type (wt) hIgG1 or hIgG4-CPPC CH region. Chimeric heavy chain antibodies of this invention also display weak to no binding for several of the low-affinity FcRγ receptors (e.g. FcRγIIa, FcRγIIb) compared to antibodies with wt hIgG1 or hIgG4-CPPC Fc sequence (Table 11).

TABLE 11

Steady-state equilibrium binding for wild-type (wt) and chimeric heavy chain antibodies
Binding to His-captured low-affinity human and cynomolgus FcγR receptors at 25° C.

$K_D$ (10$^{-6}$ M) Values for Low Affinity FcγR Binding to Chimeric Heavy Chain Antibodies

| Antibody Tested | human hFcγRIIA (H131) | human FcγRIIA (R131) | cynomolgus FcγRIIA | human FcγRIIB | cynomolgus FcγRIIB | human FcγRIIIA (V176) | human FcγRIIIA (F176) | cynomolgus FcγRIIIA | human FcγRIIIB |
|---|---|---|---|---|---|---|---|---|---|
| wtIgG1 Isotype Control | 1.1 | 2 | 4.2 | 2 | 4.2 | 1.5 | 1.3 | 0.6 | 2.3 |
| wtIgG4 (CPPC) Isotype Control | 12 | 10 | 19.3 | 9.8 | 9.6 | 10 | 26 | 5.8 | NB |
| sIgG1* (Ab 3) | 11.7 | 20.5 | 23.5 | 233 | 14.6 | NB | NB | 42.4 | NB |
| sIgG4* (Ab 4) | 12 | 19.3 | 23.1 | 123 | 13.9 | NB | NB | 66.3 | NB |

NB: No binding

Example 8

IgG1 and IgG4 Antibodies Having Chimeric CH Regions Show Decreased Effector Function in CDC Assay Antibodies with chimeric CH regions (sIgG1* and sIgG4*), as described above, were generated to produce mAbs with altered or reduced effector function. Compared to antibodies comprising a wild-type (wt) heavy chain constant region of the IgG1 isotype, amino acid substitutions in the CH region may hinder the ability of an Ig Fc to bind to its receptor. Hence, signaling and immune responses, such as B cell activation or phagocytosis, may be altered. The effect of amino acid modifications in the CH region on complement dependent cytoxicity (CDC) (in this example) and antibody-dependent cytoxicity (ADCC) effector function (see Example 9) was examined.

To examine the effect of Antibody 3 (sIgG1*) and Antibody 4 (sIgG4*) on CDC effector function, CD20-expressing Raji (target) cells (5000/well) or Daudi cells were plated in the presence of 5% human serum complement. Serial dilutions of sIgG1*, sIgG4* and control antibodies, starting at 100 nM, were added to cells for 4 h at 37° C. Target cell lysis was determined using the CytoTox Glo™ kit (Promega) and percent cytoxicity was calculated.

Figure 10A:
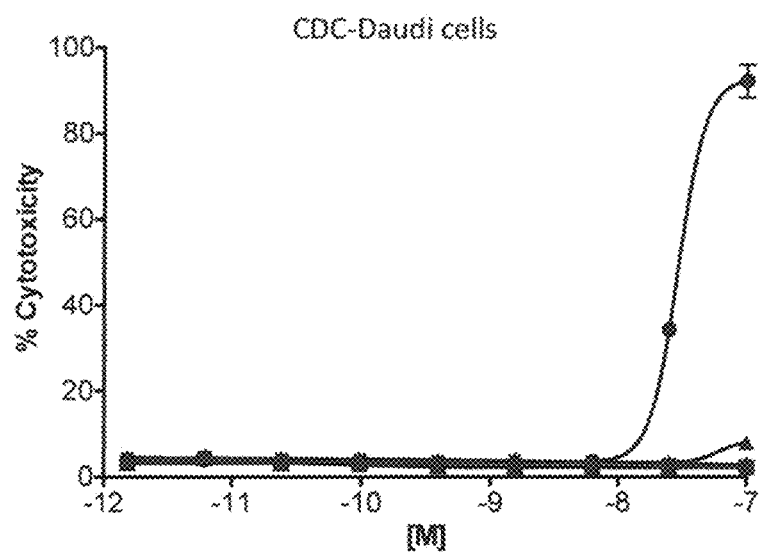
FIGS. 10A and 10B. Dose-response curves depicting lack of CDC activity with respect to Daudi (FIG. 10A) and Raji (FIG. 10B) cells in the presence of antibodies having wild-type or chimeric hinge $C_H$ regions. (Control antibody 5=Bispecific Ab with wt IgG1 $C_H$; Antibody 3=sIgG1*; Antibody 4=sIgG1*; IgG1 Isotype Control=nonspecific Ab with wt IgG1 $C_H$.)
Figure 10B:
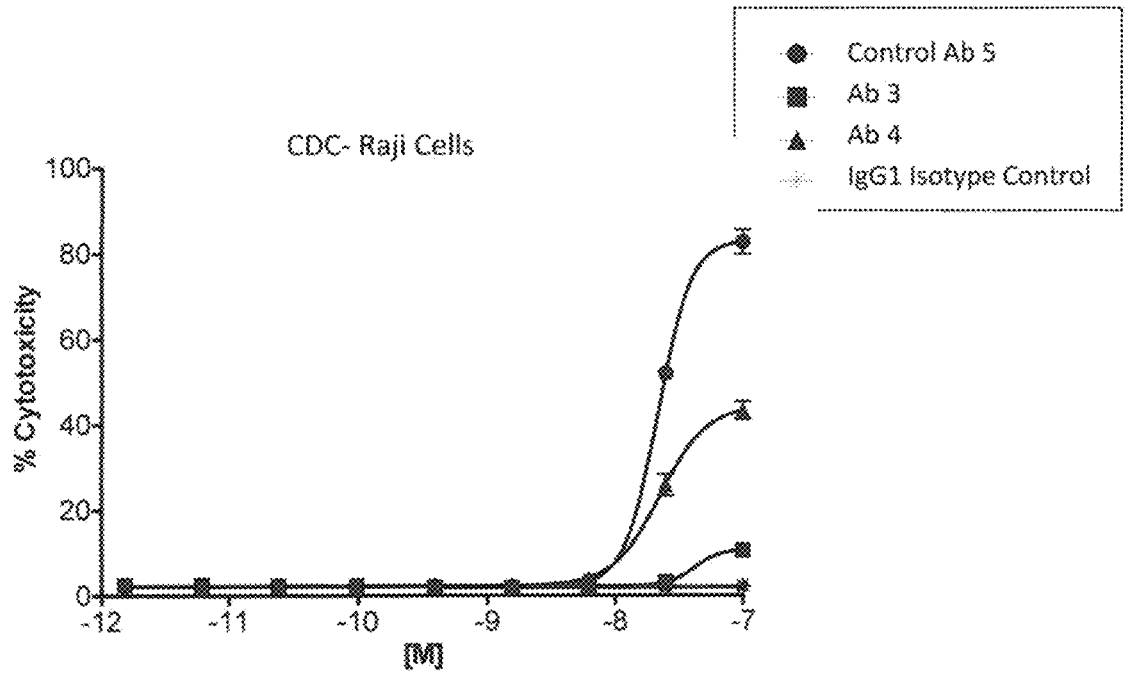

Percent cytoxicity was calculated using the equation: % cytotoxicity=(($L_S$−$L_{SR}$)/($L_{MR}$−$L_{SR}$))*100% where $L_{SR}$ is baseline target cell luminescence and $L_{MR}$ is maximal calcein release from cells lysed by digitonin. The EC$_{50}$ for cytotoxicity was determined using Prism software (GraphPad). Values were calculated using 4-parameter non-linear regression analysis and are shown in Table 12, and FIGS. 10A and 10B.

The CDC activity of Antibody 3 (sIgG1*) and Antibody 4 (sIgG4*) against Daudi and Raji cells is significantly diminished as compared to corresponding antibody having a wt heavy chain constant domain. See Table 12, and FIGS. 10A/B. Some CDC activity was observed with sIgG4* against Raji cells, however, overall results show that the chimeric antibodies mount weaker effector responses than wt IgG1 Fc control antibodies.

TABLE 12 sIgG1* and sIgG4* antibodies display reduced activity in CDC
assays measuring effector function

CDC

| | Target Cell: | | | |
|---|---|---|---|---|
| | Daudi | | Raji | |
| | EC50 [M] | Maximum Cytotoxicity (%) | EC50 [M] | Maximum Cytotoxicity (%) |
| Control Ab 5 | 6.12E−08 | ~95 | 1.98E−08 | ~85 |
| Ab 3 (sIgG1*) | NA | NA | 3.49E−08 | ~10 |
| Ab 4 (sIgG4*) | NA | NA | 2.86E−08 | ~45 |

NA: No activity

Example 9

Figure 11A:
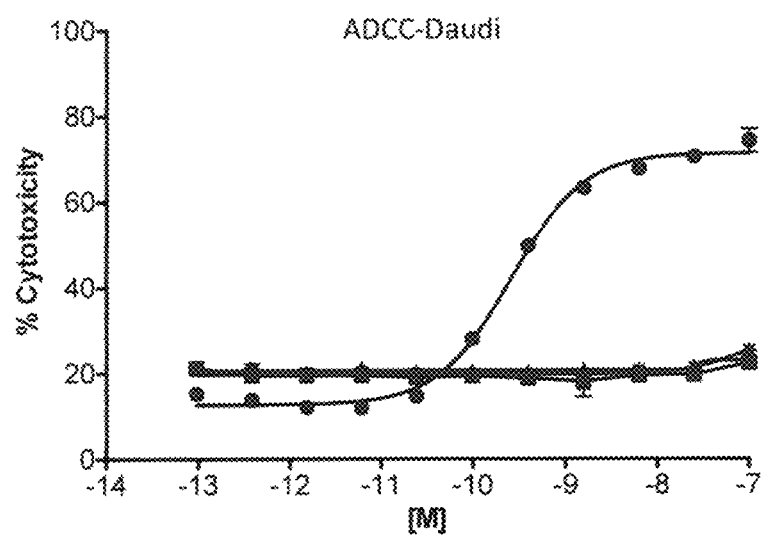
FIGS. 11A and 11B. Dose-response curves depicting lack of ADCC activity with respect to Daudi (FIG. 11A) and Raji (FIG. 11B) cells in the presence of antibodies having wild-type or chimeric hinge $C_H$ regions. (Control antibody 5=Bispecific Ab with wt IgG1 $C_H$; Antibody 3=sIgG1*; Antibody 4=sIgG1*; IgG1 Isotype Control=nonspecific Ab with wt IgG1 $C_H$.)
Figure 11B:
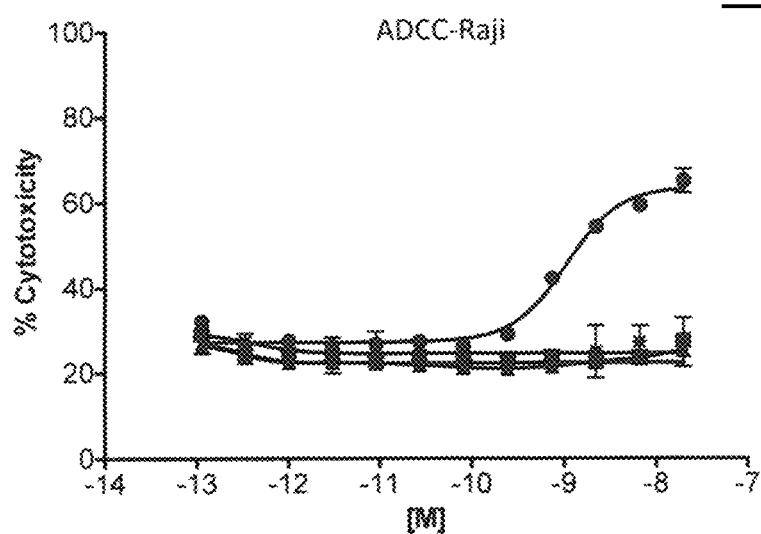

IgG1 and IgG4 Antibodies Having Chimeric CH Regions Show Decreased Effector Function in ADCC Assay To examine the effect of Antibody 3 (sIgG1*) and Antibody 4 (sIgG4*) vs. antibodies with wild-type CH regions on ADCC effector function, freshly isolated unstimulated CD56-positive NK cells or NK92 cells engineered to express the higher affinity V allele of FcγRIIIa were plated with Calcein-labeled CD20-positive Raji or Daudi cells in the presence of chimeric CH-antibodies and wt-CH control antibodies. Calcein release from target cells was monitored and percent cytoxicity was determined. Percent cytotoxicity and $EC_{50}$ were calculated as described for CDC assay, above. Results are shown in Table 13 and FIGS. 11A and 11B.

The chimeric CH antibodies, sIgG1* and sIgG4*, do not mediate ADCC activity (Table 13) against Raji or Daudi cells.

TABLE 13 sIgG1* and sIgG4* antibodies display reduced activity in ADCC assays measuring effector function
ADCC

| | Target Cell: | | | |
|---|---|---|---|---|
| | Daudi | | Raji | |
| | EC50 [M] | Maximum Cytotoxicity (%) | EC50 [M] | Maximum Cytotoxicity (%) |
| Control Ab 5 | 1.87E−10 | ~70[#] | 1.48E−09 | ~65[#] |
| Ab 3 (sIgG1*) | NA | NA | NA | NA |
| Ab 4 (sIgG4*) | NA | NA | NA | NA |

NA: No activity;
[#]background cytotoxicity ~20%

Example 10

Pharmacokinetic Profile of Chimeric Antibodies

The toxicokinetic profile of Antibody 3 (also known herein as sIgG1*) and Antibody 4 (also known herein as sIgG4*) was evaluated by obtaining blood samples from male cynomolgus monkeys (3 animals/treatment group) receiving a single 30-minute IV infusion, followed by a 12-week observation period. Blood samples for toxicokinetic analysis of total drug concentrations in serum were collected pre-dose and post-dose at 5 minutes, and 5, 24, 48, 72 and 168 hours, and Day 14, 21, 35, 49, 66 and 84. The resultant serum samples were analyzed by a direct enzyme linked immunosorbent assay (ELISA) to determine the total drug concentration of the sIgG1* or sIgG4* antibody. The toxicokinetics of the test articles were assessed using non-compartmental analysis (Phoenix WinNonLin) to determine pharmacokinetic parameters. Results are shown in Table 14 (AUC=area under the concentration vs. time curve; $C_{max}$=observed maximum concentration in serum).

TABLE 14

Pharmacokinetic Profile of Chimeric Antibodies in Serum of Cynomolgus monkeys Following a Single Intravenous Infusion to Cynomolgus Monkeys

| | | 1 mg/kg sIgG1* | | 1 mg/kg sIgG4* | |
|---|---|---|---|---|---|
| Parameter | Units | Mean | SD | Mean | SD |
| $C_{max}$ | μg/mL | 33.4 | 3.79 | 26.0 | 4.72 |
| $C_{max}$/Dose | kg*μg/mL/mg | 33.4 | 3.79 | 26.0 | 4.72 |
| $t_{max}$ | day | 0.0243 | 0 | 0.0243 | 0 |
| $AUC_{0-168\,h}$ | day · μg/mL | 100 | 20.1 | 61.1 | 8.04 |
| $AUC_{0-168\,h}$/Dose | day*kg*ug/mL/mg | 100 | 20.1 | 61.1 | 8.04 |
| T1/2 | Day | 8.14 | 1.15 | 14.0 | 2.64 |

Following a single intravenous dose of 1.0 mg/kg of sIgG1* and sIgG4* in cynomolgus monkeys, mean peak concentrations ($C_{max}$) of 33.4 and 26.0 μg/mL, respectively, and mean $AUC_{0-168h}$ values of 100 and 61.1 day*ug/mL, respectively, were observed. The apparent terminal half-life was estimated to be between 8.14-14.0 days of these two molecules. The data indicate that continuous exposure to sIgG1* and sIgG4* was maintained in all animals for the majority of the 12-week observation period and exposure was comparable across treatment groups. No apparent immunogenicity with the test articles was observed. The overall pharmacokinetic profiles of sIgG1* and sIgG4* are typical of monoclonal antibodies dosed in cynomolgus monkey.

What is claimed:

1. An antibody comprising a heavy chain constant (CH) region comprising, from N-terminus to C-terminus, a CH1 domain, a hinge, a CH2 domain, and a CH3 domain wherein:
   (a) the CH1 domain comprises a human IgG1 CH1 domain or a human IgG4 CH1 domain having the amino acid sequence DKKV or DKRV from positions 212 to 215 (EU numbering),
   (b) the hinge comprises a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering),
   (c) the CH2 domain comprises a human IgG4 CH2 domain amino acid sequence from positions 237 to 340 (EU numbering), and
   (d) the CH3 domain comprises a human IgG1 or a human IgG4 CH3 domain sequence from positions 341 to 447 (EU numbering), and
   wherein the antibody is capable of binding to an FcγR with lower affinity than a corresponding antibody comprising a wild-type IgG1 or wild-type IgG4 heavy chain constant region, the antibody is capable of binding FcγRIIA and optionally FcγRIIB, and the antibody is capable of binding FcγRIIA with higher affinity compared to its binding affinity to FcγRIIB.

2. Nucleic acid molecules encoding an antibody of claim 1.

3. A vector comprising the nucleic acid molecules of claim 2.

4. A cell comprising the nucleic acid molecules of claim 2.

5. An Fc-fusion protein comprising a heavy chain constant (CH) region comprising, from N-terminus to C-terminus, a CH1 domain, a hinge, a CH2 domain, and a CH3 domain wherein:
 (a) the CH1 domain comprises the amino acid sequence DKKV or DKRV from positions 212 to 215 (EU numbering),
 (b) the hinge comprises a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering),
 (c) the CH2 domain comprises a human IgG4 CH2 domain amino acid sequence from positions 237 to 340 (EU numbering), and
 (d) the CH3 domain comprises a human IgG1 or a human IgG4 CH3 domain sequence from positions 341 to 447 (EU numbering), and
 wherein the Fc-fusion protein is capable of binding to an FcγR with lower affinity than a corresponding Fc-fusion protein comprising a wild-type IgG1 or wild-type IgG4 heavy chain constant region, the Fc-fusion protein is capable of binding FcγRIIA and optionally FcγRIIB, and the Fc-fusion protein is capable of binding FcγRIIA with higher affinity compared to its binding affinity to FcγRIIB.

6. A nucleic acid molecule encoding an Fc-fusion protein of claim 5.

7. A vector comprising the nucleic acid molecule of claim 6.

8. A cell comprising the nucleic acid molecule of claim 6.

9. A bispecific antibody comprising:
 (a) a first heavy chain comprising an antigen-binding domain capable of recognizing and binding to a first target antigen,
 (b) a second heavy chain comprising an antigen-binding domain capable of recognizing and binding to a second target antigen, and
 (c) a common light chain antigen-binding domain capable of recognizing and binding to the first or second target antigen,
 wherein the heavy chain of (a) or (b) or both (a) and (b) comprises a chimeric IgG4 heavy chain constant (CH) region comprising an IgG4 CH1 domain, an IgG4 upper hinge from positions 216 to 227 (EU numbering), an IgG2 lower hinge from positions 228 to 236 (EU numbering), an IgG4 CH2 domain, and an IgG4 CH3 domain, or the heavy chain of (a) or (b) or both (a) and (b) comprises a chimeric IgG1 CH region comprising an IgG1 CH1 domain, an IgG1 upper hinge from positions 216 to 227 (EU numbering), an IgG2 lower hinge from positions 228 to 236 (EU numbering), an IgG4 CH2 domain, and an IgG1 CH3 domain,
 wherein the bispecific antibody is capable of binding to an FcγR with lower affinity than a corresponding bispecific antibody comprising a wild-type IgG1 or wild-type IgG4 heavy chain constant region, the bispecific antibody is capable of binding FcγRIIA and optionally FcγRIIB, and the bispecific antibody is capable of binding FcγRIIA with higher affinity compared to its binding affinity to FcγRIIB.

10. Nucleic acid molecules encoding a bispecific antibody of claim 9.

11. A vector comprising the nucleic acid molecules of claim 10.

12. A cell comprising the nucleic acid molecules of claim 10.

13. A method of making an antibody, said method comprising:
 (a) transfecting a host cell with a nucleic acid molecule encoding a light chain of said antibody, said nucleic acid molecule comprising a nucleotide sequence encoding the $V_L$ region of a selected antigen-specific antibody and a nucleotide sequence encoding the constant $C_L$ region of an Ig, wherein said nucleotide sequence encoding the $V_L$ region of a selected antigen-specific antibody and said nucleotide sequence encoding the $C_L$ region of an Ig are operably linked together;
 (b) transfecting the host cell of step (a) with a nucleic acid molecule encoding a heavy chain of said antibody, said nucleic acid molecule comprising a nucleotide sequence encoding the $V_H$ region of a selected antigen-specific antibody and a nucleotide sequence encoding a constant $C_H$ region of a human Ig, wherein the nucleotide sequence encoding the $C_H$ region comprises the nucleotide sequence encoding SEQ ID NO: 1, SEQ ID NO: 2, SEQ ID NO: 30, SEQ ID NO: 31, SEQ ID NO: 37 or SEQ ID NO: 38, wherein said nucleotide sequence encoding the $V_H$ region of a selected antigen-specific antibody and said nucleotide sequence encoding the $C_H$ region of said Ig are operably linked together; and
 (c) making said antibody by co-expressing the nucleic acid molecules of (a) and (b) in said host cell, wherein the host cell is cultured and the antibody is secreted into a cell culture medium; and
 (d) isolating the antibody from the cell culture medium,
 wherein the antibody is capable of binding to an FcγR with lower affinity than a corresponding antibody comprising a wild-type IgG1 or wild-type IgG4 heavy chain constant region, the antibody is capable of binding to FcγRIIA and optionally FcγRIIB, and the antibody is capable of binding to FcγRIIA with higher affinity compared to its binding affinity to FcγRIIB.

14. A method of making an Fc-fusion protein, said method comprising:
 (a) transfecting a host cell with a nucleic acid molecule encoding said Fc-fusion protein, said nucleic acid molecule comprising a nucleotide sequence encoding a protein, fused to a nucleotide sequence encoding a constant $C_H$ region of a human Ig, wherein the nucleotide sequence encoding the $C_H$ region comprises the nucleotide sequence encoding SEQ ID NO: 1, SEQ ID NO: 2, SEQ ID NO: 30, SEQ ID NO: 31, SEQ ID NO: 37 or SEQ ID NO: 38, wherein said nucleotide sequence encoding the protein and said nucleotide sequence encoding the $C_H$ region of said Ig are operably linked together; and
 (b) making said Fc-fusion protein by expressing the nucleic acid molecule of (a) in said host cell, wherein the host cell is cultured and the Fc-fusion protein is secreted into a cell culture medium; and
 (c) isolating the Fc-fusion protein from the cell culture media,
 wherein the Fc-fusion protein is capable of binding to an FcγR with lower affinity than a corresponding Fc-fusion protein comprising a wild-type IgG1 or wild-type IgG4 heavy chain constant region, the Fc-fusion protein is capable of binding to FcγRIIA and optionally FcγRIIB, and the Fc-fusion protein is capable of binding to FcγRIIA with higher affinity compared to its binding affinity to FcγRIIB.

15. A composition comprising the antibody of claim 1, and a pharmaceutically acceptable carrier or diluent.

16. A bispecific antibody, comprising:
(a) a first heavy chain comprising an antigen-binding domain capable of recognizing and binding to a first target antigen,
(b) a second heavy chain comprising an antigen-binding domain capable of recognizing and binding to a second target antigen, and
(c) a common light chain antigen-binding domain capable of recognizing and binding to the first or second target antigen,
wherein the heavy chain of (a) or (b) or both (a) and (b) comprises the heavy chain constant region comprising a hinge comprising a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering).

17. A method of killing a target cell via antibody-dependent cellular phagocytosis, comprising contacting the target cell with an antibody comprising a variable region that binds an antigen on the target cell and a heavy chain constant region, wherein the heavy chain constant region comprises a hinge comprising a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering).

18. The method of claim 17, wherein the target cell is a tumor cell.

19. A method of making an antibody with decreased antibody-dependent cellular cytotoxicity (ADCC), comprising combining a variable region with a heavy chain constant region, wherein the heavy chain constant region comprises a hinge comprising a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering), wherein the antibody exhibits undetectable ADCC activity as measured in an in vitro or ex vivo cell killing assay at an antibody concentration of 100 nM.

20. A method of making an antibody that does not bind to human FcγRI or human FcγRIII, comprising combining a variable region with a heavy chain constant region, wherein the heavy chain constant region comprises a hinge comprising a human IgG1 or a human IgG4 upper hinge amino acid sequence from positions 216 to 227 (EU numbering) and a human IgG2 lower hinge amino acid sequence PCPAPPVA (SEQ ID NO: 3) from positions 228 to 236 (EU numbering), wherein the antibody exhibits undetectable binding to His-captured FcγRI and FcγRIII as measured in a surface plasmon resonance assay at 25° C.

* * * * *